US011674123B2

(12) United States Patent
Thomson et al.

(10) Patent No.: US 11,674,123 B2
(45) Date of Patent: Jun. 13, 2023

(54) GENERATING ARTERIAL ENDOTHELIAL CELL POPULATIONS

(71) Applicant: Wisconsin Alumni Research Foundation, Madison, WI (US)

(72) Inventors: James A. Thomson, Madison, WI (US); Jue Zhang, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 195 days.

(21) Appl. No.: 15/048,789

(22) Filed: Feb. 19, 2016

(65) Prior Publication Data

US 2016/0244719 A1 Aug. 25, 2016

Related U.S. Application Data

(60) Provisional application No. 62/118,553, filed on Feb. 20, 2015.

(51) Int. Cl.
*C12N 5/071* (2010.01)
*G01N 33/50* (2006.01)
*A61K 35/44* (2015.01)
*C12N 5/00* (2006.01)

(52) U.S. Cl.
CPC ............ *C12N 5/069* (2013.01); *A61K 35/44* (2013.01); *C12N 5/0031* (2013.01); *C12N 5/0056* (2013.01); *G01N 33/5064* (2013.01); *C12N 2500/35* (2013.01); *C12N 2500/90* (2013.01); *C12N 2500/98* (2013.01); *C12N 2501/10* (2013.01); *C12N 2501/113* (2013.01); *C12N 2501/15* (2013.01); *C12N 2501/155* (2013.01); *C12N 2501/16* (2013.01); *C12N 2501/165* (2013.01); *C12N 2501/415* (2013.01); *C12N 2501/42* (2013.01); *C12N 2506/02* (2013.01); *C12N 2506/45* (2013.01)

(58) Field of Classification Search
None
See application file for complete search history.

(56) References Cited

U.S. PATENT DOCUMENTS

| 6,143,292 | A | 11/2000 | Slavin | |
|---|---|---|---|---|
| 6,326,198 | B1 | 12/2001 | Emerson et al. | |
| 6,383,481 | B1 | 5/2002 | Ikehara et al. | |
| 6,441,053 | B1* | 8/2002 | Klein | A61K 31/404 424/610 |
| 6,447,765 | B1 | 9/2002 | Horwitz | |
| 2009/0104159 | A1 | 4/2009 | Prosper et al. | |
| 2012/0064040 | A1* | 3/2012 | McCloskey | A61K 35/44 424/93.7 |
| 2012/0295347 | A1* | 11/2012 | Kessler | C12N 5/0692 435/366 |
| 2014/0248694 | A1 | 9/2014 | Zhang et al. | |
| 2014/0248696 | A1* | 9/2014 | Zhang | C12N 5/0623 435/366 |
| 2018/0023051 | A1* | 1/2018 | Esmeraldo De Campos Vaz O ... | C12N 5/069 506/39 |

FOREIGN PATENT DOCUMENTS

| JP | 2007-529510 | 10/2007 | |
|---|---|---|---|
| JP | 2011-512201 | 4/2011 | |
| WO | WO9830679 | 7/1998 | |
| WO | 1998045479 A1 | 10/1998 | |
| WO | 2011090684 A2 | 7/2011 | |
| WO | 2013166165 A1 | 11/2013 | |
| WO | 2014040020 A2 | 3/2014 | |
| WO | 2014097192 A2 | 6/2014 | |
| WO | WO-2014097192 A2 * | 6/2014 | ............ C12N 5/069 |
| WO | 2014/165131 | 10/2014 | |

OTHER PUBLICATIONS

ATCC (Formulation for DMEM) (Year: 2012).*
Lian, Xiaojun et al. Efficient Differentiation of Human Pluripotent Stem Cells to Endothelial Progenitors via Small-Molecule Activation of WNT Signaling. Stem Cell Reports. vol. 3. pp. 804-816. Nov. 11, 2014 The Authors (Year: 2014).*
CDM-HD Serum Replacement (Year: 2019).*
Ataollahi et al. "New method for the isolation of endothelial cells from large vessels," Cytotherapy, 2014,16(8), 1145-1152.
Baba et al. "Constitutively active B-catenin confers multi-lineage differentiation potential on lymphoid and myeloid progenitors," Immunity 2005, 23:599-609.
Bae et al. "Building vascular networks," Sci transl Med, 2012, 4, 160ps123.
Berridge et al. "Neural and developmental actions of lithium: a unifying hypothesis," Cell, 1989, 59:411-419.
Chen et al. "Chemically defined conditions for human iPS cell derivation and culture," Nat Methods 2011 8(5):424-429.
Chong et al. "Stepwise arteriovenous fate acquisition during mammalian vasculogenesis," Dev Dyn, 2011, 240:2153-2165.
De Caterina et al. "Nitric oxide decreases cytokine-induced endothelial activation," J Clin Invest, 1995, 96:60-68.
Ebert et al. "Induced pluripotent stem cells from a spinal muscular atrophy patient," Nature 2009,457(7227):277-280.
Hagen et al. "Expression and characterization of GSK-3 mutants and their effect on B-catenin phosphorylation in intact cells" J Biol Chem, 2002, 277:23330-5.

(Continued)

*Primary Examiner* — Nghi V Nguyen
(74) *Attorney, Agent, or Firm* — McDonnell Boehnen Hulbert & Berghoff LLP

(57) ABSTRACT

Methods for generating human arterial endothelial cells under defined conditions in the absence of insulin are described. In particular, provided herein are efficient, defined, and scalable methods for generating human arterial endothelial cells from human pluripotent stem cells. Also provided herein are uses of human arterial endothelial cells obtained according to these methods. For example, methods of treating peripheral arterial disease and methods of screening agents for that effect adhesion of leukocytes to arterial endothelial cells are also provided.

12 Claims, 17 Drawing Sheets
(17 of 17 Drawing Sheet(s) Filed in Color)

(56) References Cited

OTHER PUBLICATIONS

Hauser et al. "Differential induction of VCAM-1 on human iliac venous and arterial endothelial cells and its role in adhesion," J Immunol, 1993, 151:5172-5185.

Hong et al. "Artery/vein specification is governed by opposing phosphatidylinositol-3 kinase and MAP kinase/ERK signaling," Curr Biol, 2006, 16:1366-1372.

Hou et al. "Efficient genome engineering in human pluripotent stem cells using Cas9 from Neisseria meningitidis," Proc Natl Acad Sci USA, 2013, 110:15644-15649.

Howden et al. "Genetic correction and analysis of induced pluripotent stem cells from a patient with gyrate atrophy," Proc. Natl. Acad. Sci. USA 2011, 108(16);6537-42.

Inman et al. "SB-431542 Is a potent and specific inhibitor of transforming growth factor-B superfamily type 1 activin receptor-like kinase (ALK) receptors ALK4, ALK5, ALK7," Mol. Pharmacol., 2002, 62(1):65-74.

International Search Report and Written Opinion, PCT/US2016/018769, dated May 18, 2016.

Jiang et al. "Enhanced cellular responses and distinct gene profiles in human fetoplacental artery endothelial cells under chronic low oxygen," Biology of Reproduction, 2013, 89(6):133, 1-10.

Kalogeris et al. "Effect of selective proteasome inhibitors on TNF-induced activation of primary and transformed endothelial cells," Am J Physiol, 1999, 276:L9-L19.

Kim et al. "Human peripheral blood-derived CD31+ cells have robust angiogenic and vasculogenic properties and are effective for treating ischemic vascular disease," J Am Coll Cardiol 2010, 56:293-607.

Lu et al. "Long-term safety and function of RPE from human embryonic stem cells in preclinical models of macular degeneration," Stem Cells 2009, 27:2126-2135.

Mackenzie and Elliot "Akt/PKB activation and insulin signaling: a novel insulin signaling pathway in the treatment of type 2 diabetes," Diabetes, Metabolic Syndrome and Obesity: Targets and Therapy, 2014, 2014:7:55-64.

Owens et al. "Molecular regulation of vascular smooth muscle differentiation in development and disease," Physiol Rev, 2004, 84:767-801.

Pearson, et al., "The stepwise specification of embryonic stem cells to hematopoietic fate is driven by sequential exposure to Bmp4, activin A, bFGF and VEGF," Development, The Company of Biologists Ltd, GB, 2008, 135(8), 1525-1535.

Rufaihah et al. "Human induced pluripotent stem cell-derived endothelial cells exhibit functional heterogeneity," Am. J. Transl. Res., 2013, 5(1):21-35.

Shutter et al. "Dll4, a novel Notch ligand expressed in arterial endothelium," Genes & Dev. 2000, 14:1313-18.

Thomson et al. "Embryonic stem cell lines derived from human blastocysts," Science 1998, 282:1145-1147.

Wang et al. "Molecular distinction and angiogenic interaction between embryonic arteries and veins revealed by ephrin-B2 and its receptor Eph-B4," Cell, 1998, 93:741-753.

Yu et al "Induced pluripotent stem cell lines derived from human somatic cells," Science 2007, 318:1917-1920.

Yu et al "Human induced pluripotent stem cells free of vector and transgene sequences," Science 2009, 324 (5928):797-801.

Office Action dated Oct. 15, 2018 from related Japanese Patent Application No. 2017-543823, 14 pages including English translation.

Garcia-Gonzalo & Izpisua Belmonte, "Albumin-associated lipids regulate human embryonic stem cell self-renewal," PLoS One 3(1):e1384 (2008).

Odorico et al., "Multilineage differentiation from human embryonic stem cell lines," Stem Cells 19(3): 193-204 (2001).

Sigma-Aldrich, Nutridoma-CS, p. 1-3 (accessed Jul. 18, 2018).

ThermoFisher Scientific, Advanced DMEM/F12 Media, Catalog No. 12634028 p. 1-3.

* cited by examiner

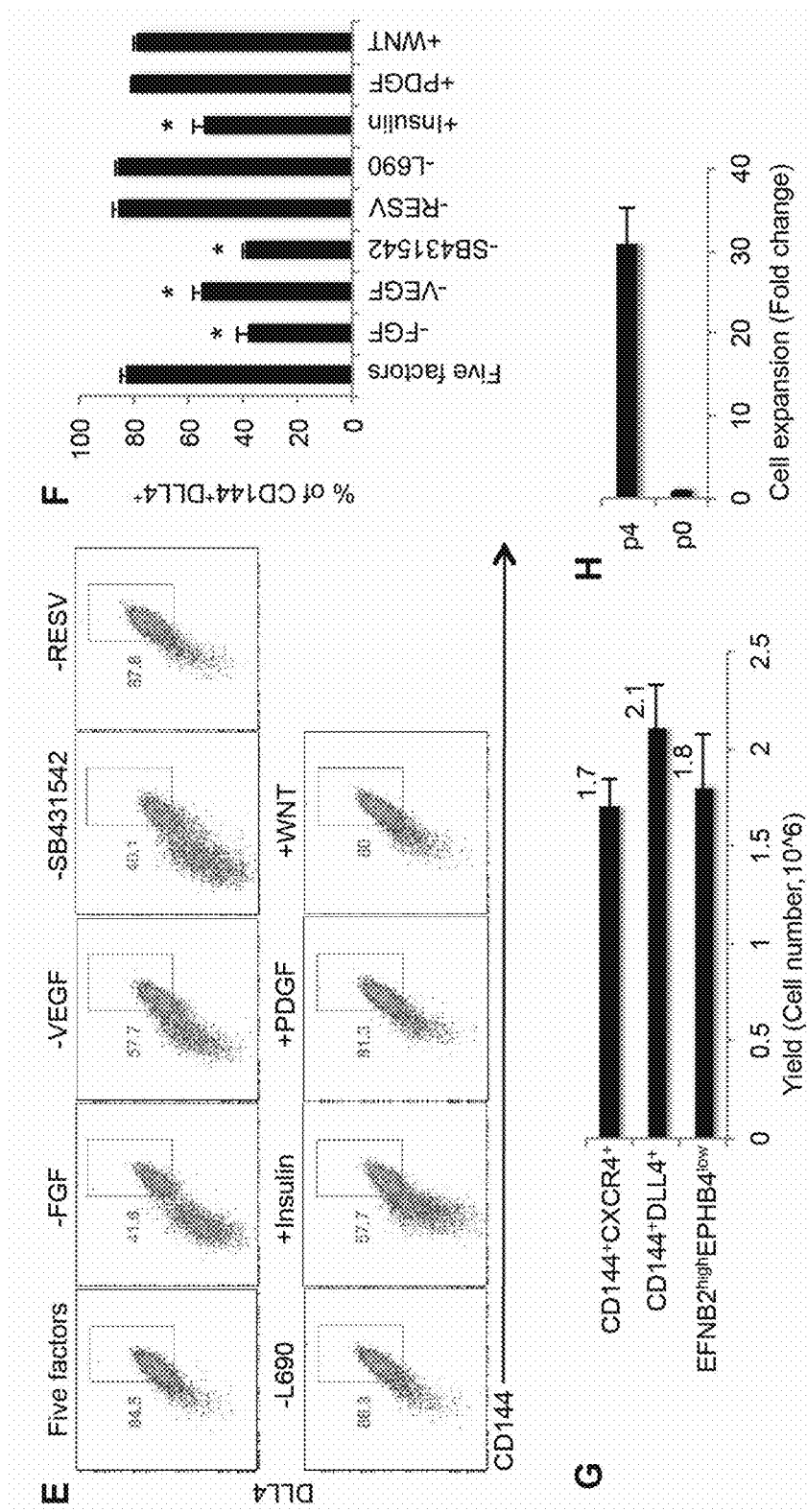
FIGS. 4A-4H, CONTINUED

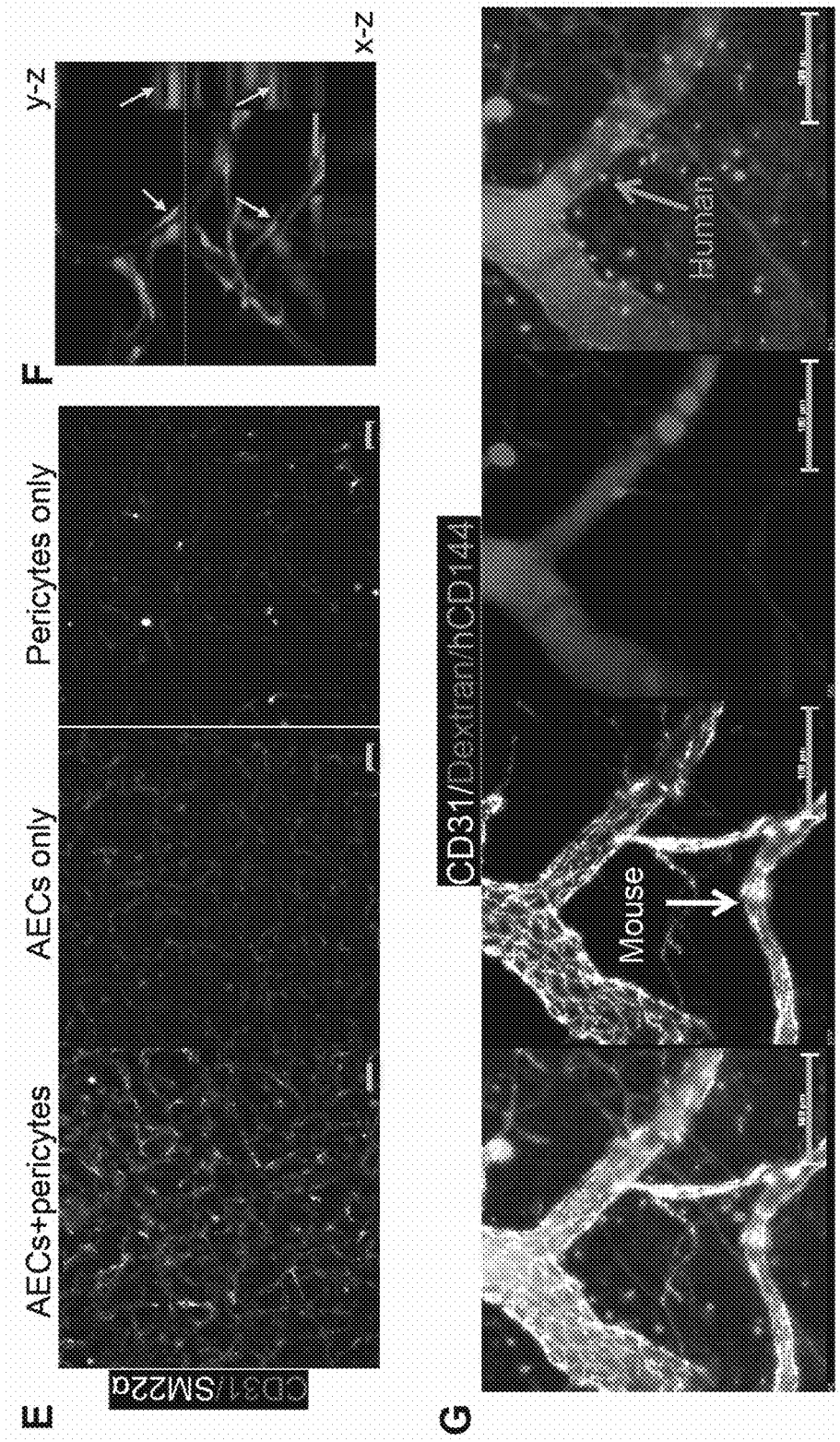
FIGS. 5A-5G, CONTINUED

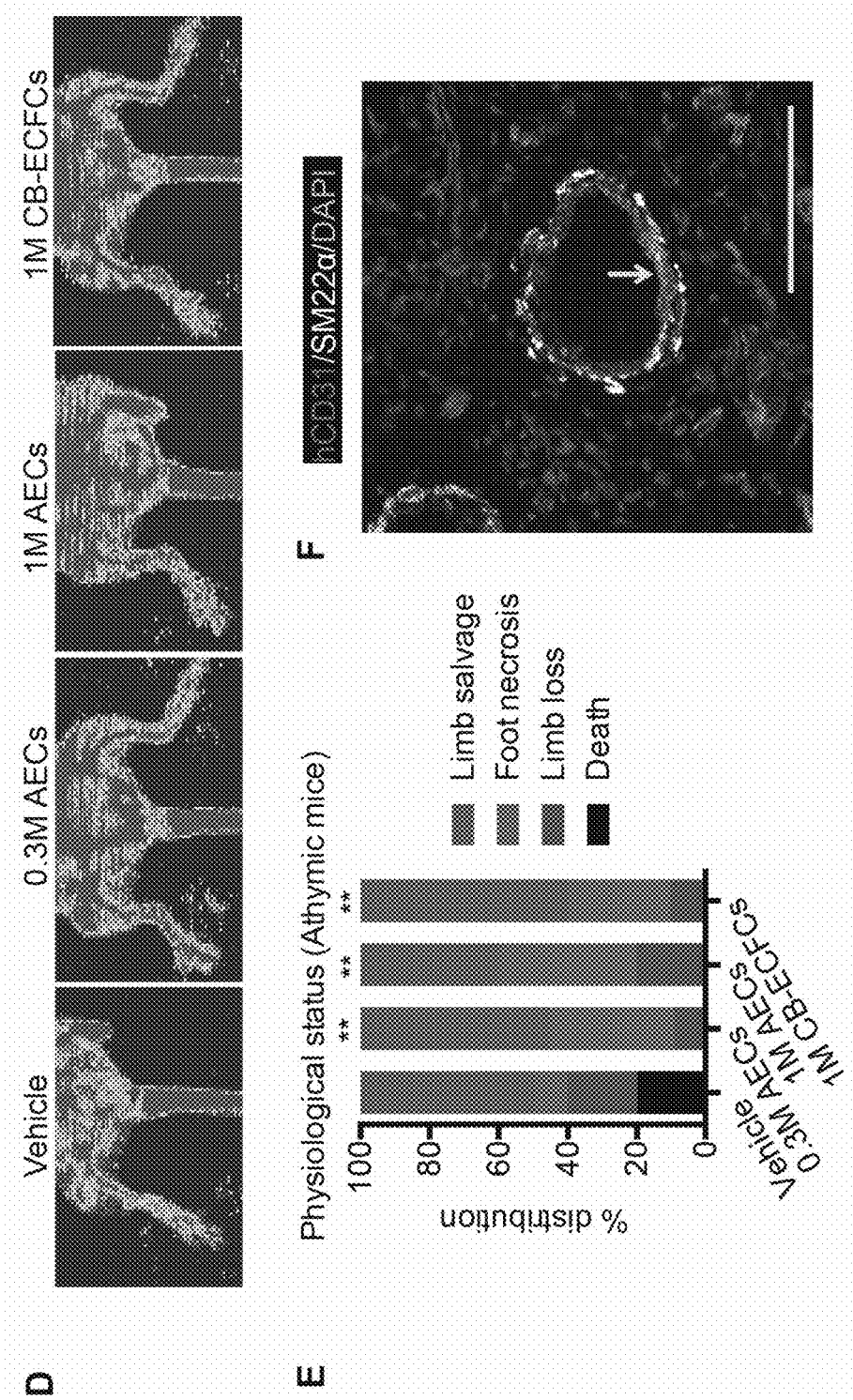
FIGS. 6A-6F, CONTINUED

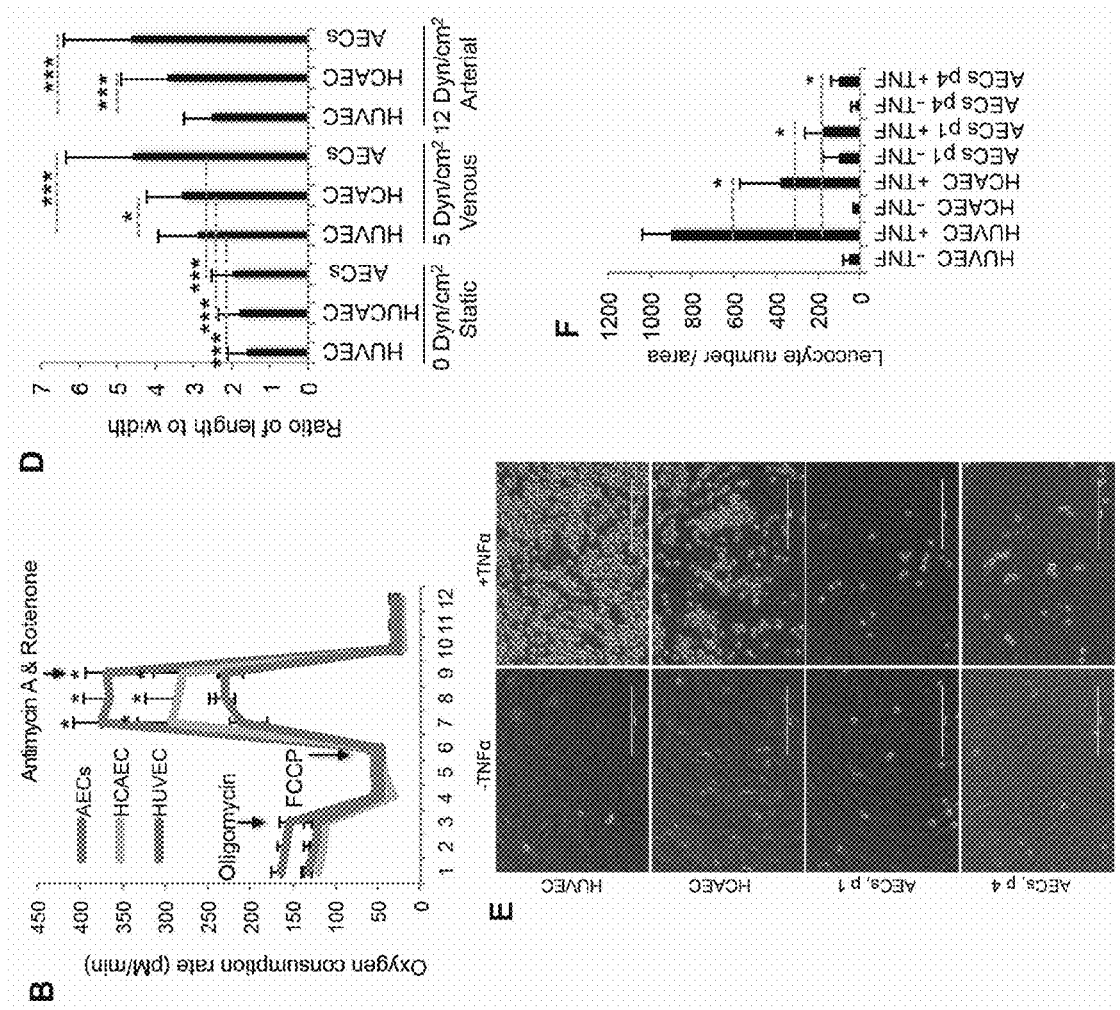
FIGS. 7A-7F, CONTINUED

FIGS. 8A-8J, CONTINUED
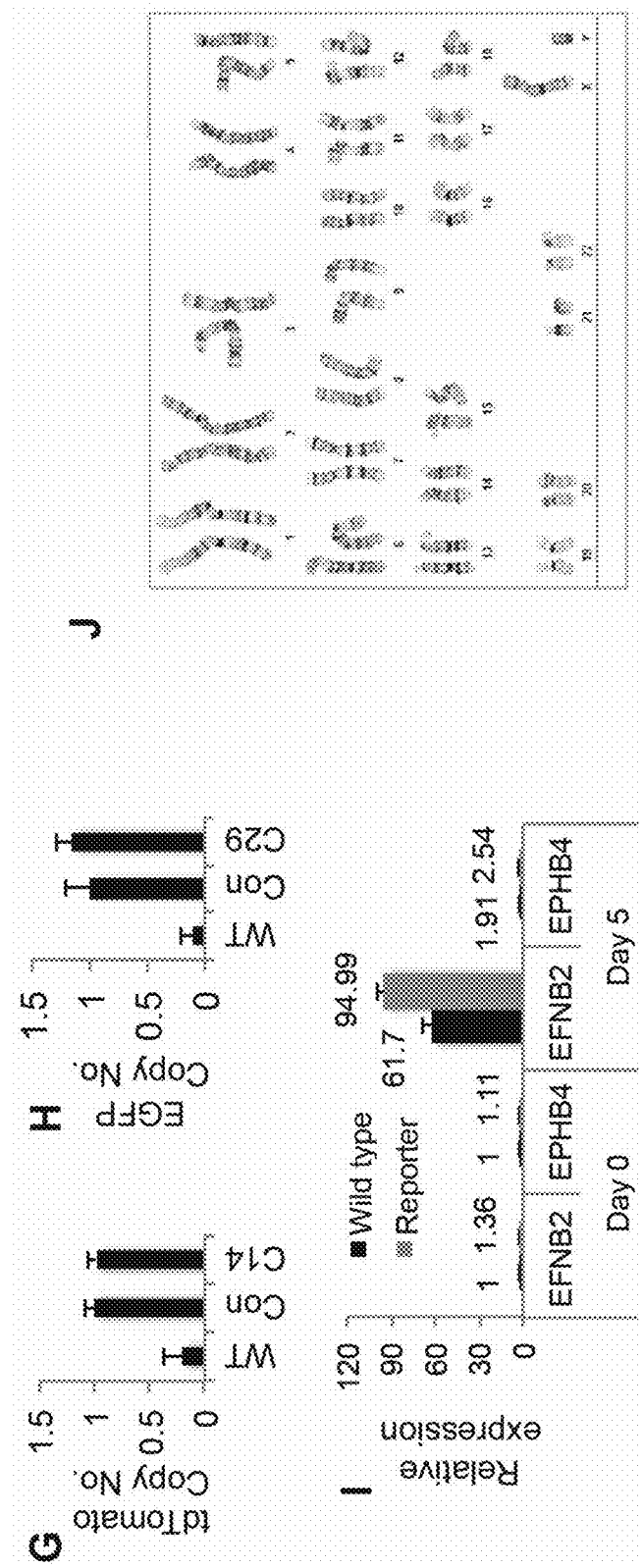

GENERATING ARTERIAL ENDOTHELIAL CELL POPULATIONS

CROSS-REFERENCE TO RELATED APPLICATIONS

This application claims priority to U.S. Provisional Application No. 62/118,553, filed Feb. 20, 2015, which is incorporated herein by reference in its entirety.

LENGTHY TABLES

The patent contains a lengthy table section. A copy of the table is available in electronic form from the USPTO web site (https://seqdata.uspto.gov/?pageRequest=docDetail&DocID=US11674123B2). An electronic copy of the table will also be available from the USPTO upon request and payment of the fee set forth in 37 CFR 1.19(b)(3).

STATEMENT REGARDING FEDERALLY FUNDED RESEARCH OR DEVELOPMENT

This invention was made with government support under UH2-TR000506 awarded by the National Institutes of Health (National Center for Advancing Translational Sciences). The government has certain rights in the invention.

BACKGROUND

Cardiovascular disease is the leading cause of death in U.S., and most vascular diseases, such as atherosclerosis, occur in the arteries. Atherosclerosis is a chronic inflammatory disease that is initiated by activation, dysfunction, and structural changes of the endothelial cells, leading to increased leukocyte-endothelial adhesion.

Generating arterial endothelial cells from pluripotent stem cells holds great promise for the development of therapies for diseases or conditions that would treat cardiovascular disease. However, arterial endothelial development is challenging, as primary arterial endothelial cells undergo de-differentiation in culture. For instance, U.S. Published Patent Application No. 2009/0104159 to Prosper et al. describes methods of culturing and using vascular endothelial cells that demonstrate the "potential" for arterial differentiation (paragraph [0136]). Further, U.S. Published Patent Application No. 2012/0064040 to McCloskey et al. describes chemically defined culture conditions to derive endothelial cells from embryonic stem cells. However, here again, this disclosure appears to merely demonstrate the potential for differentiating arterial endothelial cells from embryonic stem cells, and achieves very low results.

Existing protocols for deriving arterial endothelial cells from human embryonic stem cells have been largely unsuccessful. Accordingly, there remains a need in the art for efficient, defined, and scalable methods for generating human arterial endothelial cells from human pluripotent stem cells.

SUMMARY OF THE INVENTION

In a first aspect, provided herein is a method of obtaining arterial endothelial cells. The method can comprise or consist essentially of culturing mesodermal cells in a serum-free, albumin-free, chemically defined culture medium that is substantially free of insulin and comprises a fibroblast growth factor (FGF), a vascular endothelial growth factor (VEGF), and at least one of a Notch agonist, a TGF-beta inhibitor, and an inhibitor of inositol monophosphatase, whereby a cell population comprising arterial endothelial cells is obtained. The arterial endothelial cells of the population can express one or more markers selected from the group consisting of neuropilin1 (NRP-1), Delta-like 4 (DLL4), ephrin-B2 (EFNB2), CD44, CXCR4/CD184, Gap Junction Protein Alpha-4 (GJA4), Hey1, Jagged-1 (JAG1), Notch1, and Notch4. The cell population can comprise at least 80% arterial endothelial cells.

The serum-free, albumin-free, chemically defined culture medium can comprise a FGF, a VEGF, a Notch agonist, a TGF-beta inhibitor, and an inhibitor of inositol monophosphatase. The mesodermal cells can express one or more mesodermal markers selected from the group consisting of Brachyury (T), EMOS, FOXA2, MIXL1, MSX1, and MSX2.

In some cases, the mesodermal cells are obtained by culturing human pluripotent stem cells for a period of about two days in a serum-free, albumin-free, chemically defined cell culture medium comprising a Bone Morphogenetic Protein (BMP), Activin A, and an activator of Wnt/β-catenin signaling to obtain a cell population comprising mesodermal cells. The mesodermal cells can express one or more mesodermal markers selected from the group consisting of Brachyury (T), EMOS, FOXA2, MIXL1, MSX1, and MSX2. The pluripotent stem cells can be human embryonic stem cells or human induced pluripotent stem cells. The activator of Wnt/β-catenin signaling can be a Gsk3 inhibitor. The Gsk3 inhibitor can be selected from the group consisting of CHIR 99021, CHIR 98014, BIO-acetoxime, BIO, LiCl, SB 216763, SB 415286, AR A014418, 1-Azakenpaullone, and Bis-7-indolylmaleimide. The Notch agonist can be selected from the group consisting of Resveratrol (3,4',5-trihydroxystilbene), valproic acid, and suberoyl bishydroxamic acid. The TGF-beta inhibitor can be SB431542. The inhibitor of inositol monophosphatase can be L-690, 330.

In another aspect, provided herein is a substantially pure, isolated population of arterial endothelial cells obtained according to a method provided herein. The isolated population can comprise at least 90% arterial endothelial cells or at least 99% arterial endothelial cells.

In another aspect, provided herein is a substantially pure, isolated population of pluripotent stem cell-derived arterial endothelial cells obtained according to a method provided herein. The isolated population can comprise at least 90% arterial endothelial cells or at least 99% arterial endothelial cells.

In a further aspect, provided herein is a method of in vitro screening test agents. The method can comprise contacting a test agent to arterial endothelial cells obtained according to a method provided herein; and detecting an effect of the agent on the contacted arterial endothelial cells. Detecting can comprise performing a method selected from the group consisting of leukocyte adhesion assay, RNA sequencing, gene expression profiling, transcriptome analysis, metabolome analysis, detecting reporter or sensor, protein expression profiling, Förster resonance energy transfer (FRET), metabolic profiling, and microdialysis.

In yet another aspect, provided herein is a kit for obtaining arterial endothelial cells, the kit comprising: (i) a serum-free, albumin-free, chemically defined culture medium suitable for differentiation of mesodermal cells into arterial endothelial cells, wherein the culture medium is substantially free of insulin and comprises a fibroblast growth factor (FGF), a vascular endothelial growth factor (VEGF), and at least one of a Notch agonist, a TGF-beta inhibitor, and an inhibitor of inositol monophosphatase; and (ii) instructions describing a method for differentiating mesodermal cells into arterial endothelial cells, the method employing the culture medium. The kit can further comprise (a) a serum-free, albumin-free, chemically defined culture medium suitable for differentiation of human pluripotent stem cells into mesodermal cells, where the culture medium comprises a BMP, Activin A, and an activator of Wnt/β-catenin signaling; and (b) instructions describing a method for differentiating human pluripotent stem cells into arterial endothelial cells, the method employing the culture medium of (a).

These and other features, aspects, and advantages of the present invention will become better understood from the description that follows. In the description, reference is made to the accompanying drawings, which form a part hereof and in which there is shown by way of illustration, not limitation, embodiments of the invention. The description of preferred embodiments is not intended to limit the invention to cover all modifications, equivalents and alternatives. Reference should therefore be made to the claims recited herein for interpreting the scope of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the compositions and methods provided herein. The invention may be better understood by reference to one or more of these drawings in combination with the detailed description of specific embodiments presented herein.

FIG. 4B illustrates the percentage of arterial endothelial cells (AEC) (EFNB2-tdTomato$^{high}$/EPHB4-EGFP$^{low}$) obtained after differentiation in the various medium conditions of FIG. 4A.

Data are represented as mean±SD. FIG. 4C shows flow cytometric analysis of expression of CXCR4 and CD144 on endothelial cells obtained after differentiation in various medium. FIG. 4D illustrates the percentage of CXCR4$^+$CD144$^+$ arterial endothelial cells obtained after differentiation in the various medium conditions of FIG. 4C. FIG. 4E shows flow cytometric analysis of expression of DLL4 and CD144 on endothelial cells obtained after differentiation in various medium. FIG. 4F illustrates the percentage of DLL4$^+$CD144$^+$ arterial endothelial cells obtained after differentiation in the various medium conditions of FIG. 4E. 5 µM L-690,330 (a bisphosphonate inhibitor of inositol monophosphatase), and 100 ng/ml PDGF-BB (platelet derived growth factor BB) were used. FIG. 4G shows the statistics of arterial endothelial cell number generated from $1.0 \times 10^6$ starting ES cells after six days of differentiation ("five factors" medium). FIG. 4H shows the expansion of EFNB2-tdTomato$^{high}$/EPHB4-EGFP$^{low}$ cells from passage 0 to passage 4.

DETAILED DESCRIPTION OF THE INVENTION

Figures 1A, 1B, 1C, 1D:
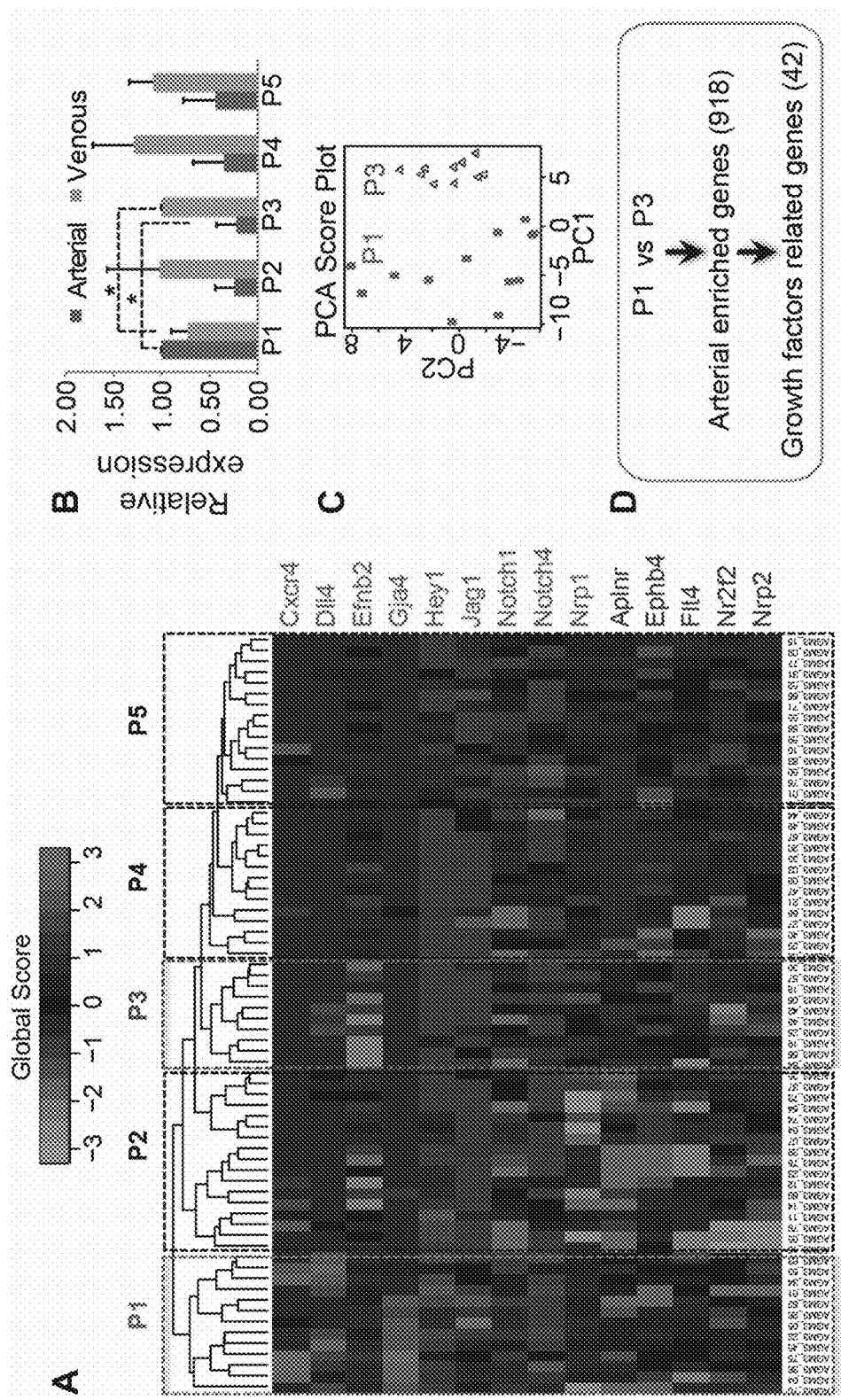
FIGS. 1A-1D demonstrate single-cell RNA-seq. (A) Hierarchical clustering analysis of arterial and venous genes of single cells. (B) Average arterial and venous gene expression of five cell subpopulations. In each subpopulation, the average TPM (transcript per million) of each gene was calculated and normalized to population P1 (arterial genes) or P3 (venous genes). The normalized expression of all arterial genes or venous genes was further averaged and shown in a bar graph. Data were represented as mean±SD. *: P<0.05, n=13 cells in P1, n=10 cells in P3. (C) Principal component analysis of P1 and P3. The plot was generated by Singular™ Analysis Toolset 2.1. (D) Arterial enriched genes. The mean TPM of each gene for P1 was compared to P3 to calculate fold change. P-value was also calculated by comparing P1 to P3. Arterial enriched genes were identified with fold change>2, P value<0.1, and the mean TPM of P1>10. P<0.1 was used as the cut off since the P value of the previously reported arterial genes, VEGFa, Fzd4, Fzd7, Fzd10, Dll4, and Notch4, was between 0.01 to 0.1.

All publications, including but not limited to patents and patent applications, cited in this specification are herein incorporated by reference as though set forth in their entirety in the present application.

The present invention is based, at least in part, on the Inventors' discovery that arterial endothelial cell differentiation was greatly improved by combining several specific factors as compared to single factors. As described herein, the inventors further discovered that certain factors (insulin, TGFβ, and PDGF) inhibit arterial endothelial differentiation.

Methods

In exemplary embodiments, the methods provided herein comprise differentiating mesodermal stem cells into arterial endothelial cells. As used herein, the term "arterial endothelial cell" (AEC) refers to cells of the arterial vascular endothelial lineage obtained according to a method provided herein. AECs of the present invention are characterized by high levels of expression of arterial endothelium markers such as EphrinB2, DLL4, Hey-2, jagged-1, and jagged-2. AECs are also characterized by low leukocyte adhesion, higher NO production and oxygen consumption, response to shear stress, and capacity to form vascular networks in vitro and in vivo while maintaining expression of arterial markers in such networks. AECs are distinguishable from other cell types, including endothelial cells (ECs), venous endothelial cells, and endothelial progenitor cells, on the basis of characteristic expression profiles and functional attributes of the cells in vitro as described herein.

In a first aspect, provided herein is a method of obtaining arterial endothelial cells. In exemplary embodiments, the method comprises directing differentiation of mesodermal cells into cells of the arterial endothelial cell lineage. As used herein, the terms "mesodermal cell" and "mesoderm cell" are used interchangeably and refer to a cell having mesoderm-specific gene expression and being capable of differentiating into a mesodermal lineage such as bone, muscle such as cardiac muscle, skeletal muscle and smooth muscle (e.g., of the gut), connective tissue such as the dermis and cartilage, kidneys, the urogenital system, blood or hematopoietic cells, heart and vasculature. Mesoderm-specific biomarkers include Brachyury (T).

Throughout the AEC differentiation steps provided herein, mesodermal cells are typically cultured in a culture medium that is free, substantially free, or essentially free of insulin, albumin, or any component derived from a non-human animal (i.e., free of xenogeneic material). As used herein, the term "substantially free" refers to cell culture conditions substantially devoid of a certain component or reagent. Accordingly, substantially free of insulin means that the culture medium comprises less than 2% of insulin by weight, and preferably contains less than 1%, less than 0.5%, less that 0.2% or less that 0.1% of insulin.

In addition, the culture medium comprises, or consists essentially of, one or more of a Fibroblast Growth Factor (FGF), a vascular endothelial growth factor (VEGF), an inhibitor of TGF-beta signaling (e.g., SB431542), Resveratrol (RESV), and an inhibitor of inositol monophosphatase, where culturing occurs for a length of time sufficient for the cultured mesoderm cells to differentiate into arterial endothelial cells. In some embodiments, the cell culture medium used for AEC differentiation methods described herein comprises each of these components. In other cases, the culture medium is substantially free of one or more of these ingredients. Culturing can take place on any appropriate surface (e.g., in two-dimensional or three-dimensional culture).

In some cases, a mesodermal cell (including, in some cases, a pluripotent stem-cell derived mesodermal cell) is cultured in medium that comprises an FGF, VEGF, a Notch agonist, a TGFβ receptor inhibitor, and an inhibitor of inositol monophosphatase in amounts effective to direct differentiation of a mesodermal cell to the arterial endothelial lineage. In some cases, the FGF is FGF2. VEGF is a heparin-binding glycoprotein that acts as a specific endothelial cell mitogen. In some cases, the VEGF is VEGF-A (vascular endothelial growth factor A) or an isoform thereof (e.g., VEGF-165). Exemplary human VEGF-A protein sequences comprise Genbank: AAH65522.2 and GenBank: AAH1 1177.2, and the nucleic acids encoding all of or encoding the non-precursor part of such are encompassed.

TGFβ receptor inhibitors appropriate for use in a method of the present invention include, without limitation, SB-431542, SB-525334, A83-01, LY2157299, LY210976, GW788388, RepSox, SB-505124, D4476, GW788388, SD208, and EW-7197. Preferably, the inhibitor of TGF-beta signaling is SB431542, a small molecule inhibitor of endogenous activin and the type I receptor (TGFβ Receptor I) (Inman et al., *Mol Pharmacol.* 62(1):65-74 (2002).

Notch is a single-pass cell-surface receptor that binds to a family of cell-surface ligands including the Delta-like and Jagged families. As used herein, the terms "Notch agonist"

and "Notch activator" refer to molecules (e.g., biomolecules, small molecules, chemicals) that bind to Notch receptor and initiate or mediumte signaling events associated with Notch activation. Resveratrol (3,4',5-trihydroxystilbene) belongs to a class of polyphenolic compounds called stilbenes and is an activator (agonist) of Notch signaling. Other Notch agonists appropriate for use according to methods for promoting arterial differentiation provided herein include valproic acid and suberoyl bishydroxamic acid. In addition, immobilized or multimerized soluble Notch ligands such as immobilized DLL4 and immobilized Jagged-1 peptide also can be used as Notch activators.

Inositol monophosphatase (IMPase) catalyses the hydrolysis of myo-inositol monophosphates to myo-inositol, which is required in the phosphoinositide cell signaling pathway. In some cases, an inhibitor of IMPase is the biphosphonate L-690,330 ([144-Hydroxyphenoxy)ethylidene]bisphosphonic acid). Lithium also inhibits IMPase to attenuate phosphoinositide signaling (Berridge et al., *Cell* 59:411-419 (1989)). Other inhibitors of the phosphoinositide signaling pathway include, without limitation, phosphoinositide 3-kinase (PI3K) inhibitor Ly294002, Pictilisib, HS-173, GSK2636771, Duvelisib, TG100-115, GSK1059615, PF-04691502, PIK-93, BGT226, AZD6482, SAR245409, BYL719, CUDC-907, IC-87114, TG100713, Gedatolisib, CH5132799, PKI-402, BAY 80-6946, XL147, PIK-90, PIK-293, PIK-294, Quercetin, Wortmannin, ZSTK474, AS-252424, AS-604850, and Apitolisib.

A suitable working concentration range for chemical inhibitors such as those described herein is from about 0.1 µM to about 100 µM e.g., about 2 µM, 5 µM, 7 µM, 10 µM, 12 µM, 15 µM, 18 µM, or another working concentration of one or more the foregoing chemical inhibitors between about 0.1 µM to about 100 µM.

Preferably, mesodermal cells are cultured in the AEC differentiation medium until at least about 80% (e.g., at least 80%, 85%, 90%, 95%, 99%) of the resulting cell population are arterial endothelial cells. Arterial endothelial cells characteristically have the following expression profile: $CD31^+/CD144^+/CD41^-/CD45^-$.

For several of the biological markers described herein, expression will be low or intermediumte in level. While it is commonplace to refer to cells as "positive" or "negative" for a particular marker, actual expression levels are a quantitative trait. The number of molecules on the cell surface can vary by several logs, yet still be characterized as "positive." Accordingly, characterization of the level of staining permits subtle distinctions between cell populations. Expression levels can be detected or monitored by flow cytometry, where lasers detect the quantitative levels of fluorochrome (which is proportional to the amount of cell surface antigen bound by the antibodies). Flow cytometry or fluorescence-activated cell sorting (FACS) can be used to separate cell populations based on the intensity of antibody staining, as well as other parameters such as cell size and light scatter. Although the absolute level of staining may differ with a particular fluorochrome and antibody preparation, the data can be normalized to a control.

Any appropriate method can be used to detect expression of biological markers characteristic of cell types described herein. For example, the presence or absence of one or more biological markers can be detected using, for example, RNA sequencing (e.g., RNA-seq), immunohistochemistry, polymerase chain reaction, quantitative real time PCR (qRT-PCR), or other technique that detects or measures gene expression. RNA-seq is a high-throughput sequencing technology that provides a genome-wide assessment of the RNA content of an organism, tissue, or cell. Alternatively, or additionally, one may detect the presence or absence or measure the level of one or more biological markers of AECs using, for example, via fluorescent in situ hybridization; (FISH; see WO98/45479 published October 1998), Southern blotting, Northern blotting, or polymerase chain reaction (PCR) techniques, such as qRT-PCR. In exemplary embodiments, a cell population obtained according to a method provided herein is evaluated for expression (or the absence thereof) of biological markers of arterial endothelial cells such as EFNB2, Cxcr4, Delta-like 4 (DLL4), Gja4, Hey1, Jag1, Notch1, Notch4, and Nrp1. Preferably, AECs express one or more of the following arterial endothelial cell markers: Ephrin B2 (EFNB2), Neuropilin-1 (NRP-1)/CD304, Delta-like 4 (DLL4), and CD184 (cluster of differentiation 184). The Ephrin B2 (EFNB2) gene encodes an EFNB class ephrin that binds to the EPHB4 and EPHA3 receptors. Neuropilin-1 (NRP1), which is also known as vascular endothelial cell growth factor 165 receptor (VEGF165R), is primarily expressed in arterial endothelial cells. DLL4 is a Notch ligand expressed in arterial endothelial cells (Shutter et al., *Genes & Dev.* 14:1313-18 (2000)). CD184 is also known as CXCR4 (C—X—C chemokine receptor type 4) or fusin. Quantitative methods for evaluating expression of markers at the protein level in cell populations are also known in the art. For example, flow cytometry is used to determine the fraction of cells in a given cell population that express or do not express biological markers of interest.

The terms "defined culture medium," "defined medium," and the like, as used herein, indicate that the identity and quantity of each medium ingredient is known. As used herein, the terms "chemically-defined culture conditions," "fully defined, growth factor free culture conditions," and "fully-defined conditions" indicate that the identity and quantity of each medium ingredient is known and the identity and quantity of supportive surface is known. As used herein, the term "albumin-free conditions" indicates that the culture medium used contains no added albumin in any form, including without limitation Bovine Serum Albumin (BSA), any form of recombinant albumin, or any other animal components.

Human pluripotent stem cells (hPSCs), either embryonic or induced, provide access to the earliest stages of human development and offer a platform on which to derive a large number of vasculogenic cells for cellular therapy and tissue engineering. Accordingly, in exemplary embodiments, the methods provided herein further comprise differentiating human pluripotent stem cells under conditions that promote differentiation of mesodermal stem cells into arterial endothelial cells. In such, a method of producing an arterial endothelial cell comprises culturing human pluripotent stem cells in a serum-free, albumin-free, chemically defined culture medium that promotes mesoderm differentiation. In this manner, pluripotent stem cell-derived mesodermal cells are differentiated according to the AEC differentiation methods provided herein, thus producing pluripotent stem cell-derived AECs. In exemplary embodiments, the serum-free, albumin-free, chemically defined culture medium that promotes mesoderm differentiation comprises Activin A, Bone Morphogenetic Protein 4 (BMP4), FGF2, and an activator of Wnt/β-catenin signaling.

Defined medium and substrate conditions for culturing pluripotent stem cells, as used in the methods described herein, are well known in the art. The medium used herein are limited only in that they are albumin-free. In some cases, pluripotent stem cells to be differentiated according to the methods disclosed herein are cultured in a serum-free, albumin-free medium.

As will be appreciated by those of ordinary skill in the art, Wnt/β-catenin signaling can be activated by modulating the function of one or more proteins that participate in the Wnt/β-catenin signaling pathway to increase β-catenin expression levels or activity, TCF and LEF expression levels, or β-catenin/TCF/LEF induced transcriptional activity.

In some embodiments, activation of Wnt/β-catenin signaling is achieved by inhibition of Gsk3 phosphotransferase activity or Gsk3 binding interactions. While not wishing to be bound by theory, it is believed that inhibition of Gsk3 phosphorylation of β-catenin will inhibit tonic degradation of β-catenin and thereby increase β-catenin's level and activity to drive differentiation of pluripotent stem cells to an endodermal/mesodermal lineage. Gsk3 inhibition can be achieved in a variety of ways including, but not limited to, providing small molecules that inhibit Gsk3 phosphotransferase activity, RNA interference knockdown of Gsk3, and overexpression of dominant negative form of Gsk3. Dominant negative forms of Gsk3 are known in the art as described, e.g., in Hagen, T. et al. *J Biol Chem,* 277:23330-5 (2002), which describes a Gsk3 comprising a R96A mutation.

In some embodiments, the Wnt/β-catenin signaling pathway is activated by inhibiting Gsk3 in pluripotent stem cells by contacting the pluripotent stem cells with a small molecule that inhibits Gsk3 phosophotransferase activity or Gsk3 binding interactions. Suitable small molecule Gsk3 inhibitors include, but are not limited to, CHIR 99021, CHIR 98014, BIO-acetoxime, BIO, LiCl, SB 216763, SB 415286, AR A014418, 1-Azakenpaullone, Bis-7-indolymaleimide, and any combinations thereof. In some embodiments, any of CHIR 99021, CHIR 98014, and BIO-acetoxime are used to inhibit Gsk3 in pluripotent stem cells in the differentiation methods described herein. In one embodiment, the small molecule Gsk3 inhibitor to be used is CHIR99021 at a concentration ranging from about 1 µM to about 9 µM, e.g., about 1 µM, 2 µM, 3 µM, 4 µM, 5 µM, 6 µM, 7 µM, 8 µM, 9 µM or another concentration of CHIR99021 from about 1 µM to about 9 µM. In another embodiment, the small molecule Gsk3 inhibitor to be used is CHIR 98014 at a concentration ranging from about 0.1 µM to about 1 µM, e.g., about 0.1 µM, 0.2 µM, 0.3 µM, 0.4 µM, 0.5 µM, 0.6 µM, 0.7 µM, 0.8 µM, 0.9 µM, 1.0 µM or another concentration of CHIR-98014 from about 0.1 µM to about 1 µM. In another embodiment, the small molecule Gsk3 inhibitor to be used is BIO-acetoxime at a concentration ranging from about 0.1 µM to about 1 µM, e.g., about 0.1 µM, 0.2 µM, 0.3 µM, 0.4 µM, 0.5 µM, 0.6 µM, 0.7 µM, 0.8 µM, 0.9 µM, 1.0 µM or another concentration of BIO-acetoxime from about 0.1 µM to about 1 µM.

In other embodiments, Gsk3 activity is inhibited by RNA interference knockdown of Gsk3. For example, Gsk3 expression levels can be knocked-down using commercially available siRNAs against Gsk3, e.g., SignalSilence® GSK-3α/β siRNA (catalog #6301 from Cell Signaling Techology®, Danvers, Mass.), or a retroviral vector with an inducible expression cassette for Gsk3, e.g., a commercially available Tet-inducible retroviral RNAi system from Clontech (Mountainview, Calif.) Catalog No. 630926, or a cumate-inducible system from Systems Biosciences, Inc. (Mountainview, Calif.), e.g., the SparQ® system, catalog no. QM200PA-2. In other embodiments, the Wnt/β-catenin signaling pathway is activated by overexpressing β-catenin itself, e.g., human β-catenin (GenBank Accession Nos: X87838 and CAA61107.1 for nucleotide and protein sequences, respectively). In one embodiment, β-catenin overexpression is inducible β-catenin overexpression achieved using, e.g., any of the just-mentioned inducible expression systems. Alternatively, a constitutively active, stabilized isoform of β-catenin is used, which contains point mutations S33A, S37A, T41A, and S45A as described, e.g., in Baba, Y. et al. Constitutively active β-catenin confers multi-lineage differentiation potential on lymphoid and myeloid progenitors. *Immunity* 23:599-609 (2005).

In yet other embodiments, Wnt/β-catenin signaling pathway activation in pluripotent stem cells is achieved by contacting the cells with an agent that disrupts the interaction of β-catenin with Axin, a member of the β-catenin destruction complex. Disruption of the Axin-β-catenin interaction allows β-catenin to escape degradation though the destruction complex thereby increasing the net level of β-catenin to drive β-catenin signaling. For example, the Axin-β-catenin interaction can be disrupted in pluripotent cells by contacting them with the compound 5-(Furan-2-yl)-N-(3-(1H-imidazol-1-yl)propyl)-1,2-oxazole-3-carboxamide ("SKL2001"), which is commercially available, e.g., as catalog no. 681667 from EMD4 Biosciences. An effective concentration of SKL2001 to activate Wnt/β-catenin signaling ranges from about 10 µM to about 100 µM, about 20 µM, 30 µM, 40 µM, 50 µM, 60 µM, 70 µM, 80 µM, 90 µM or another concentration of SKL2001 from about 10 µM to about 100 µM. In some embodiments the activator of Wnt/β-catenin signaling is a Gsk3 inhibitor. In some embodiments the Gsk3 inhibitor is selected from the group consisting of CHIR99021, CHIR98014, BIO-acetoxime, BIO, LiCl, SB216763, SB415286, AR A014418, 1-Azakenpaullone, and Bis-7-indolylmaleimide. In some embodiments the Gsk3 inhibitor is CHIR99021 or CHIR98014 at a concentration between about 0.1 µM to about 10 µM in the medium. In one embodiment, the small molecule Gsk3 inhibitor to be used is CHIR99021 at a concentration ranging from about 1 µM to about 9 µM, e.g., about 1 µM, 2 µM, 3 µM, 4 µM, 5 µM, 6 µM, 7 µM, 8 µM, 9 µM or another concentration of CHIR99021 from about 1 µM to about 9 µM. In another embodiment, the small molecule Gsk3 inhibitor to be used is CHIR98014 at a concentration ranging from about 0.1 µM to about 1 µM, e.g., about 0.1 µM, 0.2 µM, 0.3 µM, 0.4 µM, 0.5 µM, 0.6 µM, 0.7 µM, 0.8 µM, 0.9 µM, 1.0 µM or another concentration of CHIR98014 from about 0.1 µM to about 1 µM.

In exemplary embodiments, pluripotent stem cells are cultured in a chemically defined culture medium comprising or consisting essentially of DMEM/F12 culture medium, L-ascorbic acid-2-phosphate magnesium, sodium selenium, human FGF2, insulin, NaHCO₃, transferrin, TGFβ1, BMP4, Activin-A, and CHIR99021 ("E8BAC medium") for two days. Preferably, the culture medium comprises or consists essentially of DMEM/F12 medium; L-ascorbic acid-2-phosphate magnesium (64 mg/l); sodium selenium (14 µg/l); human FGF2(100 µg/l); insulin (20 mg/l); NaHCO3 (543 mg/l); transferrin (10.7 mg/l); TGFβ1 (2 µg/l); BMP4 (5 µg/l); Activin A (25 µg/l); and CHIR99021 (1 µM). Human pluripotent stem cells are cultured in the culture medium for about two days. After about two days, at least about 80% (e.g., at least about 80%, 85%, 90%, 95%, 99%) of the resulting cell population are mesoderm cells. As used herein, the term "mesoderm cell" refers to a cell having mesoderm-specific gene expression, capable of differentiating into a mesodermal lineage such as bone, muscle such as cardiac muscle, skeletal muscle and smooth muscle (e.g., of the gut), connective tissue such as the dermis and cartilage, kidneys, the urogenital system, blood or hematopoietic cells, heart and vasculature. Mesoderm-specific biomarkers include Brachyury (T). Culturing can take place on any appropriate surface (e.g., in two-dimensional or three-dimensional culture).

As used herein, "pluripotent stem cells" appropriate for use according to a method of the invention are cells having the capacity to differentiate into cells of all three germ layers. Suitable pluripotent cells for use herein include human embryonic stem cells (hESCs) and human induced pluripotent stem (iPS) cells. As used herein, "embryonic stem cells" or "ESCs" mean a pluripotent cell or population of pluripotent cells derived from an inner cell mass of a blastocyst. See Thomson et al., *Science* 282:1145-1147 (1998). These cells express Oct-4, SSEA-3, SSEA-4, TRA-1-60 and TRA-1-81. Pluripotent stem cells appear as compact colonies comprising cells having a high nucleus to cytoplasm ratio and prominent nucleolus. ESCs are commercially available from sources such as WiCell Research Institute (Madison, Wis.). As used herein, "induced pluripotent stem cells" or "iPS cells" mean a pluripotent cell or population of pluripotent cells that may vary with respect to their differentiated somatic cell of origin, that may vary with respect to a specific set of potency-determining factors and that may vary with respect to culture conditions used to isolate them, but nonetheless are substantially genetically identical to their respective differentiated somatic cell of origin and display characteristics similar to higher potency cells, such as ESCs, as described herein. See, e.g., Yu et al., *Science* 318:1917-1920 (2007).

Induced pluripotent stem cells exhibit morphological properties (e.g., round shape, large nucleoli and scant cytoplasm) and growth properties (e.g., doubling time of about seventeen to eighteen hours) akin to ESCs. In addition, iPS cells express pluripotent cell-specific markers (e.g., Oct-4, SSEA-3, SSEA-4, Tra-1-60 or Tra-1-81, but not SSEA-1). Induced pluripotent stem cells, however, are not immediumtely derived from embryos. As used herein, "not immediumtely derived from embryos" means that the starting cell type for producing iPS cells is a non-pluripotent cell, such as a multipotent cell or terminally differentiated cell, such as somatic cells obtained from a post-natal individual.

Human iPS cells can be used according to a method described herein to obtain AECs having the genetic complement of a particular human subject. For example, it may be advantageous to obtain AECs that exhibit one or more specific phenotypes associated with or resulting from a particular disease or disorder of the particular mammalian subject. In such cases, iPS cells are obtained by reprogramming a somatic cell of a particular human subject according to methods known in the art. See, for example, Yu et al., *Science* 324(5928):797-801 (2009); Chen et al., *Nat. Methods* 8(5):424-9 (2011); Ebert et al., *Nature* 457(7227):277-80 (2009); Howden et al., *Proc. Natl. Acad. Sci. U.S.A.* 108(16):6537-42 (2011). Induced pluripotent stem cell-derived AECs allow modeling of drug responses in tissue constructs that recapitulate vascular tissues in an individual having, for example, a particular disease. Even the safest drugs may cause adverse reactions in certain individuals with a specific genetic background or environmental history. Accordingly, human subject specific iPS cell-derived AECs are useful to identify genetic factors and epigenetic influences that contribute to variable drug responses.

Subject-specific somatic cells for reprogramming into iPS cells can be obtained or isolated from a target tissue of interest by biopsy or other tissue sampling methods. In some cases, subject-specific cells are manipulated in vitro prior to use in a three-dimensional hydrogel-based tissue construct of the invention. For example, subject-specific cells can be expanded, differentiated, genetically modified, contacted to polypeptides, nucleic acids, or other factors, cryo-preserved, or otherwise modified prior to introduction to a three-dimensional tissue construct.

Defined medium and substrate conditions for culturing pluripotent stem cells, as used in the methods described herein, are well known in the art. In some cases, pluripotent stem cells to be differentiated according to the methods disclosed herein are cultured in mTESR-1® medium (StemCell Technologies, Inc., Vancouver, British Columbia.), or Essential 8® medium (Life Technologies, Inc.) on a MATRIGEL™ substrate (BD Biosciences, N.J.) according to the manufacturer's protocol or on a Corning® Synthemax surface.

Preferably, human pluripotent stem cells (e.g., human ESCs or iPS cells) are cultured in the absence of a feeder layer (e.g., a fibroblast feeder layer), a conditioned medium, or a culture medium comprising poorly defined or undefined components. As used herein, the terms "chemically defined medium" and "chemically defined culture medium" also refer to a culture medium containing formulations of fully disclosed or identifiable ingredients, the precise quantities of which are known or identifiable and can be controlled individually. As such, a culture medium is not chemically defined if (1) the chemical and structural identity of all medium ingredients is not known, (2) the medium contains unknown quantities of any ingredients, or (3) both. Standardizing culture conditions by using a chemically defined culture medium minimizes the potential for lot-to-lot or batch-to-batch variations in materials to which the cells are exposed during cell culture. Accordingly, the effects of various differentiation factors are more predictable when added to cells and tissues cultured under chemically defined conditions. As used herein, the term "serum-free" refers to cell culture materials that do not contain serum or serum replacement, or that contains essentially no serum or serum replacement. For example, an essentially serum-free medium can contain less than about 1%, 0.9%, 0.8%, 0.7%, 0.6%, 0.5%, 0.4%, 0.3%, 0.2%, or 0.1% serum. "Serum free" also refers to culture components free of serum obtained from animal (e.g., fetal bovine) blood or animal-derived materials, which is important to reduce or eliminate the potential for cross-species viral or prion transmission. For avoidance of doubt, serum-containing medium is not chemically defined.

The methods provided herein produce isolated populations of pluripotent stem cell-derived AECs, where the isolated population is a substantially pure population of AECs. As used herein, "isolating" and "isolated" refer to separating, selecting, or enriching for a cell type of interest or subpopulation of cells from surrounding, neighboring, or contaminating cells or from cells of another type. As used herein, the term "substantially pure" refers to a population of cells that is at least about 80% (e.g., at least about 80%, 82%, 83%, 85%, 90%, 95%, 96%, 97%, 98%, 99% or more) pure, with respect to AECs making up a total cell population. In other words, the term "substantially pure" refers to a population of AECs of the present invention that contains at least about 80% (e.g., at least about 80%, 82%, 83%, 85%, 90%, 95%, 96%, 97%, 98%, 99% or more) of AECs when directing differentiation to obtain cells of the arterial endothelial cell lineage. The term "substantially pure" also refers to a population of AECs of the present invention that contains fewer than about 20%, about 10%, or about 5% of non-AECs in an isolated population prior to any enrichment, expansion step, or differentiation step. In some cases, a substantially pure isolated population of AECs generated according to a method provided herein is at least about 95% (e.g., at least about 95%, 96%, 97%, 98%, 99%) pure with respect to AECs making up a total cell population.

An important difference between arterial endothelial cells produced from iPS cells from a specific individual and primary arterial endothelial cells isolated from that same individual is that the iPS cell-derived cells are infinitely scalable and are capable of exceeding the Hayflick limit (a certain number of cell divisions). As used herein, the term "Hayflick limit" refers to a finite number of population doublings in vitro before a cell can no longer proliferate and enters senescence (Hayflick L. *Exp Cell Res* 37:614-36, 1965). While the inherent self-renewal capacity of primary cultured arterial endothelial cells is limited, an almost inexhaustible supply of arterial endothelial cells can be obtained according to the methods provided herein from a single source (e.g., a somatic cell of an individual). Accordingly, in an embodiment of the invention, the AECs are capable of expansion within the tissue culture laboratory such that the numbers of cells obtained is sufficient to treat more than one patient and, in the preferred embodiment, are capable of cell banking.

In some embodiments, the proportion of arterial endothelial cells in a population of cells obtained in the described methods is enriched using a cell separation, cell sorting, or enrichment method, e.g., fluorescence activated cell sorting (FACS), enzyme-linked immunosorbent assay (ELISA), magnetic beads, magnetic activated cell sorting (MACS), laser-targeted ablation of non-endothelial cells, and combinations thereof. Preferably, FACS is used to identify and separate cells based on cell-surface antigen expression.

The methods of the present invention provide scalable, inexpensive, and reproducible generation of human AECs. For instance, after obtaining a cell population comprising human AECs according to a method described herein, the human AEC population can be expanded in a culture medium appropriate for proliferating human AECs including, without limitation, Human Endothelial Serum-Free Medium (Life Technologies, Cat. No. 11111-044), EGM-2 (Lonza, Cat. No. CC-3162), and Endothelial Cell Culture Medium (BD Biosciences, Cat. No. 355054).

TABLE 1

| Medium Name | Protocol Step | Chemically Defined Components |
|---|---|---|
| E8 | | DMEM/F12 medium + L-ascorbic acid-2-phosphate magnesium (64 mg/l); sodium selenium (14 μg/l); human FGF2 (100 μg/l); insulin (20 mg/l); NaHCO$_3$ (543 mg/l); Transferrin (10.7 mg/l); and TGFβ1 (2 μg/l) |
| E8BAC | Human pluripotent stem cells to mesodermal cells | E8 medium + BMP4 (5 μg/l); Activin A (25 μg/l); and CHIR99021 (1 μM) |
| E7 | | DMEM/F12 medium + L-ascorbic acid-2-phosphate magnesium (64 mg/l); sodium selenium (14 μg/l); human FGF2 (100 μg/l); insulin (20 mg/l); NaHCO$_3$ (543 mg/l); and Transferrin (10.7 mg/l) |
| E7BVi | | E7 medium + VEGFA (50 μg/l); BMP4 (50 μg/l); and SB431542 (5 μM) |
| E7Bi | | E7 medium + BMP4 (50 μg/l); and SB431542 (5 μM) |
| E7Vi | | E7 medium + VEGFA (50 μg/l); and SB431542 (5 μM) |
| E7V | | E6 medium + FGF2 (100 ng/ml); and 50 ng/ml VEGFA |
| E6 | | DMEM/F12 medium + L-ascorbic acid-2-phosphate magnesium (64 mg/l); sodium selenium (14 μg/l); insulin (20 mg/l); NaHCO$_3$ (543 mg/l); and transferrin (10.7 mg/l) |
| E6FVB | | E6 medium + human FGF2 (100 μg/l); VEGFA (50 μg/l); and BMP4 (50 μg/l) |
| E6V | | E6 medium + VEGFA (50 μg/l) |
| E5 | | DMEM/F12 medium + L-ascorbic acid-2-phosphate magnesium (64 mg/l); sodium selenium (14 μg/l); NaHCO$_3$ (543 mg/l); and transferrin (10.7 mg/l) |
| FVIRL | Differentiating pluripotent stem cell-derived mesodermal cells into arterial endothelial cells | E5 medium + Human FGF2 (100 μg/l) VEGF-165 (50 μg/l) SB431542 (10 μM) RESV (5 μM) L-690,330 (10 μM) |
| FVIRLW | | FVIRL + WNT3A (100 ng/ml) |
| FVIRL-5 | | E5 medium + Human FGF2 (100 μg/l); VEGF-165 (50 μg/l); SB431542 (10 μM); RESV (5 μM); and L-690,330 (5 μM) |
| FVIRL-5-I | | FVIRL-5 + insulin (20 mg/l) |
| FVIRL-5-W | | FVIRL-5 + WNT3A (50 ng/ml) |
| FVIRL-5-BB | | FVIRL-5 + PDGF-BB (100 ng/ml) |
| FVIR | Maintaining and expanding arterial endothelial cells | E5 medium + Human FGF2 (100 μg/l); VEGF-165 (50 μg/l); SB431542 (10 μM); and RESV (5 μM) |
| FVIL | | E5 medium + Human FGF2 (100 μg/l); VEGF-165 (50 μg/l); SB431542 (10 μM); and L-690,330 (10 μM) |
| FVIW | | E5 medium + Human FGF2 (100 μg/l); VEGF-165 (50 μg/l); SB431542 (10 μM); and WNT3A (100 ng/ml) |
| FVB | | E5 medium + Human FGF2 (100 μg/l); VEGF-165 (50 μg/l); and BMP4 (50 μg/l) |

TABLE 1-continued

Chemically Defined Culture Medium Components

| Medium Name | Protocol Step | Chemically Defined Components |
|---|---|---|
| FVI | | E5 medium + Human FGF2 (100 µg/l); VEGF-165 (50 µg/l); and SB431542 (10 µM) |
| FV | | E5 medium + Human FGF2 (100 µg/l) VEGF-165 (50 µg/l) |
| BVIn | Differentiating pluripotent stem cell-derived mesodermal cells into endothelial cells | E5 medium + BMP4 (50 µg/l); VEGF-165 (50 µg/l) Insulin (20 mg/l) |
| VI | | E5 medium + VEGF-165 (50 µg/l) SB431542 (5 µM) |
| Control | | E5 medium Human FGF2 (100 µg/l) SB431542 (10 µM) |
| Control + VEGF | | Control medium + VEGF-165 (50 ng/ml) |
| Control + RESV | | Control medium + RESV (5 µM) |
| Control + WNT3A | | Control medium + WNT3A (50 ng/ml) |

In another aspect, provided herein are therapeutic compositions including arterial endothelial cells obtained according to methods provided herein and methods of using them for the treatment of subjects.

In a further aspect, therefore, the present invention provides methods and compositions for cell transplantation, cell replenishment, and cell or tissue replacement and enhancing vasculogenesis. The method can comprise providing to a subject in need thereof a therapeutically effective amount of arterial endothelial cells derived according to a methods provided herein, whereby providing arterial endothelial cells treats the subject. Disorders requiring cell or tissue replacement and improving vasculogenesis include, without limitation, myocardial and peripheral vascular ischemia, other peripheral artery diseases, myocardial infarction (MI), stroke, and diabetic neuropathy, and any other disorder or disease for which the stricken individual would benefit from angiogenic regenerative medicine. Preferred individual subjects according to the present invention are mammals including, without limitation, humans and non-human primates, as well as canines, felines, ovines, porcines, equines, and bovines. In some cases, a substantially pure population of arterial endothelial cells is obtained using a pluripotent cell (e.g., induced pluripotent stem cell) of the subject in need of treatment. However, a substantially pure population of arterial endothelial cells also can be obtained using pluripotent stem cells of, preferably, a syngeneic or allogeneic donor. Less preferably, a xenogeneic donor is used.

In another aspect, this document provides methods for improving vascular perfusion. In particular, provided herein is a method for treating peripheral arterial disease in a patient, where the method comprises administering to the patient a therapeutic dose of arterial endothelial cells obtained as described herein. As used herein, the term "peripheral arterial disease" refers to acute and chronic critical limb ischemia and ischemia associated with a disorder affecting blood supply to tissues such as diabetes or arteriosclerosis. In some cases, arterial endothelial cells obtained according to the methods provided herein are directly injected into the patient subject to treat the peripheral artery disease. Without being bound to any particular theory, it is expected that such arterial endothelial cells would be therapeutic for limb ischemia (e.g., ischemia associated with diabetes or cardiac infarcts) and more beneficial than treatment with a non-arterial endothelial cell. In exemplary embodiments, in vitro-derived AECs are patient specific or HLA-matched cells for transplantation to a patient to treat ischemia. For example, AECs can be derived from iPS cells obtained by reprogramming a somatic cell of the patient to pluripotency and then using the iPS cells according to a method provided herein to obtain a population comprising patient specific AECs. AECs obtained from patient-derived iPS cells can be administered to the patient in any pharmaceutically acceptable carrier, buffer, or excipient. The route of administration of the cells to the patient may be via intravenous or intramuscular injection. In some cases, for example, AECs derived from human pluripotent stem cells are resuspended in a saline solution and injected intramuscularly at one or more sites of limb ischemia.

Any appropriate dosage can be used for a therapeutic method provided herein. The cell dose will depend on the extent and severity of the ischemia but a preferred range is from about $1 \times 10^8$ cells/patient to about $1 \times 10^{10}$ cells/patient per dose. In some cases, AECs obtained as described herein are co-administered to a subject with other cell types including, for example, smooth muscle cells (e.g., vascular smooth muscle cells).

After administering the cells into the subject, the effect of the treatment method may be evaluated, if desired, using any appropriate method known to practitioners in the art. The treatment may be repeated as needed or required. Following treatment according to the methods provided herein, the treated subject can be monitored for any positive or negative changes in limb ischemia. In a preferred embodiment, a therapeutic increase in blood supply to an ischemic tissue is a result of an increase in blood vessel formation (angiogenesis) following implantation of the said cells. The methods provided herein provide cells that are pro-angiogenic following transplantation. In some cases, positive changes include, without limitation, increased blood supply to ischemic tissue, increased amputation-free survival, decreased need for limb amputation, decreased limb pain when the subject is a rest, and improvements in pain-free walking (e.g., pain-free walking over greater distances).

In another aspect, AECs obtained according to the methods provided herein are useful for methods in which the production of nitric oxide (NO) has a therapeutic or preventative benefit for a subject. For example, provided herein is a method for administering AECs to a subject as a method for providing NO to the subject, whereby administering the AECs treats or prevents atherosclerosis, reduces DNA damage, and/or relaxes smooth muscle cells to improve blood vessel function.

Administration of a therapeutically effective amount of AECs into the recipient subject is generally effected using methods well known in the art, and usually involves directly injecting or otherwise introducing a therapeutically effective AECs into the subject using clinical tools known to those skilled in the art (e.g., U.S. Pat. Nos. 6,447,765; 6,383,481; 6,143,292; and 6,326,198). For example, introduction of AECs of the present invention can be effected locally or systemically via intravascular administration, such as intravenous, intramuscular, or intra-arterial administration, intraperitoneal administration, and the like. Cells can be injected into an infusion bag (e.g., Fenwal infusion bag (Fenwal, Inc.)) using sterile syringes or other sterile transfer mechanisms. The cells can then be immediately infused via IV administration over a period of time, such as 15 minutes, into a free flow IV line into the patient. In some embodiments, additional reagents such as buffers or salts are provided to the recipient subject concurrently with the cells.

In exemplary embodiments, AECs of the present invention are provided to the subject as a pharmaceutical composition comprising the cells and one or more pharmaceutically acceptable carriers, buffers, or excipients. The pharmaceutical composition for administration must be formulated, produced, and stored according to standard methods that provide proper sterility and stability. A pharmaceutical composition of the present invention may also comprise one or more growth factors or cytokines (e.g., angiogenic cytokines) that promote the survival or engraftment of transplanted cells, promote angiogenesis, modulate the composition of extracellular or interstitial matrix, and/or recruit other cell types to the site of transplantation.

In another aspect, provided herein is a method for producing an engineered blood vessel using arterial endothelial cells obtained according to a method provided herein. AECs also can be used as raw materials, optionally in combination with additional cell populations, for creating blood vessels in vitro or in vivo. Such vessels will be useful, for example, in revascularizing damaged tissues and in treating peripheral artery disease. Engraftment of and vasculogenesis by externally injected cells has been shown by in vivo animal studies. See, for example, Kim et al., *J. Am. Coll. Cardiol.* 56:593-607 (2010).

Also provided herein are methods of using in vitro-derived AECs for in vitro blood vessel formation and for vascularization of engineered tissues that lack a vascular network such as engineered cardiac muscle tissue or heart. For example, AECs are useful in methods for producing tissue-engineered vascular grafts for clinical applications such as replacing diseased vessels. In some cases it will be advantageous to use patient-specific or HLA matched AECs for methods of treating a patient with a tissue-engineered vascular graft, an in vitro-produced blood vessels, or other vascularized engineered tissue. As described above, AECs can be derived from iPS cells obtained by reprogramming a somatic cell of the patient to pluripotency and then using the iPS cells according to a method provided herein to obtain a population comprising patient-specific AECs. In some cases, it will be advantageous to co-culture the AECs with other cell types such as vascular smooth muscle cells (VSMC) to obtain a vascularized engineered tissue construct such as an engineered blood vessel for clinical application such as bypass surgery. Preferably, AECs are combined with patient-specific in vitro-derived vascular smooth muscle cells for these methods. Vascular smooth muscle cells are positive for expression of ACTA2, TAGLN, MYH11, and ELN, but CD31 negative. In other cases, AECs can be co-cultured with cardiomyocytes to form a vascularized cardiac tissue patch useful for improving cardiac function.

In a further aspect, provided herein is a method of in vitro screening of an agent. For example, provided herein are methods of using in vitro-derived arterial endothelial cells for high throughput screening of candidate. For example, AECs obtained as described herein can be screened to identify agents that decrease leukocyte adhesion as a potential therapeutic or preventative for atherosclerosis. Screening methods can comprise or consist essentially of (a) contacting a test agent to an arterial endothelial cell or population of arterial endothelial cells as described herein; and (b) detecting an effect of the agent on the cell or cells (e.g., decreased leukocyte adhesion to AECs). In some cases, screening methods include screening candidate compounds to identify test agents that promote the development of vascular tissue. In other cases, candidate compounds can be screened for toxicity to human arterial endothelial cells or vascular tissue. In some cases, detecting comprises detecting at least one positive or negative effect of the agent on morphology or life span of cells, whereby an agent that increases or reduces the life span of the cells or has a positive or negative impact on the morphology of the cells is identified as having an effect on human arterial endothelial cells or vascular tissues. In some cases, detecting comprises performing a method selected from the group consisting of adhesion assays, RNA sequencing, gene expression profiling, transcriptome analysis, metabolome analysis, detecting reporter or sensor, protein expression profiling, Förster resonance energy transfer (FRET), metabolic profiling, and microdialysis. The agent can be screened for an effect on gene expression, and detecting can comprise assaying for differential gene expression relative to an uncontacted cell or cell population.

In exemplary embodiments, detecting and/or measuring a positive or negative change in a level of expression of at least one gene following exposure (e.g., contacting) of a test compound to arterial endothelial cells comprises whole transcriptome analysis using, for example, RNA sequencing. In such cases, gene expression is calculated using, for example, data processing software programs such as Light Cycle, RSEM (RNA-seq by Expectation-Maximization), Excel, and Prism. See Stewart et al., *PLoS Comput. Biol.* 9:e1002936 (2013). Where appropriate, statistical comparisons can be made using ANOVA analyses, analysis of variance with Bonferroni correction, or two-tailed Student's t-test, where values are determined to be significant at $P<0.05$. Any appropriate method can be used to isolate RNA or protein from neural constructs. For example, total RNA can be isolated and reverse transcribed to obtain cDNA for sequencing.

Test compounds can be dissolved in a solvent such as, for example, dimethyl sulfoxide (DMSO) prior to contacting to AECs provided herein. In some cases, identifying agents comprises analyzing the contacted AECs for positive or negative changes in biological activities including, without limitation, gene expression, protein expression, cell viability, and cell proliferation. For example, microarray methods can be used to analyze gene expression profiles prior to, during, or following contacting the plurality of test compounds to the AECs. In some cases, a method of the present invention further comprises additional analyses such as metabolic assays and protein expression profiling.

Compositions

In another aspect, provided herein are preparations of AECs. For example, provided herein are AECs, substantially purified populations of AECs, pharmaceutical preparations comprising AECs, and cryopreserved preparations of the AECs. The AECs described herein may be substantially free of at least one protein, molecule, or other impurity that is found in its natural environment (e.g., "isolated"). The AECs may be mammalian, including, human AECs. The invention also provides human AECs, a substantially purified population of human AECs, pharmaceutical preparations comprising human AECs, and cryopreserved preparations of the human AECs. The preparation may be a preparation comprising human embryonic stem cell-derived AECs, human iPS cell-derived AECs, and substantially purified (with respect to non-AECs) preparations comprising differentiated pluripotent stem cell-derived AECs.

Cell preparations provided herein are useful for various in vitro and in vivo applications such as engineering new blood vessels, endothelial cell transplantation into the heart for myocardial regeneration, induction of angiogenesis for treatment of regional ischemia, and screening for drugs affecting vasculature such as angiogenesis inhibition to slow cancer progression. Since most vascular disease occurs in arteries (Go et al., 2014), arterial cells are extremely valuable for disease modeling, as they can be used for investigating how arterial endothelial cells are activated, and for screening drugs to prevent the activation, which will facilitate understanding and curing atherosclerosis. Because it has been very difficult to obtain AECs, these cells have been largely omitted from tissue-engineered vascular grafts and pre-vascularization of tissue transplants (Bae et al., 2012; Campbell and Campbell, 2007), which could contribute to poor clinical outcome. The disclosed methods facilitate production and use of AEC populations.

Preparations comprising AEC cells useful for clinical applications must be obtained in accordance with regulations imposed by governmental agencies such as the U.S. Food and Drug Administration. Accordingly, in exemplary embodiments, the methods provided herein are conducted in accordance with Good Manufacturing Practices (GMPs), Good Tissue Practices (GTPs), and Good Laboratory Practices (GLPs). Reagents comprising animal derived components are not used, and all reagents are purchased from sources that are GMP-compliant. In the context of clinical manufacturing of a cell therapy product, such as in vitro populations of human arterial endothelial cells, GTPs govern donor consent, traceability, and infectious disease screening, whereas the GMP is relevant to the facility, processes, testing, and practices to produce a consistently safe and effective product for human use. See Lu et al. *Stem Cells* 27: 2126-2135 (2009). Where appropriate, oversight of patient protocols by agencies and institutional panels is envisioned to ensure that informed consent is obtained; safety, bioactivity, appropriate dosage, and efficacy of products are studied in phases; results are statistically significant; and ethical guidelines are followed.

In another aspect, provided herein is a culture medium or a culture system comprising a culture medium for differentiating human pluripotent stem cell-derived mesodermal cells into AECs, where the culture medium comprises or consists essentially of a Fibroblast Growth Factor (FGF), a vascular endothelial growth factor (VEGF), an inhibitor of TGF-beta signaling (e.g., SB431542), a Notch agonist (e.g., Resveratrol (RESV)), and an inhibitor of inositol monophosphatase. In exemplary embodiments, the culture medium comprises or consists essentially of E5 medium supplemented with human FGF2 (100 µg/l), VEGF-165 (50 µg/l), SB431542 (10 µM), RESV (5 µM), and L-690,330 (10 µM). Such a culture medium does not comprise insulin.

Articles of Manufacture

The invention also provides a kit for differentiating human pluripotent stem cells into AECs, comprising (i) a first culture medium suitable for differentiation of human pluripotent stem cells into mesodermal cells; (ii) a second culture medium suitable for differentiation of pluripotent stem cell-derived mesodermal cells into arterial endothelial cells; and (iii) instructions describing a method for differentiating human pluripotent stem cells into $CD31^+/CD144^+/CD41^-/CD45^-$ arterial endothelial cells, the method employing the first culture medium and the second culture medium.

Unless defined otherwise, all technical and scientific terms used herein have the same meaning as commonly understood by one of ordinary skill in the art to which the invention belongs. Although any methods and materials similar to or equivalent to those described herein can be used in the practice or testing of the present invention, the preferred methods and materials are described herein.

In the specification and in the claims, the terms "including" and "comprising" are open-ended terms and should be interpreted to mean "including, but not limited to . . . ." These terms encompass the more restrictive terms "consisting essentially of" and "consisting of." As used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising," "including," "characterized by," and "having" can be used interchangeably.

As used herein, "a medium consisting essentially of" means a medium that contains the specified ingredients and those that do not materially affect its basic characteristics.

As used herein, "effective amount" means an amount of an agent sufficient to evoke a specified cellular effect according to the present invention.

As used herein, "about" means within 5% of a stated concentration range, density, temperature, or time frame.

The invention will be more fully understood upon consideration of the following non-limiting Examples. It is specifically contemplated that the methods disclosed are suited for pluripotent stem cells generally. All papers and patents disclosed herein are hereby incorporated by reference as if set forth in their entirety.

EXAMPLES

Figures 2A, 2B, 2C, 2D, 2E, 2F, 2G, 2H:
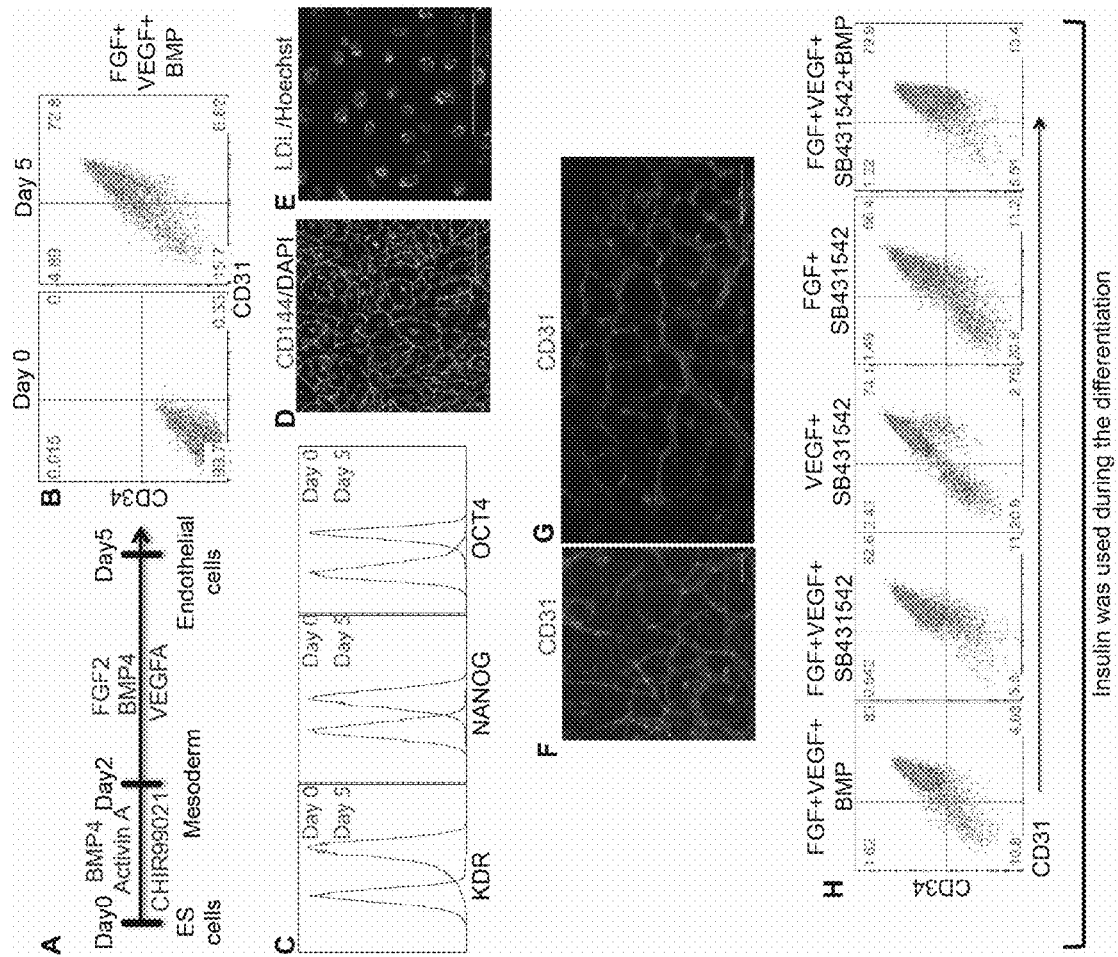
FIG. 2A provides a schematic representation of a protocol for generating arterial endothelial cells from human pluripotent stem cells using a chemically-defined medium listed in Table 1. Human embryonic stem (ES) cells were first differentiated into mesoderm cells using E8BAC medium. E6 medium supplemented with growth factors or small molecules (E6FVB) was then used to induce mesoderm cells to differentiate into endothelial cells.
FIG. 2B is flow cytometric data for of CD31 and CD34 expression at day 0 (undifferentiated pluripotent state) and at day 5 (differentiated state).
FIG. 2C is flow cytometric data for KDR, NANOG, and OCT4 expression at day 0 and at day 5.
FIG. 2D indicates CD144 expression on purified endothelial cells by immunostaining.
FIG. 2E shows a LDL (low density lipoprotein) uptake assay.
FIG. 2F shows an in vitro MATRIGEL® (BD Biosciences, Falcon®) encapsulation assay.
FIG. 2G shows the results of an in vivo MATRIGEL® gel plug assay for analysis of migration and angiogenesis. Anti-human CD31-specific antibody was used for immunostaining to detect vascular formation in recovered gel plugs.
FIG. 2H shows flow cytometric analysis of CD31 and CD34 expression after five days of differentiation in the indicated combinations of growth factors and small molecules. Insulin was included in each combination. When the differentiation medium included a TGF inhibitor, SB431542 was included at 10 μM.

Example 1—Protocol for Directed Differentiation of Pluripotent Stem Cells into AECs To investigate arterial differentiation, an endothelial cell differentiation protocol was developed using a defined culture medium lacking both serum and bovine serum albumin. Xeno-free pluripotent stem cells were first differentiated into mesoderm cells in a culture medium supplemented with BMP4, Activin-A, and CHIR99021 (E8BAC medium) for two days. Mesoderm cells were then treated with FGF2, VEGFA, and BMP4 for another three days, yielding a 70% $CD31^+/CD34^+$ endothelial cell population (FIGS. 2A-B). Insulin was included in this mesoderm-to-endothelium differentiation medium. Endothelial cell fate was further confirmed by the down-regulation of NANOG and OCT4 (FIG. 2C), the up-regulation of KDR/VEGFR2, the expression of CD144 (CDH5/VE-cadherin) (FIG. 2D), the internalization of LDL (FIG. 2E), and the formation of capillary networks in vitro and in vivo (FIGS. 2F-G). With this protocol, we were able to investigate the effect of individual medium components under completely defined culture conditions (FIG. 2H).

Since cells of the $CD31^+/CD34^+$ endothelial cell population largely failed to express markers of AECs (data not shown), we isolated a population of $CD31^+/CD144^+/CD41^-/CD45^-$ endothelial cells from the aorta-gonad-mesonephros (AGM) region of embryonic mesoderm of a E11.5 day mouse embryo. These cells were isolated from the AGM to identify new factors having capacity to induce arterial differentiation.

Single-cell RNA-Seq was performed for the $CD31^+/CD144^+/CD41^-/CD45^-$ endothelial cells to characterize global gene expression profiles of individual endothelial cells. To distinguish arterial and venous endothelial cell populations, a set of arterial markers (Efnb2, Cxcr4, Dll4, Gja4, Hey1, Jag1, Notch1, Notch4, and Nrp1) and venous markers (Aplnr, Ephb4, Flt4, Nr2f2, and Nrp2) were analyzed using SINGuLAR™ Analysis Toolset. Many of the markers clustered into either the arterial group or venous group, but Aplnr and Notch1 did not cluster with either group (FIG. 1A). This result is consistent with a previous study suggesting that some arteriovenous markers are transiently non-specific (Chong et al., 2011). Based on marker expression, the CD31$^+$/CD144$^+$/CD41$^-$/CD45$^-$ endothelial cells were clustered into five subpopulations (FIG. 1A). The average normalized expression of arterial and venous gene sets within each subpopulation was calculated to distinguish arterial and venous cells (FIG. 1B). Population 1 (P1) was identified as arterial endothelial cells, as it had the highest arterial and the lowest venous marker expression (FIG. 1B). By contrast, Population 3 (P3) had the lowest arterial gene expression (FIG. 1B). Principal component analysis revealed a clear separation between the P1 and P3 cells (FIG. 1C), and 918 genes were determined to be enriched in P1 cells (arterial endothelial cells) (p<0.1, FC>2, TMP>1) compared to P3 cells (see Table 4).

To identify growth factor related genes within the 918 arterial enriched genes, five AmiGo gene ontology data "terms" were combined: growth factor binding (GO: 0019838), growth factor activity (GO:0008083), growth factor receptor binding (GO:0070851), receptor activity (GO:0004872), and receptor binding (GO:0005102). The combined list was then intersected with plasma membrane genes (GO:0005886) to remove non-cell surface genes (FIG. 1D and Tables 2 and 4). Some of the resulting 42 genes were not growth factors or their receptors, but were either upstream or downstream of a growth factor signaling pathway. Some well-known arteriovenous regulators, including VEGFA, Wnt signaling (FZD4, FZD7, FZD10), and Notch signaling (DLL4 and Notch4) were present in these 42 genes (Table 2).

Figures 8A, 8B, 8C, 8D, 8E, 8F, 8G, 8H, 8I, 8J:
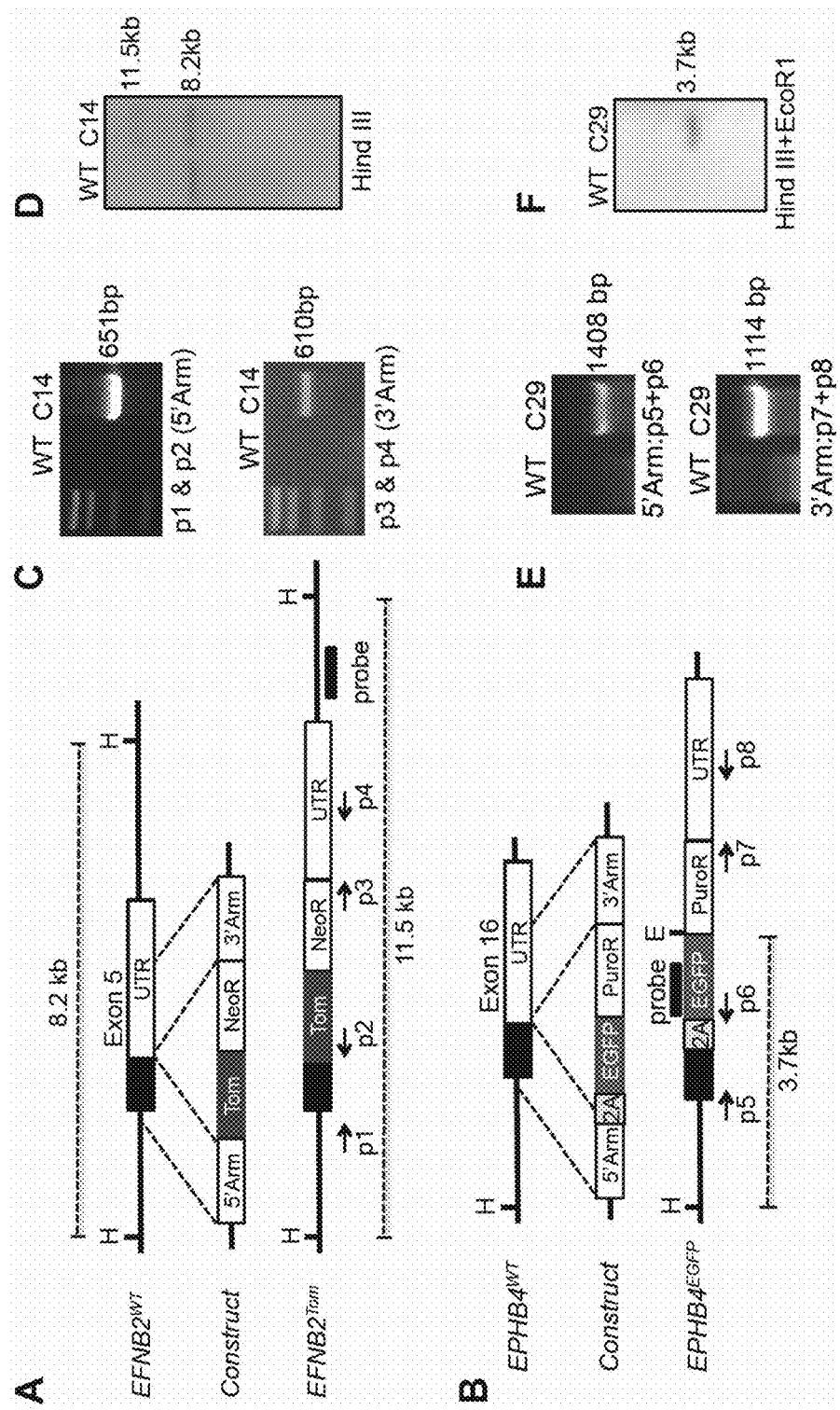
FIGS. 8A-8J present data for the generation and characterization of the reporter cell line. (A) Schematic of wild type and targeted EFNB2-tdTomato allele. H1 ES cells were used for gene targeting. Tom: tdTomato. (B) Schematic of wild type and targeted EPHB4-EGFP allele. (C) Junction PCR of 5' arm and 3' arm of EFNB2-tdTomato alleles. WT: wild type, C14: clone 14 of targeted cells. (D) Southern blot of EFNB2 wild type and knock-in (EFNB2-tdTomato) alleles. (E) Junction PCR of 5' arm and 3' arm of EPHB4-EGFP allele. C29: clone 29 of targeted cells. (F) Southern blot of EPHB4-EGFP allele. (G) qPCR analysis of tdTomato copy number of EFNB2-tdTomato cell line (clone 14). Data are represented as mean±SD. n=3. Con: control samples with one copy of tdTomato. (H) qPCR analysis of EGFP copy number of EFNB2-tdTomato/EPHB4-EGFP cell line (clone 29). Data are represented as mean±SD. n=3. Con: control samples with one copy of EGFP. (I) Comparing of endogenous EFNB2 and EPHB4 gene expression of wild type and reporter cell lines by RT-qPCR. Day 5, differentiation for five days. Data are represented as mean±SD. n=3. (J) Karyotyping of EFNB2-tdTomato/EPHB4-EGFP cell line (clone 29).
Figure 9:
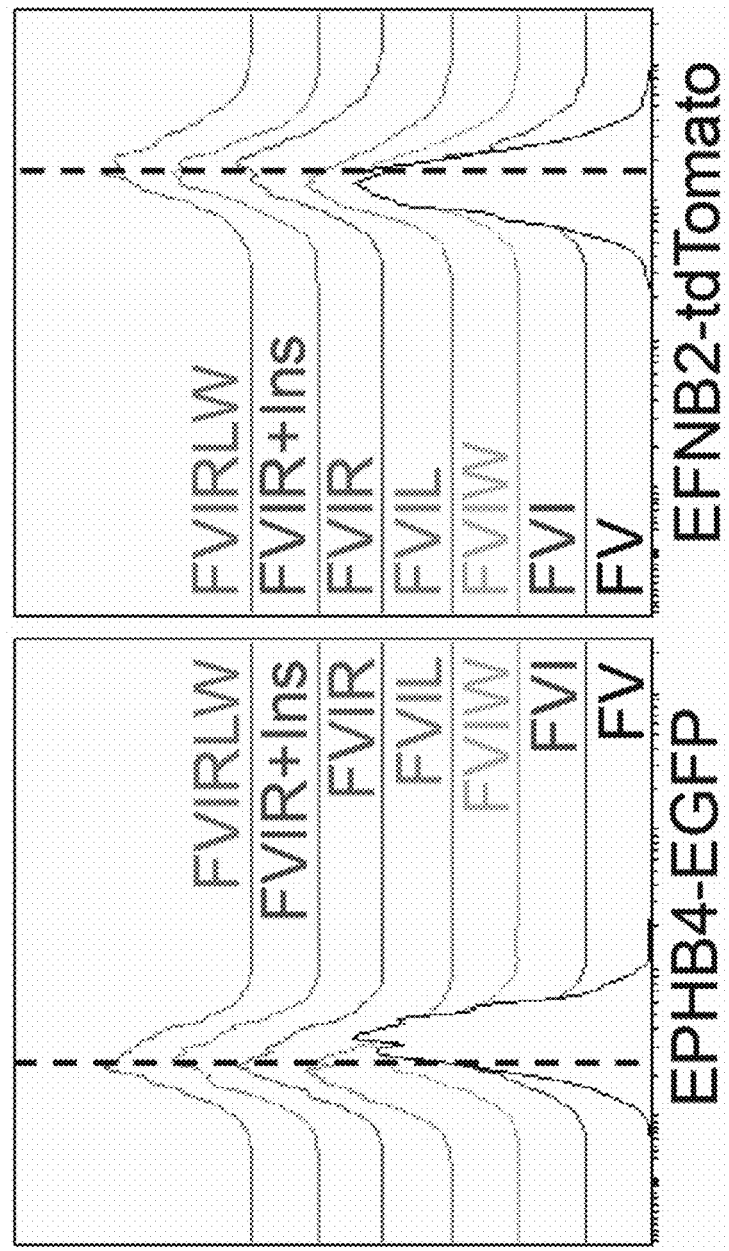
FIG. 9 presents flow cytometric analysis of EFNB2-tdTomato and EPHB4-EGFP expression. Purified AECs were cultured in E5 medium supplemented with growth factors or small molecules for three days. F: 100 ng/ml, V: 50 ng/ml VEGFA, I: 10 µM SB431542, W: 100 ng/ml WNT3A, L: 10 µM L-690,330, R: 5 µM RESV. Ins: 10 µg/ml insulin. Lower EPHB4-EGFP and higher EFNB2-tdTomato expression were observed in cultures with FVIR, FVIR+Ins, and FVIRLW medium.

In order to test candidate factors in human arterial differentiation, we made a dual human ES cell reporter line using clustered regularly interspaced short palindromic repeats (CRISPR (clustered regularly interspaced short palindromic repeats)-Cas9 technology to target EFNB2 (ephrin B2) with tdTomao and EPHB4 (ephrin type B receptor 4) with EGFP (FIGS. 8A-8B). See, e.g., Hou et al., 2013. EFNB2 and EPHB4 are the most characterized embryonic arterial and venous endothelial cell markers, respectively (Wang et al., 1998). Specific targeting of the EFNB2 and EPHB4 loci was confirmed by junction PCR and southern blot (FIGS. 8C-8F). Only single copies of each reporter were integrated into genome (FIGS. 8G-8H), and the endogenous expression of EFNB2 and EPHB4 in the reporter cell line was similar to that in wild type cells (FIG. 8I). Karyotypes were normal after dual targeting (FIG. 8J), and DNA sequencing revealed no CRISPR induced insertions or deletions in the wild type alleles.

Figures 11A, 11B, 11C:
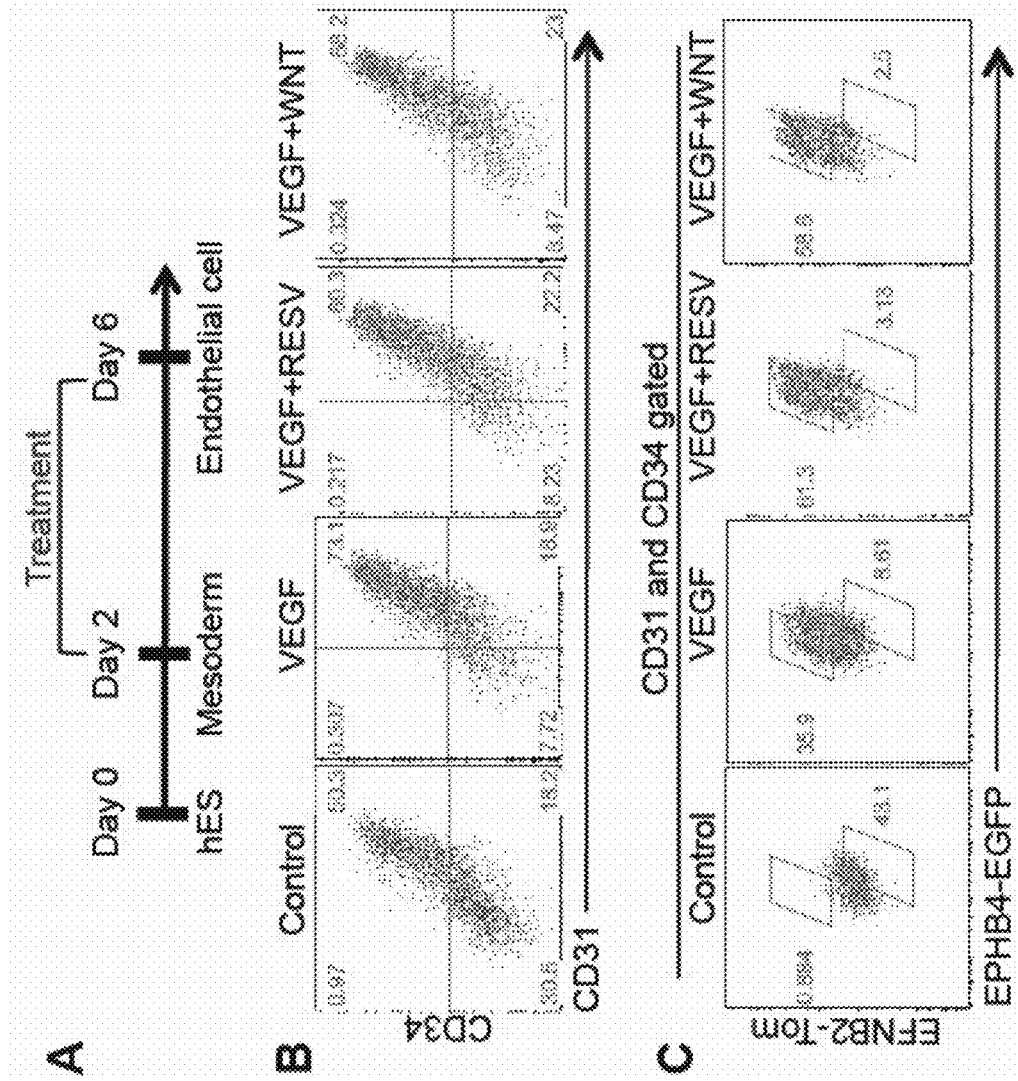
FIGS. 11A-11C present arterial endothelial cell differentiation data. (A) Schematic of arterial endothelial cell differentiation protocol. ES cells were first differentiated into mesoderm cells by E8BAC medium (E8 medium supplemented with 5 ng/ml BMP4, 25 ng/ml Activin A, and 1 µM CHIR99021). E5 (E8 medium minus FGF2, TGFβ1, and insulin) medium supplemented with 100 ng/ml FGF2 and 10 µM SB431542 was then used to induce mesoderm cells to differentiate into endothelial cells. (B) Flow cytometric analysis of CD31 and CD34 expression. E5+100 ng/ml FGF2+10 µM SB431542 medium ("Control") supplemented with 50 ng/ml VEGF, 5 µM RESV (resveratrol, a Notch activator), or 50 ng/ml WNT3A was used to induce mesoderm cells to differentiate into arterial endothelial cells. (C) Flow cytometric analysis of EFNB2-tdTomato and EPHB4-EGFP expression.

We used the EFNB2-tdTomato/EPHB4-EGFP dual reporter cell line to test the function of individual growth factor related genes identified by single-cell RNA-Seq analysis. Consistent with their previously described roles, VEGFA, WNT3A, and RESV (a Notch agonist) all promoted increased arterial specification (FIG. 11).

Figures 3A, 3B, 3C, 3D, 3E, 3F:
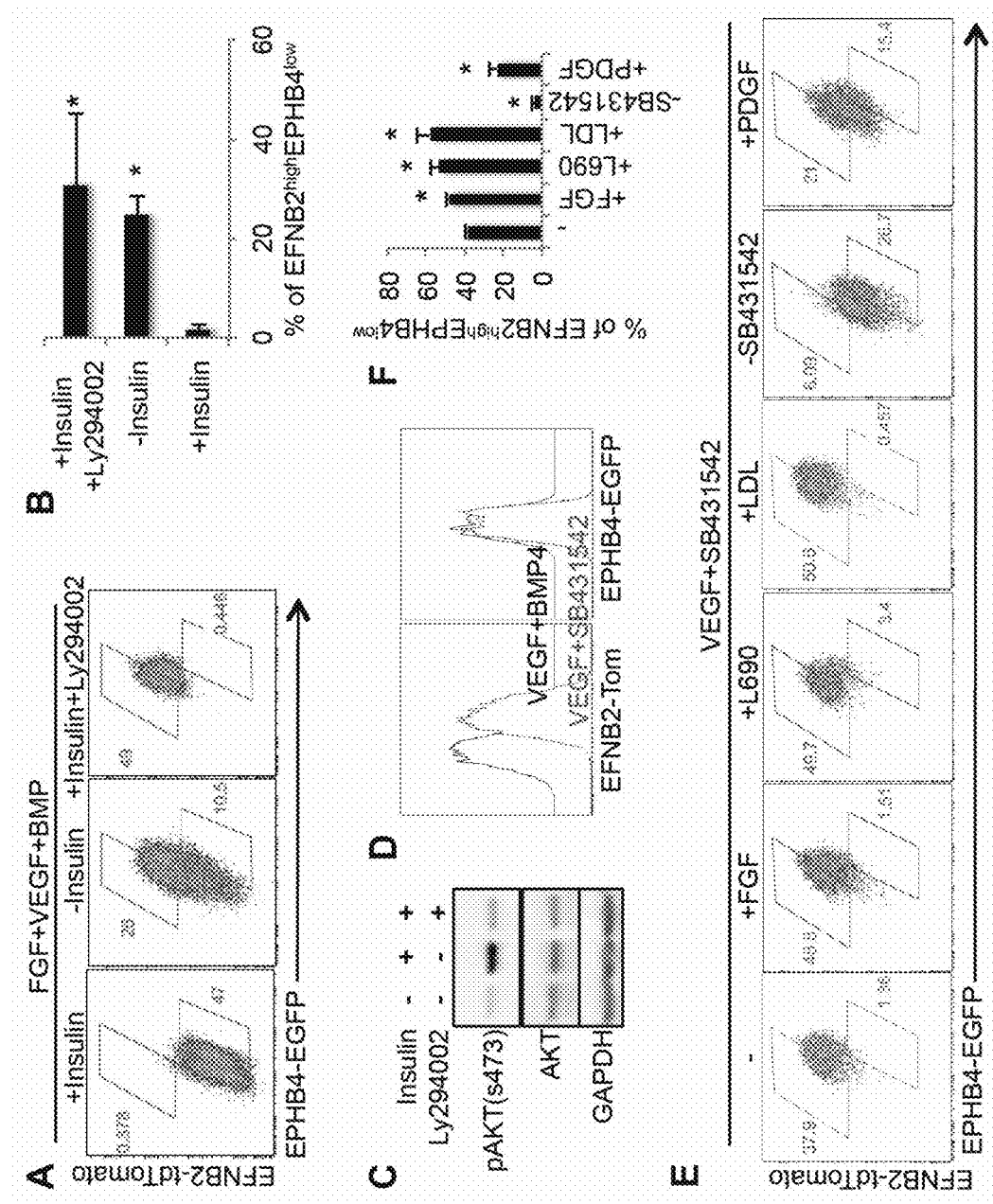
FIGS. 3A-3F present candidate pathways critical for arteriovenous specification. (A) Flow cytometric analysis of EFNB2-tdTomato and EPHB4-EGFP expression on CD31 and CD144 gated endothelial cells. EFNB2-tdTomato/EPHB4-EGFP dual reporter cells (hetero knock-in in H1 cells for each gene) were first differentiated into mesoderm cells by E8BAC medium (E8 medium supplemented with BMP4, Activin-A, and CHIR99021). E5 (E8 medium minus FGF2, TGFβ1, and insulin) medium supplemented with 100 ng/ml FGF2, 50 ng/ml VEGFA, and 50 ng/ml BMP4 was used to induce mesoderm cells to differentiate into endothelial cells from day 2 to day 6. Either Insulin (20 μg/ml) or Ly294002 (16 μM, a PI3K inhibitor) was added to the medium as indicated from day 2 to day 6. (B) Statistics of EFNB2-tdTommato$^{high}$/EPHB4-EGFP$^{low}$ cells. Data are represented as mean±SD. *: P<0.05, n=5. (C) Western blots showing AKT activity. Protein was harvested at day 3. (D) Flow cytometric analysis of EFNB2-tdTomato and EPHB4-EGFP expression on CD31 and CD144 gated endothelial cells. E5 medium supplemented with 50 ng/ml VEGFA, 50 ng/ml BMP4 or 10 μM SB431542 was used to induce mesoderm cells to differentiate into endothelial cells from day 2 to day 6. (E) Flow cytometric analysis of EFNB2-tdTomato and EPHB4-EGFP expression on CD31 and CD144 gated endothelial cells. ES cells were first differentiated into mesoderm cells as mentioned above. E5 medium supplemented with 50 ng/ml VEGFA and 10 μM SB431542 was used as the base medium induce mesoderm cells to differentiate into endothelial cells from day 2 to day 6. Other factors were added to the base medium as indicated. (F) Statistics of EFNB2-tdTomato$^{high}$/EPHB4-EGFP$^{low}$ cells. 5 μM L690, 5 μg/ml LDL, and 100 ng/ml PDGF-BB were used. *: P<0.05, n=3.

We then investigated the other growth factors/signaling pathways during endothelial cell differentiation by adding or removing recombinant proteins/small molecules, such as insulin, as it is widely used in endothelial cell differentiation protocols. Surprisingly, removing insulin after mesoderm formation triggered AEC differentiation, as evidenced by the increased number of EFNB2-tdTomato$^{high}$/EPHB4-EGFP$^{low}$ cells (FIGS. 3A-B). Since insulin is able to activate AKT (Mackenzie and Elliott, 2014), a negative regulator of arteriovenous specification (Hong et al., 2006), we examined AKT activity. Phosphorylated AKT (pAKT) was increased by the presence of insulin, and inhibiting PI3K activity using Ly294002 (a reversible inhibitor of phosphoinositide 3-kinases (PI3Ks)) decreased pAKT (FIG. 3C) and reversed the inhibitory effect of insulin during arterial differentiation (FIGS. 3A-3B). These results demonstrate that the insulin-AKT pathway played a key role in suppressing arterial differentiation.

In addition, we found that the following factors increased arterial endothelial cell differentiation: FGF2, L-690,330 (a inositol monophosphatase inhibitor), and LDL (low-density lipoprotein), as evidenced by the increase of EFNB2-tdTomato$^{high}$/EPHB4-EGFP$^{low}$ cells (FIG. 3F). In contrast, removing SB431542 (a TGF-β receptor inhibitor) or adding PDGF-BB inhibited arterial differentiation (FIGS. 3E-3F).

To further confirm these results, EFNB2-tdTomato$^{high}$/EPHB4-EGFP$^{low}$ putative arterial endothelial cells and EFNB2-tdTomato$^{low}$/EPHB4-EGFP$^{high}$ putative venous endothelial cells were sorted by FACS and analyzed by RT-qPCR. Arterial genes were significantly up-regulated in EFNB2-tdTomato$^{high}$/EPHB4-EGFP$^{low}$ cells. These data demonstrate that FGF, L-690,330, and LDL promote arterial endothelial differentiation of human pluripotent stem cells while insulin, TGF-β, and PDGF inhibit arterial endothelial differentiation.

Figures 4A, 4B, 4C, 4D, 4E, 4F, 4G, 4H:
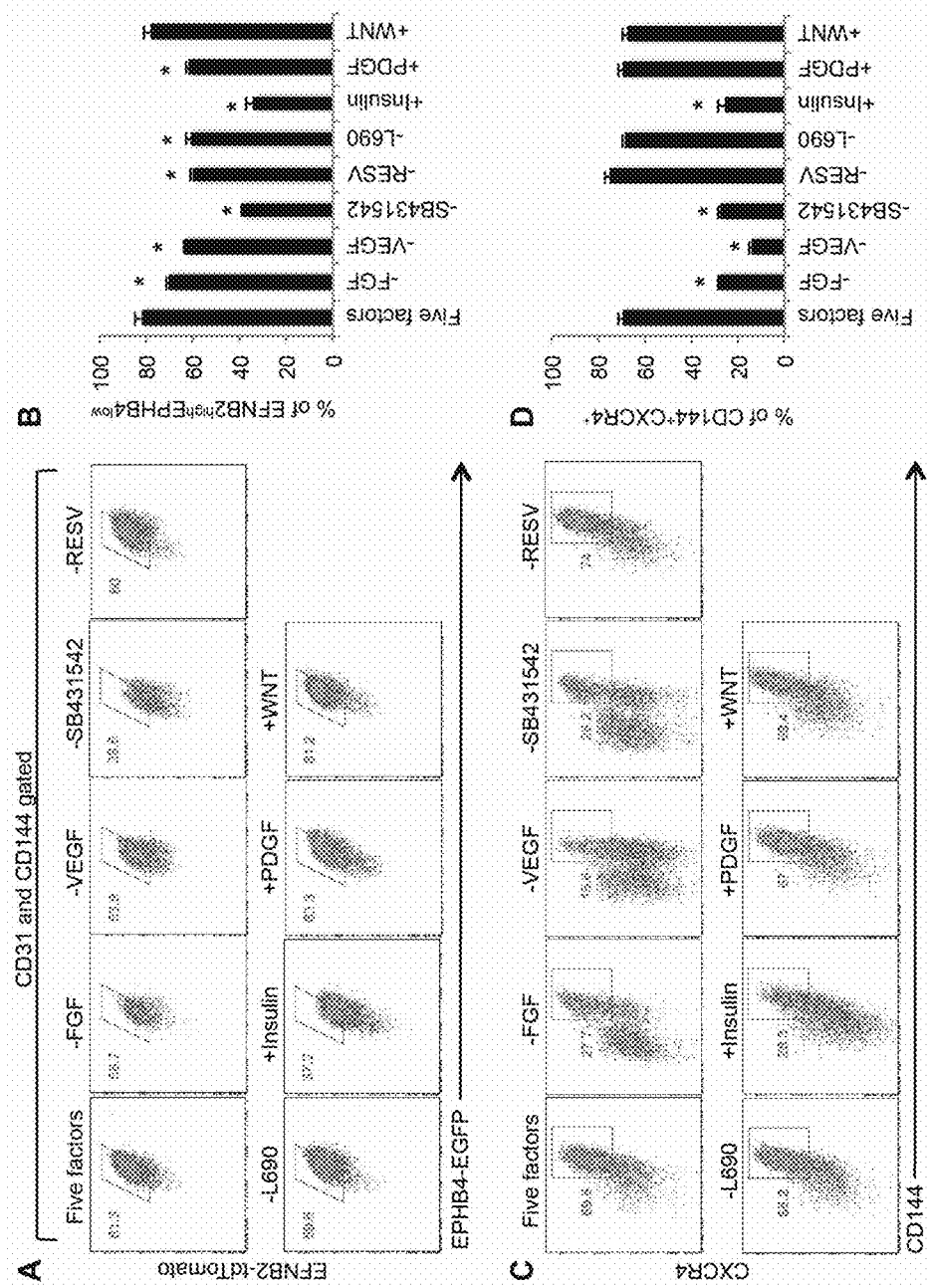
FIGS. 4A-4H present flow cytometric analysis of expression of EphrinB2 and Ephrin Type B Receptor 4 reporter constructs (EFNB2-tdTomato and EPHB4-EGFP) on CD31− and CD144-gated endothelial cells obtained after differentiation in various medium, as described.

To further improve arterial differentiation, we examined combinations of individual factors. Arterial endothelial cell differentiation was greatly improved by combining FGF, VEGFA, SB431542, RESV, and L-690,330 ("five factors") in a chemically defined medium ('FVIRL medium" in Table 1; see also FIGS. 4A-4B) when compared to the differentiation observed when single factors were employed. Removing FGF, VEGF, SB431542, or RESV individually led to a decrease of EFNB2-tdTomato$^{high}$/EPHB4-EGFP$^{low}$ cells (FIGS. 4A-4B). Two other arterial markers, CXCR4 and DLL4, were similarly decreased upon removal of FGF, VEGF, SB431542, or RESV (FIGS. 4C-4F). However, when RESV or L-690,330 was removed, or when PDGF as added, fewer EFNB2-tdTomato$^{high}$/EPHB4-EGFP$^{low}$ putative arterial endothelial cells were obtained, but no reduction of CD144$^+$CXCR4$^+$ and CD144$^+$DLL4$^+$ cells was observed (FIGS. 4C-4F). Although as a single factor WNT3A promoted arterial differentiation, exogenous WNT3A did not further increase arterial differentiation in the context of the other five factors (FIGS. 4A-4F, FIG. 9).

Figures 5A, 5B, 5C, 5D, 5E, 5F, 5G:
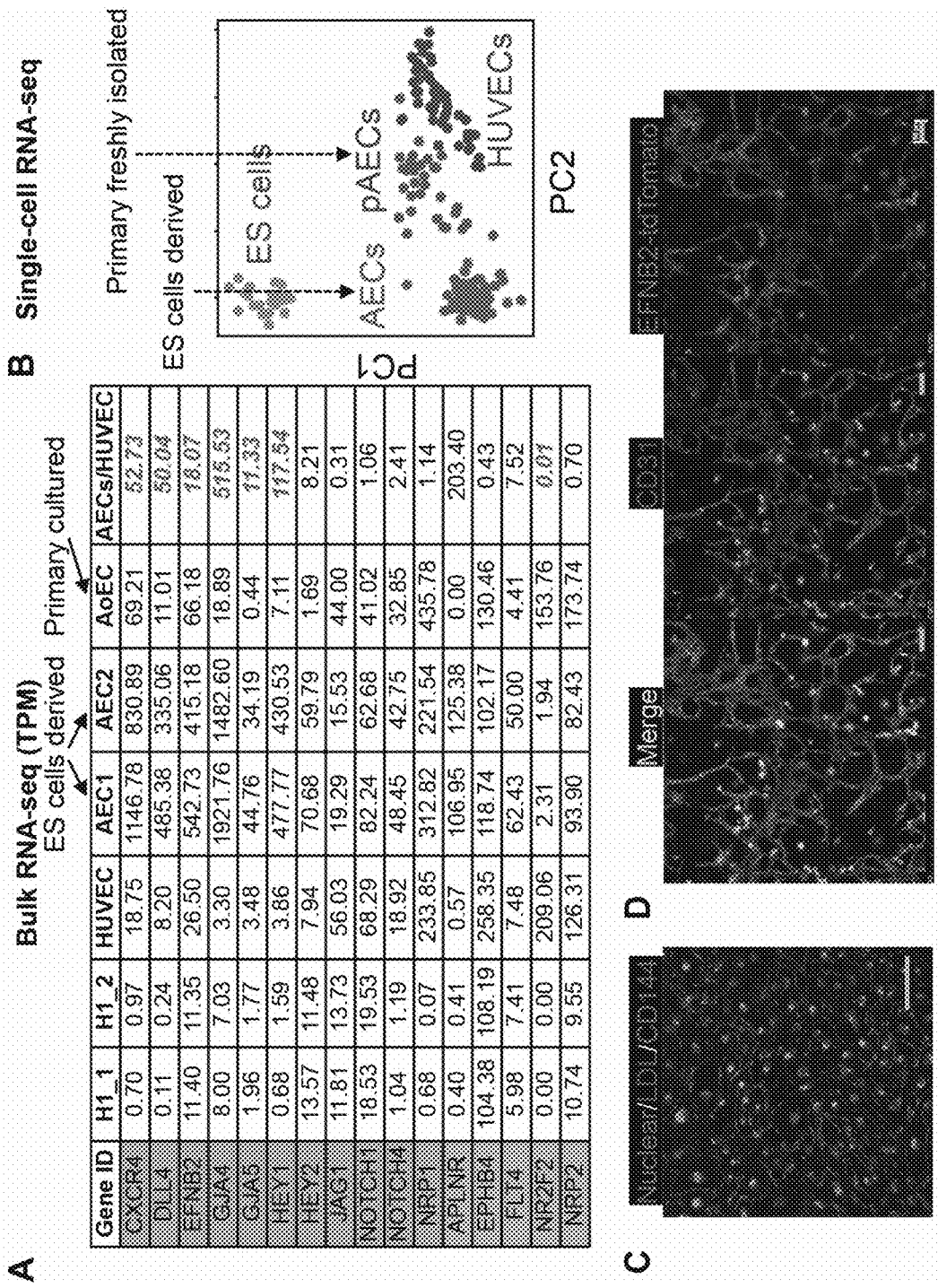
FIGS. 5A-5G present characterization of arterial endothelial cells. All arterial endothelial cells were derived by "five factors" medium. (A) TPM of bulk RNA-seq was shown. EFNB2-tdTomato$^{high}$/EPHB4-EGFP$^{low}$ (AECs) were sorted for RNA-seq. The ratio of AECs (average TPM from AEC 1 and AEC2) to HUVEC was calculated. AoEC, cultured aortic endothelial cells. (B) PCA of single-cell RNA-seq. AECs: sorted EFNB2-tdTomato$^{high}$/EPHB4-EGFP$^{low}$ cells, pAECs: primary arterial endothelial cells from freshly isolated human fetus dorsal aorta, ES: H1 ES cells. (C) LDL uptake. Scale bar=100 Arterial endothelial cells (passage 2) derived from wild type H1 cells were used. The purity was about 93% after being passaged, so cells used in panels C—H were not purified. (D) Matrigel encapsulation assay. Arterial endothelial cells (passage 3) derived from reporter cell line were used. Scale bar=100 (E) Vascular formation in fibrin gel. Arterial endothelial cells (passage 2) derived from wild type H1 cells were used for panels E-F. Scale bar=100 (F) Lumen formation of endothelial cells and pericytes co-cultured in fibrin gel. To visualize the lumen, cells were stained with CMFDA (green). Y-z and x-z projection was shown. Scale bar=100 µm. (G) Endothelial cells formed functional vessels in vivo. Wild type H1 derived-arterial endothelial cells (passage 2, purified by CD144 microbeads) were mixed with Matrigel™ and injected into SCID mice. After four weeks, rhodamine-dextran was retro-orbital injected to highlight perfused vessels. Scale bar=100 µm. CD31: anti human and mouse CD31 antibody, Santa Cruz, cat #SC-1506. hCD144: anti-human CD144-647 antibody, BD biosciences, cat #561567.
Figures 6A, 6B, 6C, 6D, 6E, 6F:
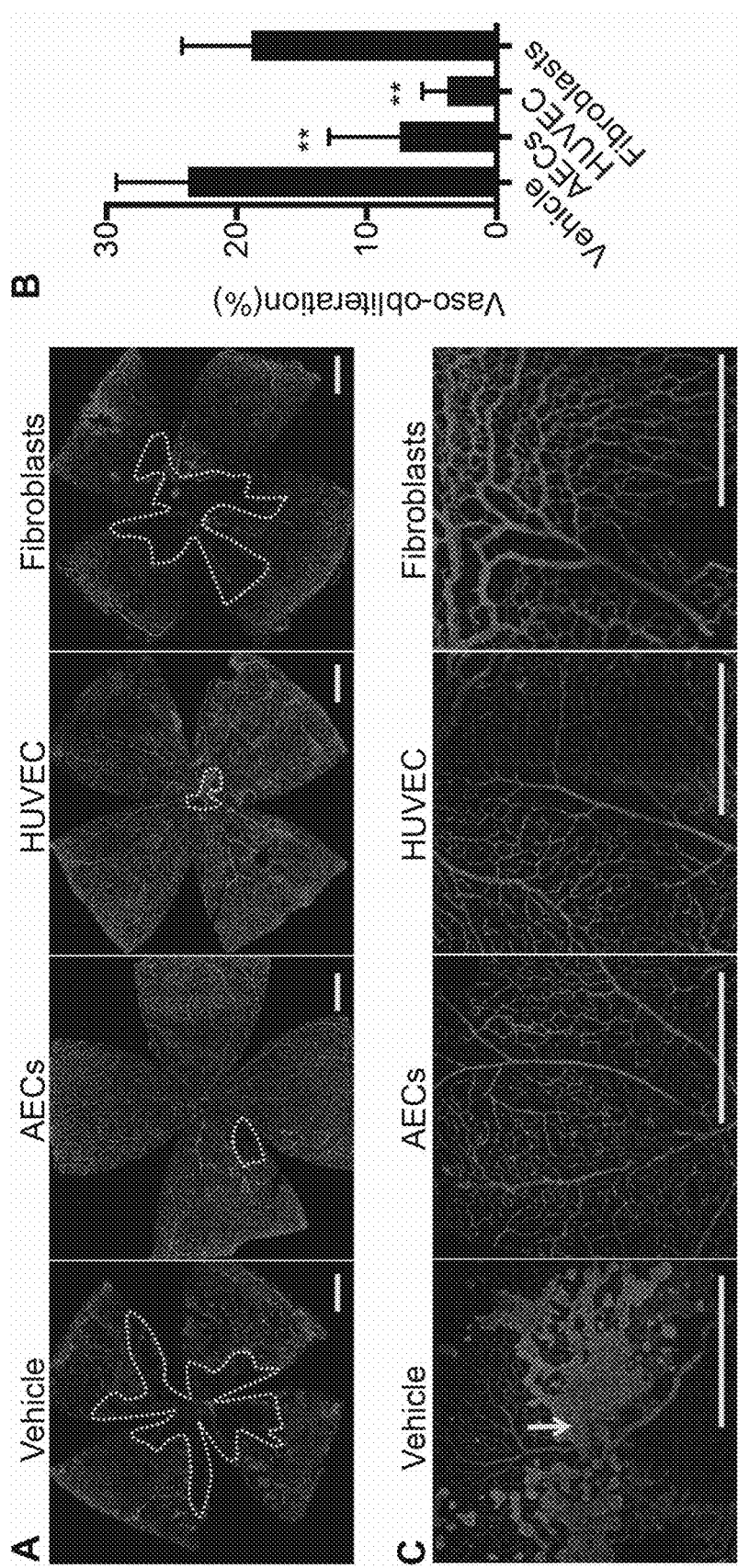
FIGS. 6A-6F demonstrate that arterial endothelial cells improve vascular function. (A) Flat-mounted retinas of oxygen-induced retinopathy. Endothelial cells were stained by CD31 antibody. Vaso-obliteration area was outlined. Scale bar=0.5 mm. (B) Statistics of vaso-obliteration. : P<0.01. The P value was calculated by comparing to vehicle group. Vehicle group: n=12, from three independent experiments, PBS was used. AECs group: n=16, from two independent experiments. HUVEC group: n=5. Fibroblast group: n=5. (C) Neovascular tuft was indicated by the arrow. Endothelial cells were stained by CD31 antibody. Scale bar=0.5 mm. (D) Representative laser Doppler perfusion imaging showing the blood flow in ischemia athymic mice. (E) A stacked bar graph showing the physiological status at post-operative day 40. Vehicle group: n=10, DF12 medium was used. 0.3M AECs group: n=11, $3 \times 10^5$ AECs were injected per mouse. 1M AECs group: n=10, $1 \times 10^6$ AECs were injected per mouse. 1M cord blood-derived endothelial colony forming cells (CB-ECFCs) group: n=10, $1 \times 10^6$ CB-ECFCs were injected per mouse. The animal death was caused by ischemia related infection. , P<0.001 (Chi-squared test, compared to vehicle group). (F) AECs formed vessels and recruited smooth muscle cells in mouse limb. AECs were stained with human specific CD31 antibody. Scale bar=100 µm. hCD31: anti human CD31 antibody, BD biosciences, cat #550274.

Endothelial cells generated with the five-factor protocol took up LDL, formed vascular networks, and maintained EFNB2 (Ephrin B2) expression in those networks (FIGS. 5C-5D). Another characteristic feature of functional AECs is decreased leukocyte adhesion relative to that of venous endothelial cells (Hauser et al., J Immunol 151, 5172-5185 (1993); Kalogeris et al., Am J Physiol 276, L9-L19 (1999)). Thus, we analyzed the ability of TNFα, a proinflammatory cytokine to induce leukocyte adhesion in different types of endothelial cells (De Caterina et al., 1995).

Figures 7A, 7B, 7C, 7D, 7E, 7F:
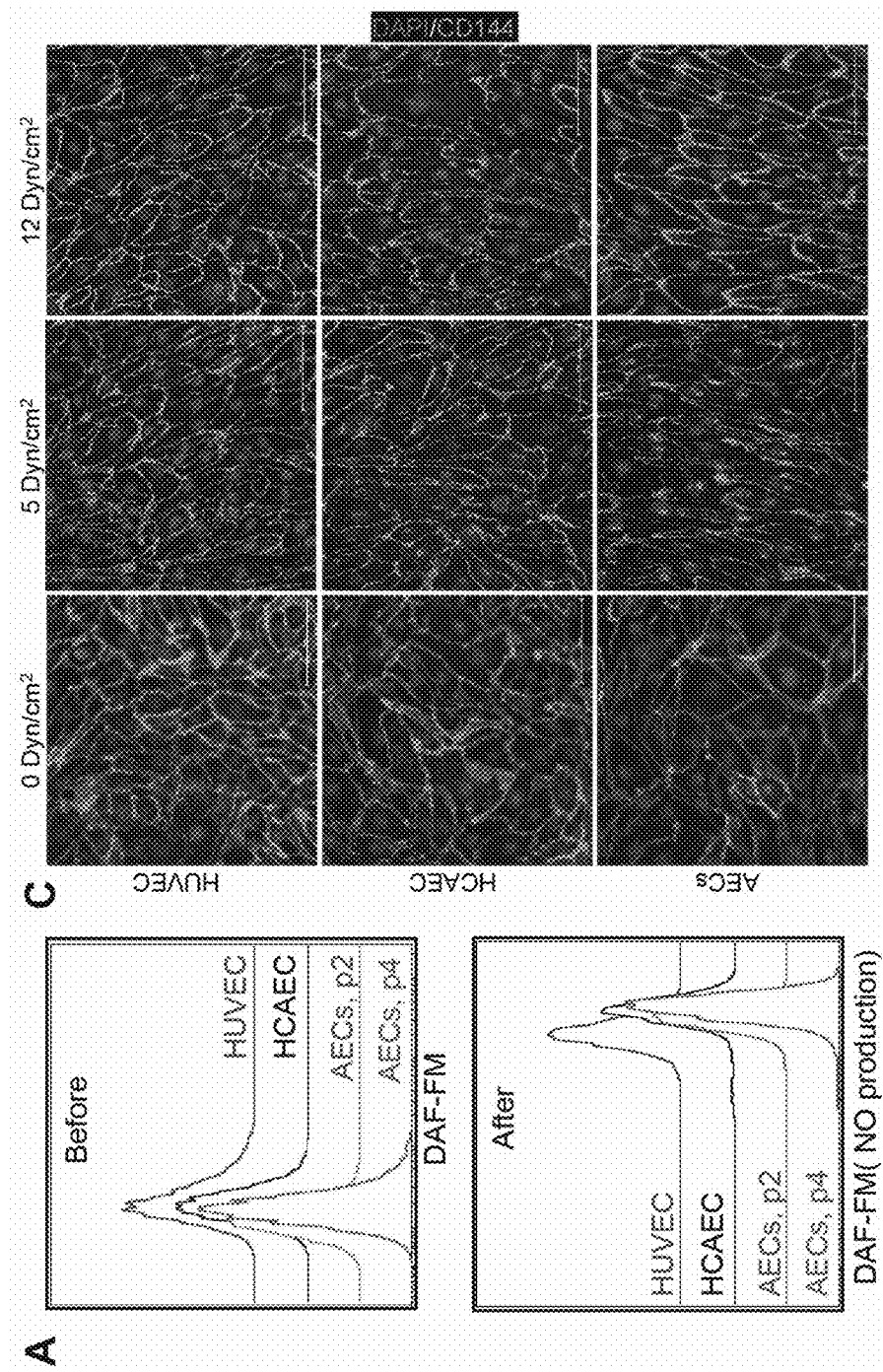
FIGS. 7A-7F present arterial-specific functional characterization of endothelial cells. (A) Nitric oxide (NO) production was revealed by the intensity of 4-amino-5-methylamino-2',7'-difluorofluorescein diacetate (DAF-FM), which is a NO-sensitive reagent that is useful for qualitative assessment of cellular NO production. Arterial endothelial cells (AECs) were derived from wild type H1 cells by "five factors" medium and used for experiments at passage 2 or 4. DAF-FM is nonfluorescent until it reacts with NO to form a fluorescent benzotriazole. The fluorescent intensity was measured by flow cytometry. Experiment was performed three times and typical data from one assay was shown. (B) Oxygen consumption rate was measured on XF24 analyzers (Seahorse Bioscience). Oligomycin was used to abolish the oxygen consumption. Carbonyl cyanide-4-(trifluoromethoxy)phenylhydrazone (FCCP), which is a potent uncoupler of oxidative phosphorylation in mitochondria that disrupts ATP synthesis by transporting protons across cell membranes, was used to measure maximal respiration capacity. Antimycin A and Rotenone were applied simultaneously to completely block the electron transport chain. *: P<0.05, n=3. The P value was calculated by comparing to HUVEC. HCAEC, human coronary arterial endothelial cells. (C) Shear Stress response performed on ibidi Pump System (Red perfusion set, µ-Slide VI 0.4. (D) The statistics data of shear stress response. Ratio of cell length to width was used to demonstrate the elongation of cells in response to shear stress. For each cell type, 100 cells were measured to do the statistics. Data are represented as mean±SD. *: P<0.05; ***:P<0.001, n=100 cells from three independent experiments. (E) Leukocyte (round cells) adhesion assay. Scale bar=200 µm. AECs were used at passage 1 or 4. (F) Statistics of leukocyte adhesion assay. Leukocyte number was counted for each image. Data are represented as mean±SD. *: P<0.05, n=3 images from three independent experiments. The P value was calculated by comparing to HUVEC with TNFα treatment.

Finally, we examined whether the human ES cell-derived AECs exhibit arterial-specific functional characteristics. First, the "five factors" AECs produced NO at levels comparable to primary human coronary arterial endothelial cells (HCAECs), and at higher levels than HUVEC cells (FIG. 7A). Second, AECs consumed oxygen at rates similar to primary arterial endothelial cells, and at higher rates than HUVEC cells (FIG. 7B). Third, the AECs elongated in response to shear stress to a similar degree as primary arterial endothelial cells, and to a greater degree than HUVEC cells (FIGS. 7C-7D). The AECs exhibited low levels of TNFα-induced leukocyte adhesion (Hauser et al., *J Immunol* 151, 5172-5185 (1993); Kalogeris et al., *Am J Physiol* 276, L9-L19 (1999)) that was comparable to primary arterial endothelial cells and was much lower than that of HUVEC cells (FIGS. 7E-7F). In summary, our combined results demonstrate that the AECs are characterized by gene expression and functional properties, which are distinct from venous endothelial cells but consistent with arterial endothelial cells.

Figure 12:
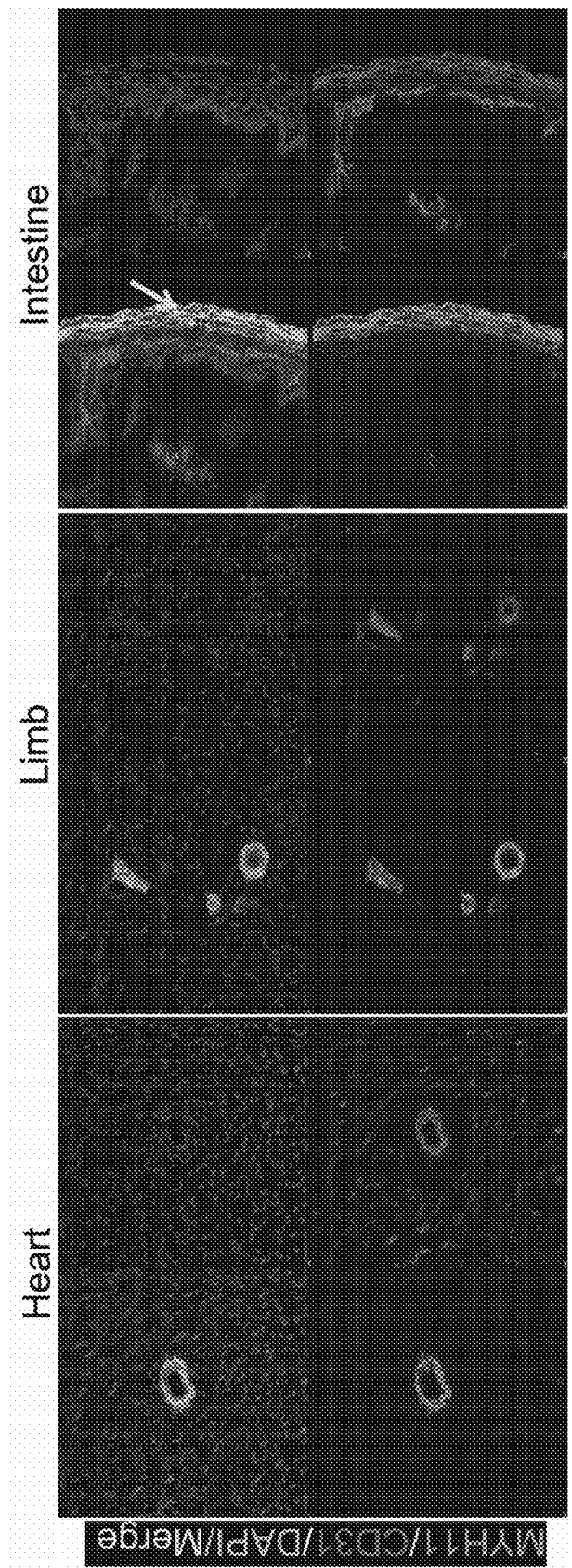
FIG. 12 demonstrates MYH11-positive vascular smooth muscle in mouse heart, limb, and intestine. In mouse heart and limb, MYH11-positive vascular smooth muscle is recruited to the blood vessels. In the intestine, smooth muscle cells express both MYH11 and CD31 (arrow indicated), demonstrating that MYH11$^+$CD31$^-$ cells are vascular smooth muscle cells while MYH11$^+$CD31$^+$ cells are intestinal smooth muscle cells.

Previous studies revealed that the vascular smooth muscle expressed ACTA2 (smooth muscle actin or "SMA"), TAGLN (Smooth muscle protein 22-alpha or "SM22A"), MYH11 (myosin, heavy chain 11, smooth muscle), and elastin (ELN). Owens et al., *Physiol Rev* 84, 767-801 (2004). We further demonstrated that CD31 could be used to distinguish intestinal and vascular smooth muscle cells. As shown in FIG. 12, MYH11-positive vascular smooth muscle is recruited to the blood vessels. In the intestine, smooth cells express both MYH11 and CD31 (arrow indicated), demonstrating that MYH11$^+$CD31$^-$ cells are vascular smooth muscle cells while MYH11$^+$CD31$^+$ cells are intestinal smooth muscle cells.

TABLE 2

Arterial Enriched Growth Factor Related Genes

| Related Pathway | Gene | Description | Treatment |
| --- | --- | --- | --- |
| Adiponectin | ADIPOR2 | Adiponectin receptor protein 2 | Add adiponectin (ADIPO) |
| Angiopoietin | ANGPT2 | Angiopoietin-2 | Add ANGPT2 |
| BMP | CRIM1 | Cysteine-rich motor neuron 1 protein. Antagonist of BMP4/7 | Remove BMP4 |
| Chemerin | CMKLR1 | Chemokine-like receptor 1 | Add Chemerin |
| EFNA1 | EFNA1 | Ephrin-A1. Positively regulated by TNF and VEGF | Add TNF or VEGF |
| EFNB2 | EFNB2 | Ephrin-B2. Arterial endothelial cell marker | N/A |
| EGF and VEGF related | LDLR | Low-density lipoprotein receptor. Positive regulation of KDR and EGF | Add EGF or VEGFA |
| EGF and VEGF related | SSFA2 | Sperm-specific antigen 2. Positively regulated by KRAS, which can be activated by EGF and VEGF | Add EGF or VEGFA |
| EGF related | CELSR1 | Cadherin EGF LAG seven-pass G-type receptor 1. Interacts with EGFR | Add EGF |
| EGF related | CD2AP | CD2-associated protein. Interacts with EGFR | Add EGF |
| EGF related | CD9 | CD9 antigen Binds to EGF | Add EGF |
| EGF related | THBD | Thrombomodulin. Positive regulation of EGFR | Thrombomodulin (THBD) |
| FGF | FGFR2 | Fibroblast growth factor receptor 2 | Add FGF2 |
| FGF related | ARRB2 | Beta-arrestin-2. FGFR1 recruits ARRB2 upon agonist treatments | Add FGF2 |
| IFN | IFNGR2 | Interferon gamma receptor 2 | Add IFNg |
| Insulin/IGF | IGFBP3 | Insulin-like growth factor 2 mRNA-binding protein 3 Inhibits IGF pathway | Add insulin |
| Interleukin | IL13RA1 | Interleukin-13 receptor subunit alpha-1 | Add IL13 |
| LIF | STAT3 | Signal transducer and activator of transcription | Add LIF |
| LIF or Wnt related | YES1 | Tyrosine-protein kinase Yes. Regulated by LIF and Wnt | Add LIF or Wnt |
| NGF | PTPRG | Receptor-type tyrosine-protein phosphatase gamma. Inhibits NGF function | Add B-NGF to reverse its effects |
| Notch | DLL4 | Delta-like protein 4 | NOTCH signaling, previously reported |
| Notch | NOTCH1 | Neurogenic locus notch homolog protein 1 | NOTCH signaling, previously reported |
| Notch related | APLP1 | Amyloid-like protein 1. Processed by γ-secretase, which is also part of Notch signaling | Add APLP1 |
| Notch related | PALM | Paralemmin-1. Overexpressed in ESR1+ breast cancer cells. Notch actives ESR dependent transcription | Add PALM |
| Notch related | DAG1 | Dystroglycan: acts downstream of Notch signaling pathway | Add DAG1 |
| NPR | NPR2 | Atrial natriuretic peptide receptor 2 | Add C-type natriuretic peptide |
| PDGF related | SLC9A3R2 | Na(+)/H(+) exchange regulatory cofactor NHE-RF2 | Increase PDG-BB activity, so add PDGF-BB |
| PDGF related | ABCA1 | ATP-binding cassette sub-family A member 1. Suppressed by PDGF | Add PDGF-BB to suppress it |

TABLE 2-continued

Arterial Enriched Growth Factor Related Genes

| Related Pathway | Gene | Description | Treatment |
| --- | --- | --- | --- |
| SDF | CXCR4 | C—X—C chemokine receptor type 4 | Add CXCL12/SDF |
| Semaphorin | PLXNA2 | Plexin-A2 | Add Semaphorin (SEMA) |
| Slit | ROBO2 | Roundabout homolog 2; response to slit ligand | Add Slit2-N |
| TGF | BRCA1 | Breast cancer type 1 susceptibility protein; expression is inhibited by TGFβ1. | Add or remove SB431542 (TGF receptor inhibitor) |
| TNF | SLC20A1 | Sodium-dependent phosphate transporter 1. Upregulated by TNF | Add TNFα |
| VEGF | VEGFA | | VEGF signaling, previously reported |
| VEGF related | GRIA2 | Glutamate receptor 2, GluR2, upregulated by VEGF | Add GlutaMAX ™ medium (Glu) |
| VEGF related | LEPR | Leptin receptor. Leptin upregulates VEGF signaling | Add LEPTIN |
| VEGF related | XPR1 | Xenotropic and polytropic retrovirus receptor 1. Binds to ACTR6, which can be activated by VEGF | Add VEGF |
| VEGF related | INPP5K | Inositol polyphosphate 5-phosphatase K. Inositol pathway suppresses VEGF | Add L-690,330 (inositol monophosphatase inhibitor) (L690) |
| Wnt | FZD4 | Frizzled-4 | WNT signaling, previously reported |
| Wnt | FZD7 | Frizzled-7 | WNT signaling, previously reported |
| Wnt | FZD10 | Frizzled-10 | WNT signaling, previously reported |
| N/A | SLC20A2 | Sodium-dependent phosphate transporter 2 | N/A |

Materials and Methods

Isolation of mouse endothelial cells for single-cell RNA-seq: Twenty-four E11.5 mouse (CD-1 background) embryos were harvested. The head, tail, limb, internal organ, and somite were removed. The aorta-gonad-mesonephros (AGM) tissue was incubated in 2 mg/ml collagenase type IV (Life Technologies, cat #17104-019) and 0.25 mg/ml dispase (Life Technologies, cat #17105-041) solution for 15 minutes on ice to let enzyme penetrate into the tissue. The tissue with enzyme was then incubated at 37° C. for 10 minutes. The enzyme was neutralized by 2% FBS-HBSS and pipetted up and down to further dissociate the cells. The cells were immunostained and CD31$^+$CD144$^+$CD41$^-$CD45$^-$ endothelial cells were sorted out by flow cytometry. CD41 and CD45 were used to deplete hematopoietic stem cells.

Isolation of human fetus arterial endothelial cells for single-cell RNA-seq: Human fetal aorta tissue (14 weeks gestation) was dissected from the aortic arch to the abdominal bifurcation. Tissue was obtained from the Human Fetal Tissue Repository at Albert Einstein College of Medicine of Yeshiva University (Bronx, N.Y.). This work was done under approval from the UW-Madison Health Sciences IRB and the IRB of Albert Einstein College of Medicine. The adventitia layer of human fetus dorsal aorta was completely removed and the rest of the tissue was cut into small pieces. The tissue was then digested by 300 U/ml collagenase/elastase (Worthington Biochem, cat #LK002067) for one hour at 37° C., and the tissue was pipetted up and down every 20 minutes. The endothelial cells were sorted by flow cytometry using anti-CD31 antibody.

Single cell RNA-sequencing. For mouse AGM cells, 15 μl cell suspension (containing 5×10$^4$ cells) was loaded into a Fluidigm C$_1$™ chip. RNA isolation, cDNA library preparation were performed on Fluidigm C$_1$™ Single-Cell Auto Prep System as manufacturer suggested (Smarter-seq1 protocol). cDNA concentration was measured by Quant-iT™ PicoGreen® dsDNA assay kit (Life Technology, cat #P7589) and diluted to 0.1-0.3 ng/μl. cDNA was tagmented (by a modified transposition reaction) and barcoded by using Nextera XT DNA Sample Prep Kit (Illumina, cat #FC-131-1024). For sequencing (Illumina, HiSeq2500), 18-24 samples were pooled. In total, 84 cells were sequenced. After doublet exclusion and outlier removing, 70 cells were used for further analysis.

For AECs derived by the "five factors" protocol, CD144$^+$/EFNB2-tdTomato$^{high}$/EPHB4-EGFP$^{low}$ cells were sorted and loaded into a Fluidigm C$_1$™ chip. cDNA were prepared and sequenced as mentioned above. In total, 96 cells were sequenced and used for further analysis.

For primary AECs ("pAECs;" freshly isolated from 14 weeks old human fetus dorsal aorta), smarter-seq2 protocol was applied to Fluidigm C$_1$™ single-cell auto prep system for cDNA preparation. Smarter-seq2 is has been shown to improve cDNA yield and sequencing sensitivity[41], thus it's suitable for samples with relative low RNA quality. In total, 48 cells were sequenced and used for further analysis.

H1 ES and HUVEC cells were prepared by Fluidigm C$_1$™ single-cell auto prep system using smarter-seq2 protocol. In total, twenty-four H1 and 48 HUVEC cells were sequenced and used for further analysis.

Hierarchical clustering: Single-cell RNA-seq data (TPM) were generated from RSEM. For each gene, the log 2 TPM was scaled to z scores with mean 0 and variance 1. Prior to taking the logarithm, TPM below 1 was imputed as 1. Hierarchical clustering was performed using the Euclidean distances between cells (FIG. 1).

Figure 10:
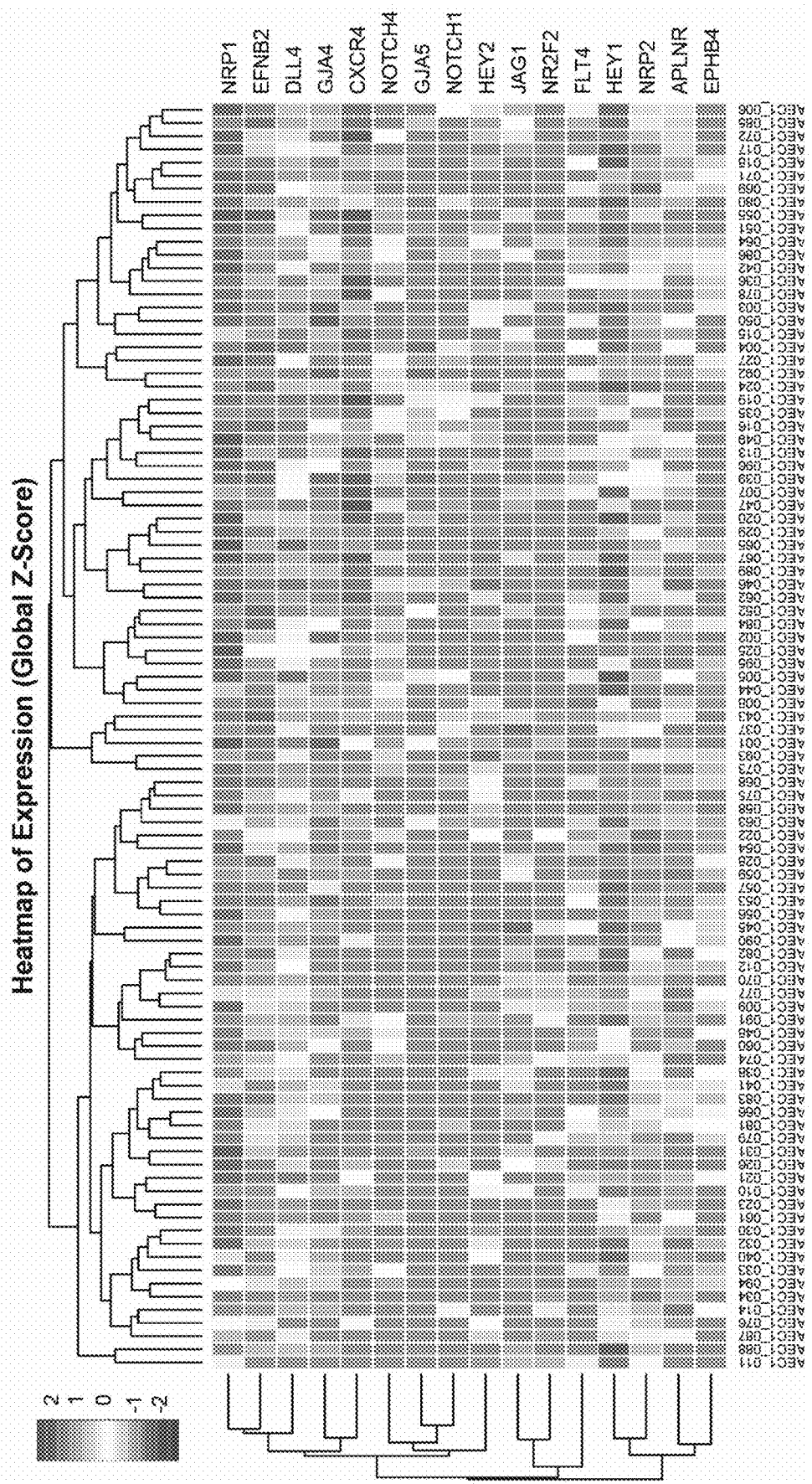
FIG. 10 presents a heat-map of expression obtained using single-cell RNA-seq. Hierarchical clustering analysis was performed for arterial and venous genes of EFNB2-tdTomato$^{high}$/EPHB4-EGFP$^{low}$ AECs derived by the "five factors" protocol as described herein.

Data analysis by SINGuLAR Analysis Toolset 2.1: Single-cell RNA-seq data (TPM) was loaded to SINGuLAR Analysis Toolset 2.1. The outliers were removed by the "identifyOutliers( )" command. Arterial and venous markers of the samples were them analyzed by the "autoAnalysis( )" command. As a result, PCA plot of FIG. 1C was automatically generated. Heat map of AECs data (FIG. 10) was also generated by "autoAnalysis( )" of SINGuLAR.

Principle component analysis by R program: Principle component analysis (PCA) was performed on single-cell RNA-seq data (FIG. 5B). To adjust for sequencing depth variation across different cells, expected counts were normalized by mediumn-ratio normalization. To reduce the effect of potential outliers, for each gene, values that were greater than the 95th quantile of the gene-specific expression had been imputed using the 95th quantile. Prior to PCA, the gene-specific normalized expression was rescaled to values with mean 0 and standard deviation 1 for all genes. The PCA analysis was performed using prcomp( ) function in R.

Generation of the growth factor related gene list: Five Amigo Go Terms (version 1.8) growth factor binding (GO: 0019838), growth factor activity (GO:0008083), growth factor receptor binding (GO:0070851), receptor activity (GO:0004872), and receptor binding (GO:0005102) were combined. The combined list was then joined with plasma membrane (GO:0005886) to generate the growth factor related gene list. The list was further joined with "arterial-enriched genes" from Table 5 to generate an arterial enriched growth factor related gene list of Table 6.

Gene targeting on the H1 ES cells: The 5' and 3' homology arms of EFNB2 targeting vector were synthesized by IDT (gBlock) with introducing Sal I and BamH I (5' arm), Bmt I and Mlu I (3' arm) restriction sites to facilitate subcloning into the targeting vector. The 5' and 3' homology arms of EPHB4 targeting vector were PCR amplified from BAC (bacterial artificial chromosome).

To achieve the best electroporation efficiency, human ES cells (H1) were EDTA passaged (1:4 split) and cultured to reach 80-90% confluence two days before the experiment. At the day of the experiment, ES cells were dissociated by Accutase, washed once with E8 medium, and resuspended at densities of $5 \times 10^6$ cells/mL in E8 medium with 10 mM Hepes buffer (pH 7.2-7.5) (Life Technologies). For electroporation, 400 μL of cell suspension, 7.5 μg gRNA plasmid, 7.5 μg spCas9 plasmid, and 10 μg linearized DNA template plasmid were mixed in a 4-mm cuvette (Bio-Rad) and immediumtely electroporated with a Bio-Rad Gene Pulser. Electroporation parameters were 250 V, 500 μF, and infinite resistance. Cells were then plated on Matrigel™-coated plate in E8 medium (10 μM Y27632 was added for the first day). For the EFNB2-tdTomatom cell line, 100 μg/ml Geneticin was added to the medium when cells reached to 20% confluence (usually 3-4 days after electroporation) and drug selection was used for the last five days. For the EPHB4-EGFP cell line, 0.5 μg/ml puromycin was added to the medium when cells reached to 20% confluence. Due to the drug sensitivity of cells in E8 medium, eight hours/day puromycin treatment was performed for five days. Surviving colonies were picked four to six days after drug selection and expanded in E8 medium.

Karyotyping: Karyotyping was performed by WiCell Research Institute.

Southern blot: The probe was synthesized by using PCR DIG Probe Synthesis Kit (Roche, Cat #11 636 090 910). The southern blot was performed following DIG Application Manual for Filter Hybridization from Roche.

TABLE 3

Culture Medium Components

| Medium components | E8 | E8BAC | E6 | E5 | E7V | Five factors |
|---|---|---|---|---|---|---|
| DMEM/F12 | + | + | + | + | + | + |
| L-ascorbic acid-2-phosphate magnesium (64 ng/ml) | + | + | + | + | + | + |
| Sodium selenium (14 ng/ml) | + | + | + | + | + | + |
| NaHCO$_3$ (543 μg/ml) | + | + | + | + | + | + |
| Transferrin (10.7 μg/ml) | + | + | + | + | + | + |
| Insulin (20 μg/ml) | + | + | + | | + | |
| FGF2 (100 ng/ml) | + | + | | | + | + |
| TGFβ1 (2 ng/ml) | + | + | | | | |
| BMP4 (5 ng/ml) | | + | | | | |
| Activin A (25 ng/ml) | | + | | | | |
| CHIR99021 (1 μM) | | + | | | | |
| VEGFA$_{165}$ (50 ng/ml) | | | | | + | + |
| SB431542 (10 μM) | | | | | | + |
| RESV (5 μM) | | | | | | + |
| L690 (10 μM) | | | | | | + |

Human pluripotent stem cell culture and differentiation: iPS cell line 005B23.1 was derived from skin punch fibroblast and maintained on recombinant vitronectin-coated plates. DF19.11 was derived from foreskin fibroblast. CD-3-1 was derived from cord blood cells. PBMC was derived from peripheral blood mononuclear cells. H1 and H9 ES cells were derived from male and female embryos, respectively.

Human pluripotent stem cells were cultured in E8 medium on a Matrigel™-coated plate (excepted 005B23.1). To achieve the best differentiation results, ES cells were split by EDTA at 1:4 ratios two days before the differentiation. The cells reached 80-90% confluency two days later. At the day of the differentiation, ES cells were dissociated by Accutase (Invitrogen) for 3 minutes at 37° C. The cells were plated on vitronectin-coated plate (recombined vitronectin, 50 μg/10-cm dish) at 1:3 ratios ($1.1$-$1.5 \times 10^5$ cells/cm$^2$). The cells reached 100% confluence after 36 hours. To improve cell survival, 10 μM Y27632 was used for the first day. The cells were cultured in E8BAC medium (see Table 3: E8 medium supplemented with 5 ng/ml BMP4, 25 ng/ml Activin A, and 1 μM CHIR99021) for two days. E6 (E8 medium minus FGF2, and TGFβ1) medium supplemented with growth factors or small molecules was then used to induce endothelial cell differentiation for another three days. Medium was changed every day. The cells were harvested at day 5. To isolate CD31$^+$CD34$^+$ cells, the cells were labeled with CD34 magnetic beads and processed through autoMACS (Miltenyi Biotec). The purified cells were cultured on fibronectin-coated (Life Technologies, Cat #33016-015) (100 μg/10-cm dish) or vitronectin-coated (50 μg/10-cm dish) dishes with E7V (E6+100 ng/ml FGF2+50 ng/ml VEGFA) medium.

Arterial endothelial cell differentiation and expansion: It took six days for AECs differentiation. From day 0 to day 2, human ES/iPS cells were first differentiated into mesoderm cells as mentioned above. From day 2 to day 6, E5 medium was used and growth factors or small molecules were added as indicated. With the combination of "five factors," AECs were induced by E5 medium supplemented with 100 ng/ml FGF, 50 ng/ml VEGF, 10 μM SB431542, 5 μM RESV, and 10 μM L690 from day 2 to day 6.

AECs were purified by CD144 microbeads (Miltenyi Biotec, cat #130-097-857) for some of the functional assays. After optimization (FIG. 9), AECs were maintained in FVIR (E5+100 ng/ml FGF, 50 ng/ml VEGF, 10 μM SB431542, 5 μM RESV) or FVIR+Ins (FVIR medium+10 μg/ml insulin) medium on fibronectin- or vitronectin-coated dishes.

LDL-uptake assay: To perform the LDL-uptake assay, 2 μg/ml acetylated-LDL-FITC was added to the medium and cultured for 4 hours. Ten minutes before imaging, 2 µg/ml Hoechst was added to medium. To co-stain with CD144, anti-CD144-647 antibody was added to medium two hours before imaging. The medium was removed and HBSS was added for live cell imaging. It is important to image the cell in live because fixing the cell will diminish LDL-FITC signal.

MATRIGEL™ encapsulation assay: $1.5\times10^3$ endothelial cells/pi and $0.75\times10^3$ pericytes/µl (ScienCell, cat #1200) were encapsulated in 6.5 mg/ml Matrigel™. A 10 µL Matrigel™/cell solution was spotted in the middle of 24-well plate and incubated for 5 mins at 37° C. for solidification. E7V mediumwas then applied. Immunostaining was performed on day 4 and the structures were imaged using Nikon confocal microscopy.

In vivo MATRIGEL™ plug angiogenesis assay: $5\times10^5$ endothelial cells were resuspended in 100 µl E7V medium and 200 µL Matrigel and then the 300 µL cell/Matrigel™ mixture was subcutaneously injected into the neck of nude mice. After two weeks of inoculation, the Matrigel™ was harvested, fixed, and immunostained. For dextran injection, 100 µg rhodamine-conjugated dextran was retro-orbital injected into mice after four weeks of inoculation. Ten minutes after dextran injection, the Matrigel™ plug was harvested, fixed, and immunostained.

Fibrin Gel Encapsulation Assay: $1.5\times10^3$ endothelial cells/pi and/or $0.75\times10^3$ pericytes/µl were encapsulated in fibrin gel. Fibrin gel was prepared by 2.5 mg/ml fibrinogen (EMD, cat #341578) and 0.5 U/ml thrombin (Sigma, cat #T-9326). A 10 µL fibrin gel/cell solution was spotted in the middle of 24-well plate and incubated for 10 mins at 37° C. for solidification. E7V medium was then applied. Immunostaining was performed on day 4 and the structures were imaged using confocal microscopy.

Oxygen-Induced Retinopathy Model: The experiments were performed under approval from UW-Madison Ophthalmology and Visual Science IRB. Oxygen-induced retinopathy was induced in C57/BL6 wild-type mice as previously described[21]. Briefly, postnatal day seven mice were exposed in 75% oxygen for five days. At day postnatal day 12, they were transfer back to room air and received 1 µl intravitreal injection containing $5\times10^4$ cells. Phosphate buffered saline (PBS) was used as vehicle and injected as the control. Five days later, retinas were harvested and immunostaining was performed.

Hind Limb Ischemia Model: The experiments were performed under approval from UW-Madison Cardiovascular Physiology Core Facility IRB. The Hind limb ischemia model was generated as previously described[22]. Briefly, 10-12 weeks old female athymic nude mice (Crl:NU(NCr)-Foxn1$^{nu}$, Charles River Laboratories, Chicago, Ill.) were used. Ten to twenty weeks old instead of four to six weeks old mice were used as the recovery of the older mice was slower and more similar to human limb ischemia. The common iliac artery was ligated in the abdominal cavity and just caudal to the inguinal ligament, the femoral artery was ligated in two locations and removed. The mice were randomly assigned into four groups right after surgery and injected cells or DF12 medium. The cells ($0.3\times10^6$, $1\times10^6$, or $3\times10^6$ cells per mouse) were suspended in 300 µl DF12 medium and injected intramuscularly into six site of the gracilis muscle in the ischemic leg. The surgery was performed on seven to eight mice per day.

Nitric Oxide Production Assay: The endothelial cells were seeded on vitronectin coated 24-well plate ($1\times10^5$ cells/well). AECs were cultured in FVIR+Ins medium. HUVEC (Lonza, cat #CC-2519) was cultured in EGM2 (Lonza, cat #CC-3202)) medium. HCAEC (Lonza, cat #CC-2585) was cultured in EGM2 medium for one day and then in FVIR+Ins medium for another day. Two days later, all the medium were changed to fresh FVIR+Ins medium containing 1 µM DAF-FM (Life technologies, cat #D-23844). Cells were cultured for 30 mins and then harvested for flow cytometric analysis. DAF-FM is nonfluorescent until it reacts with NO to form a fluorescent benzotriazole. To achieve the consistent results, the same cell density and same medium is used after adding DAF-FM.

Oxygen Consumption Assay: $4\times10^4$ cells/well were seeded on the XF24-well plate (Seahorse Bioscience) for overnight. AECs were cultured in FVIR medium, HCAEC and HUVEC were culture in EGM2 medium. One day later, medium was changed to Mito Assay medium (Seahorse Bioscience) and oxygen consumption rate was measured by XF24 analyzers according to manufacture's instruction (Seahorse Bioscience). Oligomycin (0.5 µM) was injected at time point 3 to abolish the oxygen consumption by inhibiting ATP-synthase. FCCP (2 µm, Mitochondrial uncoupler) was injected at time point 6 to uncouple the electron transport chain from the oxidative phosphorylation thus measuring the maximal respiration capacity. To measure non-mitochondrial respiration, 1 µm Antimycin A and 1 µm Rotenone were applied simultaneously at time point 9 to completely block the electron transport chain at cytochrome bc1 (complex III) and NADH dehydrogenase (complex I), respectively.

Shear Stress Response: Shear stress response was assayed using an ibidi Pump System (Red perfusion set, µ-Slide VI 0.4). For each channel of µ-Slides, 30 µl cell suspension ($5\times10^5$ cells/ml, with 10 µM Y27632) was loaded. After cell attached, 130 µl fresh medium was added to each channel. Two days later, µ-Slide was perfused by ibidi Pump System. After perfusion for 24 hours, cells were harvested and immunostained.

Since FVIR+Ins medium promoted the elongation of endothelial cells, E7V medium was used to culture "five factors" AECs before and during the 24-hour shear stress response experiment.

Leukocyte Adhesion Assay: All endothelial cells were cultured on a fibronectin coated 24-well plate. AECs were cultured in FVIR medium; HUVEC and HCAEC were cultured in EGM-2 medium (Lonza). When the cells reached to 100% confluence, they were treated with or without 10 ng/ml TNFα for four hours. Then $1\times10^6$ U937 cells were suspended in 0.5 ml fresh RMPI1640+10% FBS and added to each well. Twenty to 60 minutes later, cold medium (RMPI1640+10% FBS) was used to gently wash away the non-attached cells. Washing was repeated two more times. Cells were imaged immediumtely.

Antibody Reagents: Anti-mouse CD41-FITC (Biolegend, Catalog #133904), Anti-mouse CD45-FITC (STEMCELL technologies, Catalog #10710), Anti-mouse CD144-PE (BD, Catalog #562243), Anti-mouse CD31-APC (BD, Catalog #551262), Anti-human CD31-FITC (BD, Catalog #555445), Anti-human CD31-V421 (BD, Catalog #564089), Anti-human CD31-PE (BD, Catalog #555446), Anti-human CD34-647 (BD, Catalog #555824), Anti-human CD144-647 (BD, Catalog #561567), Anti-human DLL4-APC (Miltenyi, Catalog #130-096-560), Anti-human CXCR4-APC (BD, Catalog #560936), Anti-CD34 Micro bead (Miltenyi, 130-046-703), Anti-CD144 Micro bead (Miltenyi, 130-097-857), Anti-pAKT (ser473) (Cell signaling, Catalog #4060), Anti- AKT (Cell signaling, Catalog #4691), Anti-GAPDH (EMD Millipore, Catalog #MAB374).

REFERENCES

1. Go, A. S., et al. Heart disease and stroke statistics—2014 update: a report from the American Heart Association. *Circulation* 129, e28-e292 (2014).
2. Epstein, A. J., Polsky, D., Yang, F., Yang, L. & Groeneveld, P. W. Coronary revascularization trends in the United States, 2001-2008. *Jama* 305, 1769-1776 (2011).
3. Goodney, P. P., Beck, A. W., Nagle, J., Welch, H. G. & Zwolak, R. M. National trends in lower extremity bypass surgery, endovascular interventions, and major amputations. *J Vasc Surg* 50, 54-60 (2009).
4. Campbell, G. R. & Campbell, J. H. Development of tissue engineered vascular grafts. *Curr Pharm Biotechnol* 8, 43-50 (2007).
5. Aranguren, X. L., et al. Unraveling a novel transcription factor code determining the human arterial-specific endothelial cell signature. *Blood* 122, 3982-3992 (2013).
6. Tousoulis, D., Kampoli, A. M., Tentolouris, C., Papageorgiou, N. & Stefanadis, C. The role of nitric oxide on endothelial function. *Curr Vasc Pharmacol* 10, 4-18 (2012).
7. De Caterina, R., et al. Nitric oxide decreases cytokine-induced endothelial activation. Nitric oxide selectively reduces endothelial expression of adhesion molecules and proinflammatory cytokines. *J Clin Invest* 96, 60-68 (1995).
8. Barbato, J. E. & Tzeng, E. Nitric oxide and arterial disease. *J Vasc Surg* 40, 187-193 (2004).
9. Luiking, Y. C., Engelen, M. P. & Deutz, N. E. Regulation of nitric oxide production in health and disease. *Curr Opin Clin Nutr Metab Care* 13, 97-104 (2010).
10. Legein, B., Temmerman, L., Biessen, E. A. & Lutgens, E. Inflammation and immune system interactions in atherosclerosis. *Cell Mol Life Sci* 70, 3847-3869 (2013).
11. Papaioannou, T. G. & Stefanadis, C. Vascular wall shear stress: basic principles and methods. *Hellenic J Cardiol* 46, 9-15 (2005).
12. dela Paz, N. G. & D'Amore, P. A. Arterial versus venous endothelial cells. *Cell Tissue Res* 335, 5-16 (2009).
13. Ando, J. & Yamamoto, K. Effects of shear stress and stretch on endothelial function. *Antioxid Redox Signal* 15, 1389-1403 (2011).
14. Wang, H. U., Chen, Z. F. & Anderson, D. J. Molecular distinction and angiogenic interaction between embryonic arteries and veins revealed by ephrin-B2 and its receptor Eph-B4. *Cell* 93, 741-753 (1998).
15. Chong, D. C., Koo, Y., Xu, K., Fu, S. & Cleaver, O. Stepwise arteriovenous fate acquisition during mammalian vasculogenesis. *Dev Dyn* 240, 2153-2165 (2011).
16. Cong, L., et al. Multiplex genome engineering using CRISPR/Cas systems. *Science* 339, 819-823 (2013).
17. Mali, P., et al. RNA-guided human genome engineering via Cas9. *Science* 339, 823-826 (2013).
18. Hou, Z., et al. Efficient genome engineering in human pluripotent stem cells using Cas9 from *Neisseria meningitidis*. *Proc Natl Acad Sci USA* 110, 15644-15649 (2013).
19. Hong, C. C., Peterson, Q. P., Hong, J. Y. & Peterson, R. T. Artery/vein specification is governed by opposing phosphatidylinositol-3 kinase and MAP kinase/ERK signaling. *Curr Biol* 16, 1366-1372 (2006).
20. Ditadi, A., et al. Human definitive haemogenic endothelium and arterial vascular endothelium represent distinct lineages. *Nat Cell Biol* 17, 580-591 (2015).
21. Smith, L. E., et al. Oxygen-induced retinopathy in the mouse. *Invest Ophthalmol Vis Sci* 35, 101-111 (1994).
22. Couffinhal, T., et al. Mouse model of angiogenesis. *Am J Pathol* 152, 1667-1679 (1998).
23. Prasain, N., et al. Differentiation of human pluripotent stem cells to cells similar to cord-blood endothelial colony-forming cells. *Nat Biotechnol* 32, 1151-1157 (2014).
24. Perez-Simon, J. A., et al. Clinical significance of CD34+ cell dose in long-term engraftment following autologous peripheral blood stem cell transplantation. *Bone Marrow Transplant* 24, 1279-1283 (1999).
25. Hauser, I. A., Johnson, D. R. & Madri, J. A. Differential induction of VCAM-1 on human iliac venous and arterial endothelial cells and its role in adhesion. *J Immunol* 151, 5172-5185 (1993).
26. Kalogeris, T. J., et al. Differential monocyte adhesion and adhesion molecule expression in venous and arterial endothelial cells. *Am J Physiol* 276, L9-L19 (1999).
27. Orlova, V. V., et al. Functionality of endothelial cells and pericytes from human pluripotent stem cells demonstrated in cultured vascular plexus and zebrafish xenografts. *Arterioscler Thromb Vasc Biol* 34, 177-186 (2014).
28. Rufaihah, A. J., et al. Human induced pluripotent stem cell-derived endothelial cells exhibit functional heterogeneity. *Am J Transl Res* 5, 21-35 (2013).
29. Kusuma, S., Facklam, A. & Gerecht, S. Characterizing human pluripotent-stem-cell-derived vascular cells for tissue engineering applications. *Stem Cells Dev* 24, 451-458 (2015).
30. Wang, Z. Z., et al. Endothelial cells derived from human embryonic stem cells form durable blood vessels in vivo. *Nat Biotechnol* 25, 317-318 (2007).
31. James, D., et al. Expansion and maintenance of human embryonic stem cell-derived endothelial cells by TGFbeta inhibition is Id1 dependent. *Nat Biotechnol* 28, 161-166 (2010).
32. Salvagiotto, G., et al. A defined, feeder-free, serum-free system to generate in vitro hematopoietic progenitors and differentiated blood cells from hESCs and hiPSCs. *PLoS One* 6, e17829 (2011).
33. Levenberg, S., Ferreira, L. S., Chen-Konak, L., Kraehenbuehl, T. P. & Langer, R. Isolation, differentiation and characterization of vascular cells derived from human embryonic stem cells. *Nat Protoc* 5, 1115-1126 (2010).
34. Lian, X., Zhang, J., Zhu, K., Kamp, T. J. & Palecek, S. P. Insulin inhibits cardiac mesoderm, not mesendoderm, formation during cardiac differentiation of human pluripotent stem cells and modulation of canonical Wnt signaling can rescue this inhibition. *Stem Cells* 31, 447-457 (2013).
35. Yamamizu, K., et al. Convergence of Notch and beta-catenin signaling induces arterial fate in vascular progenitors. *J Cell Biol* 189, 325-338 (2010).
36. Bai, H., et al. BMP4 regulates vascular progenitor development in human embryonic stem cells through a Smad-dependent pathway. *J Cell Biochem* 109, 363-374 (2010).
37. Jaitin, D. A., et al. Massively parallel single-cell RNA-seq for marker-free decomposition of tissues into cell types. *Science* 343, 776-779 (2014).
38. Treutlein, B., et al. Reconstructing lineage hierarchies of the distal lung epithelium using single-cell RNA-seq. *Nature* 509, 371-375 (2014).

39. Trapnell, C., et al. The dynamics and regulators of cell fate decisions are revealed by pseudotemporal ordering of single cells. *Nat Biotechnol* 32, 381-386 (2014).
40. Buettner, F., et al. Computational analysis of cell-to-cell heterogeneity in single-cell RNA-sequencing data reveals hidden subpopulations of cells. *Nat Biotechnol* 33, 155-160 (2015).
41. Picelli, S., et al. Smart-seq2 for sensitive full-length transcriptome profiling in single cells. *Nat Methods* 10, 1096-1098 (2013).
42. Bae, H., et al. Building vascular networks. *Sci Transl Med* 4, 160 ps123 (2012).
43. Yu, J., et al. Induced pluripotent stem cell lines derived from human somatic cells. *Science* 318, 1917-1920 (2007).
44. Takahashi, K., et al. Induction of pluripotent stem cells from adult human fibroblasts by defined factors. *Cell* 131, 861-872 (2007).
45. Riolobos, L., et al. HLA engineering of human pluripotent stem cells. *Mol Ther* 21, 1232-1241 (2013).
46. de Rham, C. & Villard, J. Potential and limitation of HLA-based banking of human pluripotent stem cells for cell therapy. *J Immunol Res* 2014, 518135 (2014).

The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

TABLE 4

| Genes Enriched in P1 (arterial endothelial cells) vs. P3 (venous cells) | | | | |
|---|---|---|---|---|
| SYMBOL | Average Venous | Average arterial | Arterial/Venous | p |
| EFNB2 | 3.385 | 132.8169231 | 39.2369049 | 9.19431E−05 |
| ZFP91 | 3.728333333 | 40.26538462 | 10.79983494 | 0.000240266 |
| ABI1 | 10.46833333 | 103.5061538 | 9.887548529 | 0.000275893 |
| RB1CC1 | 1.223333333 | 26.68538462 | 21.8136659 | 0.000475352 |
| PAM16 | 1.233333333 | 109.8853846 | 89.0962578 | 0.000478996 |
| NDUFB2 | 68.985 | 204.7292308 | 2.967735461 | 0.000997087 |
| ECE2 | 32.285 | 241.0869231 | 7.467459287 | 0.001219051 |
| GLOD4 | 29.72 | 115.0207692 | 3.870147013 | 0.001231445 |
| ATP6V1H | 9.261666667 | 96.89230769 | 10.4616492 | 0.001476268 |
| UQCR11 | 400.9133333 | 867.3530769 | 2.163442831 | 0.001500257 |
| BCR | 0.273333333 | 17.03230769 | 62.31332083 | 0.001570238 |
| KLF7 | 6.853333333 | 59.80615385 | 8.726578869 | 0.001641459 |
| YES1 | 5.766666667 | 44.61384615 | 7.736505113 | 0.001805012 |
| GPX4 | 195.8316667 | 519.4053846 | 2.652305388 | 0.001808462 |
| CRAMP1L | 2.33 | 12.18153846 | 5.228128095 | 0.001919003 |
| PDLIM7 | 22.71166667 | 104.6307692 | 4.606917263 | 0.002007834 |
| SUV420H2 | 0.21 | 42.26923077 | 201.2820513 | 0.002058135 |
| CLTA | 9.336666667 | 93.24230769 | 9.986680581 | 0.0021114 |
| SIK3 | 0.288333333 | 9.756923077 | 33.83903957 | 0.002112886 |
| APOOL | 28.395 | 227.7223077 | 8.019803053 | 0.002179598 |
| 2410004B18RIK | 0.103333333 | 16.97615385 | 164.2853598 | 0.002200093 |
| PMPCA | 5.285 | 89.88615385 | 17.00778692 | 0.002332837 |
| SLC20A1 | 13.90833333 | 141.1692308 | 10.14997465 | 0.002452212 |
| CRYZ | 3.031666667 | 81.01 | 26.72127543 | 0.002540742 |
| STIP1 | 93.86166667 | 275.8192308 | 2.93857163 | 0.002676347 |
| 2310033P09RIK | 1.333333333 | 40.97461538 | 30.73096154 | 0.002701952 |
| SNRPN | 1.75 | 34.89384615 | 19.93934066 | 0.002947216 |
| SNURF | 1.75 | 34.89384615 | 19.93934066 | 0.002947216 |
| PKIG | 27.89166667 | 135.9292308 | 4.873471076 | 0.002989368 |
| ZFP69 | 1.728333333 | 74.69538462 | 43.21815889 | 0.003117547 |
| ZEB1 | 19.37 | 42.88769231 | 2.214129701 | 0.003365306 |
| NFKB1 | 4.178333333 | 28.84 | 6.902273634 | 0.003383717 |
| UBQLN1 | 8.751666667 | 82.31230769 | 9.405329388 | 0.003450139 |
| SCP2 | 40.35 | 131.2307692 | 3.252311505 | 0.003458867 |
| NFAT5 | 1.718333333 | 12.03384615 | 7.003208237 | 0.00356317 |
| GALNT7 | 2.171666667 | 24.92846154 | 11.47895389 | 0.003740709 |
| SLC11A1 | 6.113333333 | 15.63692308 | 2.557839107 | 0.003873468 |
| MAPK7 | 4.216666667 | 32.58384615 | 7.727394345 | 0.00388953 |
| DNAJA2 | 43.11333333 | 155.7569231 | 3.612732095 | 0.004169191 |
| 3200002M19RIK | 31.69166667 | 128.7215385 | 4.061684096 | 0.004182439 |
| MYCT1 | 19.67166667 | 109.9984615 | 5.591720488 | 0.004228163 |
| UNC5B | 0.413333333 | 53.98923077 | 130.6191067 | 0.004302974 |
| NOTCH1 | 6.468333333 | 25.01153846 | 3.86676709 | 0.004390574 |
| VCP | 87.10333333 | 236.8469231 | 2.719148786 | 0.004391778 |
| MTX2 | 3.993333333 | 42.71384615 | 10.69628869 | 0.004393955 |
| MYO6 | 4.123333333 | 22.79769231 | 5.528947205 | 0.004450296 |
| EIF1A | 51.38666667 | 182.0284615 | 3.54232865 | 0.004523565 |
| SFT2D1 | 29.595 | 145.1507692 | 4.904570679 | 0.004672191 |
| HNRPDL | 89.60333333 | 201.6476923 | 2.250448558 | 0.004872772 |
| OS9 | 0.843333333 | 18.93846154 | 22.45667376 | 0.005041053 |
| OSBPL11 | 1.883333333 | 67.16923077 | 35.66507828 | 0.005042374 |
| TMEM2 | 46.21 | 126.8084615 | 2.744177917 | 0.005122916 |
| NCLN | 5.511666667 | 53.11923077 | 9.637598567 | 0.00512415 |
| CCNH | 26.70166667 | 91.59307692 | 3.430238197 | 0.005293571 |
| PODXL | 2.241666667 | 22.92230769 | 10.22556477 | 0.005298181 |

TABLE 4-continued

Genes Enriched in P1 (arterial endothelial cells) vs. P3 (venous cells)

| SYMBOL | Average Venous | Average arterial | Arterial/Venous | p |
|---|---|---|---|---|
| CPSF2 | 11.525 | 69.92 | 6.06681128 | 0.005372826 |
| RERE | 2.495 | 10.02230769 | 4.016956991 | 0.005444336 |
| EIF4E2 | 63.23833333 | 151.6823077 | 2.398581678 | 0.005508351 |
| CSGALNACT1 | 1.436666667 | 27.72384615 | 19.29734071 | 0.005582996 |
| STAG2 | 16.92666667 | 99.05769231 | 5.852167722 | 0.005604699 |
| CATSPER2 | 0 | 4.33 | #DIV/0! | 0.005764138 |
| ORC4 | 29.08833333 | 125.2469231 | 4.305744219 | 0.005852601 |
| FNTA | 11.80333333 | 66.92307692 | 5.669845546 | 0.006003204 |
| MDM2 | 2.74 | 52.58384615 | 19.19118473 | 0.006038551 |
| AAAS | 4.686666667 | 83.18307692 | 17.74887843 | 0.006204517 |
| CCNG2 | 6.808333333 | 77.16 | 11.33317013 | 0.006289792 |
| XPNPEP1 | 42.52166667 | 156.0361538 | 3.669568154 | 0.006315041 |
| ABCA1 | 1.843333333 | 31.11153846 | 16.87786897 | 0.006324339 |
| CENPB | 3.355 | 24.35076923 | 7.258053422 | 0.006437385 |
| ATP6V1B2 | 15.295 | 154.7784615 | 10.11954636 | 0.006463226 |
| 1810011O10RIK | 13.18333333 | 116.0692308 | 8.804240008 | 0.00664935 |
| PALM | 9.896666667 | 56.17153846 | 5.675803819 | 0.006659886 |
| 1110057K04RIK | 15.285 | 106.5630769 | 6.97174203 | 0.006710143 |
| TMED10 | 86.775 | 189.76 | 2.186804955 | 0.007271129 |
| RELL1 | 6.05 | 54.70769231 | 9.04259377 | 0.007359743 |
| MICALL1 | 0.476666667 | 10.91461538 | 22.89779451 | 0.007489279 |
| CYFIP1 | 37.99833333 | 86.40923077 | 2.274026864 | 0.007616271 |
| GMFG | 1.781666667 | 45.36538462 | 25.46233 | 0.007680945 |
| MMGT1 | 11.83833333 | 57.67461538 | 4.87185263 | 0.007898165 |
| MRPL19 | 3.635 | 29.56461538 | 8.133319225 | 0.007954454 |
| ZFP770 | 0.115 | 12.44153846 | 108.187291 | 0.008008639 |
| HEY1 | 1.525 | 49.74769231 | 32.62143758 | 0.008135942 |
| AI462493 | 19.63166667 | 68.19 | 3.473469734 | 0.008317939 |
| MAP3K3 | 4.02 | 48.54923077 | 12.07692308 | 0.008461151 |
| ARL8A | 4.375 | 16.96153846 | 3.876923077 | 0.009161649 |
| PTPRG | 2.28 | 19.35153846 | 8.487516869 | 0.009360361 |
| KIF1C | 0.446666667 | 3.813076923 | 8.53673938 | 0.00945174 |
| SLC16A13 | 0.035 | 32.42461538 | 926.4175824 | 0.009459486 |
| TANC1 | 1.568333333 | 17.25153846 | 10.99991825 | 0.009468885 |
| CARKD | 0.571666667 | 65.80307692 | 115.1074232 | 0.009662523 |
| IRF2 | 5.738333333 | 28.24538462 | 4.922227932 | 0.009848846 |
| TMEM126A | 51.09333333 | 159.66 | 3.12486952 | 0.010061198 |
| SLC9A3R2 | 2.42 | 60.53769231 | 25.01557533 | 0.010070149 |
| RBM17 | 11.22833333 | 109.3530769 | 9.739030155 | 0.010121604 |
| NDFIP2 | 5.515 | 61.11384615 | 11.08138643 | 0.01026201 |
| WDR37 | 6.125 | 60.00307692 | 9.796420722 | 0.010282102 |
| ANKRD13A | 0.711666667 | 22.15615385 | 31.13276887 | 0.010510297 |
| CAMK2N1 | 0.038333333 | 10.04 | 261.9130435 | 0.010661901 |
| CYBA | 61.34333333 | 211.6038462 | 3.449500291 | 0.010705172 |
| 9430020K01RIK | 6.446666667 | 33.73153846 | 5.232399968 | 0.010782094 |
| PON3 | 47.42166667 | 235.8323077 | 4.973091928 | 0.010947294 |
| ZIK1 | 1.445 | 32.63846154 | 22.58717061 | 0.011011179 |
| TAF6 | 6.866666667 | 143.5169231 | 20.90052278 | 0.011094949 |
| ARPC1B | 15.71333333 | 118.2546154 | 7.525749812 | 0.011196008 |
| HERPUD1 | 0.075 | 80.46692308 | 1072.892308 | 0.011239847 |
| ZC3H7A | 19.84833333 | 94.36769231 | 4.754439112 | 0.011339573 |
| USP34 | 16.32166667 | 40.75307692 | 2.496869821 | 0.01139032 |
| VPS41 | 51.05166667 | 151.2569231 | 2.962820471 | 0.011548761 |
| PTRF | 100.8383333 | 262.8869231 | 2.607013765 | 0.011974929 |
| SPARCL1 | 26.95166667 | 141.1661538 | 5.237752292 | 0.012197776 |
| ATPAF1 | 0 | 8.841538462 | #DIV/0! | 0.012432885 |
| RTF1 | 7.266666667 | 19.70769231 | 2.712067749 | 0.012510393 |
| TRAF3IP2 | 0.021666667 | 10.25307692 | 473.2189349 | 0.012650349 |
| MPV17L | 62.90166667 | 133.8876923 | 2.128523764 | 0.012821527 |
| METTL1 | 0.608333333 | 21.49538462 | 35.33487882 | 0.012864088 |
| AP2A2 | 30.55333333 | 66.98615385 | 2.192433576 | 0.012937774 |
| BC052040 | 0.421666667 | 35.65923077 | 84.5673457 | 0.012992012 |
| OTUD6B | 1.256666667 | 134.4076923 | 106.9557233 | 0.013133609 |
| RBM27 | 6.238333333 | 20.85692308 | 3.34334861 | 0.013572071 |
| STOX2 | 4.311666667 | 16.90692308 | 3.921203651 | 0.013704227 |
| DUSP1 | 22.30833333 | 115.6538462 | 5.184333784 | 0.013959937 |
| APRT | 143.845 | 392.3446154 | 2.727551291 | 0.013992332 |
| KLF11 | 1.945 | 13.22615385 | 6.800079098 | 0.014138226 |
| MBNL1 | 54.94166667 | 162.4823077 | 2.957360371 | 0.014235892 |
| NDUFB6 | 176.9133333 | 435.2423077 | 2.460200707 | 0.01426922 |
| HS6ST1 | 0.331666667 | 18.20692308 | 54.89524546 | 0.014290794 |
| RNF103 | 0.058333333 | 3.42 | 58.62857143 | 0.014436475 |
| GPR108 | 0 | 34.85230769 | #DIV/0! | 0.014485379 |
| CABLES2 | 0.03 | 40.96384615 | 1365.461538 | 0.014513813 |
| 1110012L19RIK | 0.075 | 51.40076923 | 685.3435897 | 0.014638158 |
| FAM102B | 6.878333333 | 48.90153846 | 7.109504017 | 0.015105008 |

TABLE 4-continued

| Genes Enriched in P1 (arterial endothelial cells) vs. P3 (venous cells) | | | | |
|---|---|---|---|---|
| SYMBOL | Average Venous | Average arterial | Arterial/Venous | p |
| GIT2 | 31.37 | 66.93461538 | 2.13371423 | 0.015337561 |
| SH2D3C | 11.65166667 | 63.51 | 5.450722357 | 0.015462751 |
| NDUFAF4 | 6.903333333 | 27.92923077 | 4.045760131 | 0.015588477 |
| TACC1 | 23.90333333 | 66.06692308 | 2.763920921 | 0.015677661 |
| TMEM107 | 0 | 54.48615385 | #DIV/0! | 0.016146777 |
| MAP3K11 | 0.808333333 | 21.93384615 | 27.13465504 | 0.016217106 |
| HDHD2 | 12.73833333 | 69.06307692 | 5.421672923 | 0.016455021 |
| ST3GAL5 | 2.035 | 27.55615385 | 13.54110754 | 0.016545693 |
| TFDP2 | 1.631666667 | 8.296923077 | 5.084937534 | 0.017053524 |
| FAM70A | 72.96666667 | 231.5038462 | 3.172734301 | 0.017064899 |
| ATP6V1C1 | 21.12333333 | 70.67461538 | 3.345807893 | 0.017762152 |
| ARL4C | 0 | 10.77384615 | #DIV/0! | 0.017765223 |
| WDR1 | 118.985 | 361.9530769 | 3.042005941 | 0.017812468 |
| SPPL3 | 24.87666667 | 90.63538462 | 3.643389439 | 0.018003641 |
| GM10406 | 29.53833333 | 83.45769231 | 2.825402888 | 0.018369717 |
| RNASEK | 36.47 | 153.1953846 | 4.200586362 | 0.01843833 |
| SAT1 | 207.5716667 | 736.1584615 | 3.546526717 | 0.018518169 |
| NGFRAP1 | 163.3833333 | 366.7930769 | 2.244984659 | 0.018834065 |
| SCNM1 | 5.593333333 | 59.61384615 | 10.65801779 | 0.01890972 |
| TMEM135 | 0.041666667 | 40.40076923 | 969.6184615 | 0.018917381 |
| THBD | 4.881666667 | 38.83615385 | 7.955511201 | 0.018990321 |
| PIGC | 4.391666667 | 45.81769231 | 10.43287111 | 0.01906959 |
| FAM108B | 2.291666667 | 30.18769231 | 13.17281119 | 0.019131469 |
| GTF2A1 | 152.4783333 | 318.5053846 | 2.088856677 | 0.019181905 |
| KLF3 | 16.465 | 83.83461538 | 5.091686328 | 0.019245785 |
| CELSR1 | 0.176666667 | 9.797692308 | 55.4586357 | 0.019332519 |
| BAG1 | 6.505 | 38.77692308 | 5.961095016 | 0.019352643 |
| OMA1 | 0.8 | 71.75 | 89.6875 | 0.019386958 |
| WTAP | 53.74333333 | 133.7023077 | 2.487793358 | 0.019456377 |
| SRPRB | 13.555 | 97.11846154 | 7.164770309 | 0.019611167 |
| GOT1 | 3.796666667 | 55.56615385 | 14.63551023 | 0.019997176 |
| UBE2J1 | 8.225 | 31.62076923 | 3.844470423 | 0.020059233 |
| LNPEP | 0.87 | 4.605384615 | 5.293545535 | 0.020273547 |
| CLK2 | 7.611666667 | 49.52307692 | 6.506206734 | 0.020375008 |
| PSG25 | 0.573333333 | 1.700769231 | 2.966457961 | 0.020531763 |
| PLK2 | 269.0066667 | 586.1761538 | 2.179039505 | 0.02053319 |
| GNGT1 | 0.228333333 | 2.098461538 | 9.190342504 | 0.020576308 |
| BC004004 | 1.505 | 63.48615385 | 42.18349093 | 0.020608049 |
| PRSS23 | 0.18 | 38.21153846 | 212.2863248 | 0.020670808 |
| TMEM179B | 0.498333333 | 48.33923077 | 97.00180087 | 0.020676696 |
| POFUT2 | 8.811666667 | 76.23692308 | 8.651816502 | 0.020698889 |
| PDCD7 | 0.131666667 | 34.84153846 | 264.6192795 | 0.020842697 |
| MYO10 | 24.63833333 | 75.11153846 | 3.048564099 | 0.021072143 |
| ZFP830 | 3.733333333 | 13.74615385 | 3.682005495 | 0.02125756 |
| CUL1 | 53.66166667 | 151.5253846 | 2.823717451 | 0.021439414 |
| PHLPP2 | 0.356666667 | 2.52 | 7.065420561 | 0.021609083 |
| TCF4 | 65.40666667 | 136.8769231 | 2.092705989 | 0.021644076 |
| FAM82B | 0.046666667 | 6.852307692 | 146.8351648 | 0.021781048 |
| MTHFS | 1.378333333 | 40.47230769 | 29.36322203 | 0.021829631 |
| SEC11C | 18.31 | 100.5761538 | 5.492963072 | 0.021830525 |
| CYP20A1 | 2.475 | 63.35307692 | 25.5972028 | 0.021853266 |
| GJA4 | 0 | 341.8130769 | #DIV/0! | 0.021930681 |
| MRPS17 | 53.04333333 | 152.1369231 | 2.868162944 | 0.021976091 |
| TCN2 | 0.865 | 63.31461538 | 73.19608715 | 0.022099139 |
| ERICH1 | 7.178333333 | 26.62923077 | 3.709667625 | 0.022136522 |
| CUL4A | 8.706666667 | 89.80307692 | 10.31428908 | 0.022308948 |
| GALT | 9.176666667 | 85.35846154 | 9.301684875 | 0.022314096 |
| SLC41A1 | 0.126666667 | 11.60615385 | 91.62753036 | 0.022449628 |
| PPP2R3C | 1.751666667 | 35.29384615 | 20.14872283 | 0.022578109 |
| RFTN2 | 2.033333333 | 37.20307692 | 18.29659521 | 0.022607793 |
| TNS1 | 0.323333333 | 19.85461538 | 61.40602696 | 0.022707466 |
| N4BP1 | 3.005 | 22.25307692 | 7.405350058 | 0.022840249 |
| AP1B1 | 7.47 | 45.62461538 | 6.107712903 | 0.022906176 |
| PHB | 107.2916667 | 246.0061538 | 2.29287289 | 0.022956614 |
| UBAC1 | 2.656666667 | 13.19846154 | 4.968053277 | 0.023037392 |
| RAB5C | 5.825 | 17.75153846 | 3.047474414 | 0.023133369 |
| DARS2 | 1.083333333 | 40.68538462 | 37.55573964 | 0.023179456 |
| FZD4 | 3.078333333 | 42.66692308 | 13.86039732 | 0.023271942 |
| REEP5 | 15.91833333 | 56.58 | 3.55439221 | 0.023371665 |
| ARF6 | 14.16666667 | 35.28230769 | 2.490515837 | 0.023533819 |
| NMD3 | 61.78833333 | 170.4692308 | 2.758922625 | 0.023562786 |
| MKNK2 | 16.75666667 | 66.63230769 | 3.976465548 | 0.023626939 |
| 0910001L09RIK | 0.408333333 | 26.54769231 | 65.01475667 | 0.023758909 |
| TPP1 | 12.98 | 59.35846154 | 4.573070997 | 0.02376108 |
| 3110056O03RIK | 0.93 | 18.67692308 | 20.08271299 | 0.023780867 |
| ADAM15 | 3.48 | 19.44692308 | 5.588196286 | 0.023832747 |

TABLE 4-continued

Genes Enriched in P1 (arterial endothelial cells) vs. P3 (venous cells)

| SYMBOL | Average Venous | Average arterial | Arterial/Venous | p |
|---|---|---|---|---|
| ANGPT2 | 0 | 3.886923077 | #DIV/0! | 0.023913439 |
| TRMT2B | 0.348333333 | 18.88384615 | 54.21199853 | 0.024410915 |
| XPR1 | 2.316666667 | 18.66692308 | 8.057664638 | 0.0245685 |
| LAMA4 | 38.52 | 123.1223077 | 3.196321591 | 0.024670168 |
| RBM15B | 1.35 | 10.13230769 | 7.505413105 | 0.024726345 |
| PLAG1 | 2.741666667 | 14.81923077 | 5.405190554 | 0.024945921 |
| 1110001J03RIK | 42.435 | 114.24 | 2.692117356 | 0.025236719 |
| DNAJC21 | 1.855 | 32.87076923 | 17.72009123 | 0.025455253 |
| ANKRD37 | 0 | 19.33384615 | #DIV/0! | 0.025456764 |
| HEBP1 | 0.083333333 | 2.872307692 | 34.46769231 | 0.025492603 |
| EBF1 | 9.5 | 74.50538462 | 7.842672065 | 0.02550248 |
| TOMM70A | 25.685 | 96.77769231 | 3.767868106 | 0.025592427 |
| NFRKB | 0.12 | 8.373846154 | 69.78205128 | 0.025651677 |
| RNF34 | 6.471666667 | 75.87769231 | 11.72459835 | 0.025710175 |
| TMEM161A | 0 | 6.103076923 | #DIV/0! | 0.025750694 |
| FDXR | 0 | 5.233076923 | #DIV/0! | 0.025890656 |
| HEXA | 25.26166667 | 115.6738462 | 4.5790267 | 0.025964577 |
| RHOG | 8.52 | 69.45615385 | 8.152130733 | 0.02611705 |
| MAPKAPK2 | 0.276666667 | 19.44153846 | 70.27062095 | 0.026290641 |
| A430005L14RIK | 14.65666667 | 116.7207692 | 7.963664037 | 0.026423167 |
| ECHDC1 | 3.351666667 | 50.15307692 | 14.96362315 | 0.026501523 |
| TRAF7 | 27.59833333 | 92.11923077 | 3.33785485 | 0.026596211 |
| CXCR4 | 0 | 22.95230769 | #DIV/0! | 0.026654915 |
| ZFP169 | 0.053333333 | 1.375384615 | 25.78846154 | 0.026750673 |
| FERMT2 | 35.28 | 100.5438462 | 2.849882261 | 0.026789286 |
| MYLK4 | 0.515 | 1.243846154 | 2.41523525 | 0.026929464 |
| FAM172A | 5.861666667 | 44.64769231 | 7.616893769 | 0.027185609 |
| NIT2 | 22.61 | 127.0746154 | 5.620283741 | 0.027205719 |
| GOLGA2 | 0.39 | 8.923846154 | 22.8816568 | 0.027392671 |
| ATP6V1E1 | 46.32166667 | 168.2253846 | 3.631678148 | 0.027790291 |
| 2310016C08RIK | 6.558333333 | 79.30769231 | 12.09265956 | 0.028063943 |
| LRRC47 | 0.076666667 | 18.86461538 | 246.0602007 | 0.028071959 |
| VPS13B | 0.915 | 11.73615385 | 12.82639765 | 0.028077765 |
| RFESD | 1.87 | 34.06076923 | 18.2143151 | 0.028109316 |
| STRBP | 9.725 | 27.59923077 | 2.837967174 | 0.028230906 |
| NDRG3 | 0.303333333 | 29.64692308 | 97.73710904 | 0.028272119 |
| SFT2D2 | 0.026666667 | 15.18615385 | 569.4807692 | 0.028377348 |
| WSB1 | 248.3766667 | 560.1653846 | 2.255305992 | 0.028735922 |
| MRE11A | 0.725 | 49.67230769 | 68.51352785 | 0.028793407 |
| IFNGR2 | 15.70166667 | 59.68307692 | 3.801066357 | 0.028817418 |
| 1700123O20RIK | 39.35666667 | 94.47 | 2.400355721 | 0.02904505 |
| MKI67IP | 17.88 | 83.63692308 | 4.677680262 | 0.029243856 |
| SIRT2 | 10.35166667 | 67.20692308 | 6.492377048 | 0.029404512 |
| 2510012J08RIK | 0.23 | 7.200769231 | 31.30769231 | 0.029411528 |
| TMEM188 | 2.975 | 37.80923077 | 12.70898513 | 0.02958981 |
| USP28 | 0.366666667 | 27.24538462 | 74.30559441 | 0.029612383 |
| HRSP12 | 7.301666667 | 74.51769231 | 10.20557302 | 0.029670977 |
| FCER2A | 0.435 | 1.655384615 | 3.805481874 | 0.029723822 |
| INPP5K | 0.178333333 | 49.50230769 | 277.5830338 | 0.029804456 |
| TMEM134 | 5.673333333 | 23.44769231 | 4.132965742 | 0.029850332 |
| HSDL1 | 2.213333333 | 117.4130769 | 53.04807692 | 0.029853034 |
| TRIM24 | 14.90666667 | 51.56692308 | 3.459319527 | 0.029874672 |
| 1600012H06RIK | 1.013333333 | 30.41153846 | 30.01138664 | 0.02993989 |
| MIER2 | 0.113333333 | 25.69153846 | 226.6900452 | 0.029975659 |
| EPN2 | 0.393333333 | 67.31153846 | 171.13103 | 0.030066295 |
| CKB | 6.455 | 74.98307692 | 11.61627838 | 0.030084135 |
| ATG5 | 36.51666667 | 108.35 | 2.967138293 | 0.030330758 |
| BIN3 | 1.095 | 72.92230769 | 66.59571479 | 0.030339038 |
| SIRT6 | 11.55166667 | 30.65 | 2.653296783 | 0.030360402 |
| PFKL | 6.498333333 | 72.58615385 | 11.16996469 | 0.030418381 |
| CXXC5 | 11.08666667 | 51.99923077 | 4.690249318 | 0.030572682 |
| 2700078K21RIK | 0.695 | 95.28307692 | 137.0979524 | 0.030787086 |
| SNIP1 | 0.418333333 | 7.924615385 | 18.94330371 | 0.030894971 |
| EXOC6 | 3.431666667 | 56.72615385 | 16.5302051 | 0.030922331 |
| ANGEL2 | 16.89833333 | 54.69846154 | 3.23691458 | 0.03096661 |
| PPP5C | 5.806666667 | 44.66153846 | 7.691424534 | 0.031218815 |
| ECE1 | 111.9 | 274.79 | 2.45567471 | 0.031225536 |
| STARD3NL | 19.37333333 | 86.21307692 | 4.450089999 | 0.031238384 |
| HPCAL1 | 10.92833333 | 67.22692308 | 6.15161718 | 0.031429075 |
| NDUFS2 | 73.09333333 | 241.6146154 | 3.305562961 | 0.031732727 |
| BCL6B | 43.01166667 | 120.15 | 2.79342814 | 0.031754776 |
| AP3S1 | 12.56166667 | 55.00769231 | 4.379012257 | 0.031755004 |
| PPPDE2 | 0.086666667 | 23.73307692 | 273.8431953 | 0.031827411 |
| TRIB1 | 3.995 | 18.30384615 | 4.581688649 | 0.031860429 |
| AP3S2 | 6.46 | 20.70307692 | 3.204810669 | 0.031865004 |
| TRIM35 | 14.28 | 62.37307692 | 4.36786253 | 0.031931969 |

TABLE 4-continued

Genes Enriched in P1 (arterial endothelial cells) vs. P3 (venous cells)

| SYMBOL | Average Venous | Average arterial | Arterial/Venous | p |
|---|---|---|---|---|
| UBE2M | 0.461666667 | 8.538461538 | 18.49486254 | 0.03200187 |
| GADD45GIP1 | 1.156666667 | 7.919230769 | 6.846597207 | 0.032007181 |
| GM7244 | 0.346666667 | 2.086153846 | 6.017751479 | 0.032191261 |
| DTL | 14.22166667 | 76.84615385 | 5.403456265 | 0.032255499 |
| GSTM1 | 0 | 90.04923077 | #DIV/0! | 0.032400938 |
| SSH1 | 0.678333333 | 4.932307692 | 7.271215271 | 0.032554474 |
| CARS | 3.118333333 | 40.93 | 13.12560128 | 0.032685951 |
| GM6654 | 20.50833333 | 75.04 | 3.659000406 | 0.032959343 |
| RBM41 | 5.021666667 | 20.57846154 | 4.097934591 | 0.033106439 |
| HSPA4L | 0.036666667 | 5.396153846 | 147.1678322 | 0.033300757 |
| VPS28 | 103.3033333 | 249.6053846 | 2.416237468 | 0.033470154 |
| RFK | 8.44 | 54.41615385 | 6.447411593 | 0.03351173 |
| MCCC2 | 0.193333333 | 48.14153846 | 249.0079576 | 0.033669052 |
| TADA2B | 0.238333333 | 5.889230769 | 24.71005917 | 0.033685451 |
| NDOR1 | 1.638333333 | 16.99769231 | 10.37499022 | 0.033873322 |
| USP3 | 26.95333333 | 75.01538462 | 2.783157975 | 0.033890802 |
| MAN1C1 | 3.095 | 29.26 | 9.453957997 | 0.033934677 |
| ANKRD54 | 0.041666667 | 30.51307692 | 732.3138462 | 0.034039372 |
| TTLL12 | 1.216666667 | 25.01769231 | 20.56248683 | 0.034336372 |
| VAC14 | 0.415 | 5.976153846 | 14.40037071 | 0.034356148 |
| CLPTM1 | 2.968333333 | 16.86 | 5.679955081 | 0.03444528 |
| 1110020G09RIK | 4.076666667 | 54.71692308 | 13.42197622 | 0.034502276 |
| MLH3 | 0.658333333 | 8.206153846 | 12.46504382 | 0.034602385 |
| SCYL2 | 0.018333333 | 1.806923077 | 98.55944056 | 0.034995114 |
| MECOM | 6.53 | 97.88538462 | 14.99010484 | 0.035000679 |
| LPCAT3 | 5.005 | 48.18384615 | 9.627142089 | 0.035029409 |
| ZFP457 | 0.336666667 | 2.023846154 | 6.011424219 | 0.035086209 |
| ZFP637 | 44.54 | 132.8969231 | 2.983765673 | 0.035138186 |
| CEP250 | 0.098333333 | 5.122307692 | 52.09126467 | 0.035266592 |
| CAMK2G | 2.091666667 | 36.67538462 | 17.53404842 | 0.035309188 |
| GRPEL2 | 1.341666667 | 15.22538462 | 11.34811276 | 0.035436744 |
| PKMYT1 | 1.156666667 | 35.49615385 | 30.68831745 | 0.035543986 |
| IFT46 | 38.585 | 94.58153846 | 2.451251483 | 0.035658758 |
| DPM3 | 45.605 | 99.79230769 | 2.188187867 | 0.035678768 |
| RASSF2 | 2.685 | 16.88923077 | 6.290216301 | 0.035699489 |
| PXK | 1.29 | 19.44692308 | 15.07513417 | 0.035717616 |
| FOXP2 | 1.498333333 | 25.56769231 | 17.0640883 | 0.035990592 |
| SLC25A1 | 3.498333333 | 48.71846154 | 13.92619196 | 0.03616713 |
| 2610002I17RIK | 9.57 | 57.04923077 | 5.961257134 | 0.036249471 |
| SLC38A7 | 0 | 2.803076923 | #DIV/0! | 0.03650076 |
| NCSTN | 19.76333333 | 70.50384615 | 3.567406619 | 0.036654248 |
| 1810048J11RIK | 0 | 25.67769231 | #DIV/0! | 0.036656075 |
| RPP40 | 7.81 | 40.37846154 | 5.170097508 | 0.036738428 |
| SMTN | 10.585 | 37.49692308 | 3.542458486 | 0.036844152 |
| MTHFD2 | 2.961666667 | 67.39230769 | 22.7548591 | 0.036927106 |
| CSAD | 2.518333333 | 22.9 | 9.093315685 | 0.03721687 |
| PLCB4 | 0.061666667 | 20.81769231 | 337.5841996 | 0.037255767 |
| MAP3K7 | 8.493333333 | 41.92692308 | 4.936450912 | 0.037295572 |
| DNAJC17 | 0.176666667 | 31.84461538 | 180.2525399 | 0.037395996 |
| 5430437P03RIK | 16.90333333 | 45.21384615 | 2.674847929 | 0.037578453 |
| CCND2 | 71.25 | 177.8453846 | 2.496075574 | 0.037648986 |
| DPM2 | 37.36666667 | 129.3623077 | 3.461970768 | 0.037677582 |
| 2310036O22RIK | 19.51333333 | 51.35307692 | 2.631691677 | 0.037728855 |
| KLHL21 | 0.893333333 | 20.34384615 | 22.77296211 | 0.038085178 |
| FAM165B | 61.485 | 142.6907692 | 2.320741144 | 0.038115442 |
| FKBP14 | 0.071666667 | 54.78 | 764.372093 | 0.038340315 |
| ARHGAP5 | 17.34333333 | 71.04461538 | 4.096364523 | 0.038370987 |
| 2310008H04RIK | 2.466666667 | 20.33923077 | 8.245634096 | 0.038383648 |
| ZFP592 | 0.285 | 20.45615385 | 71.77597841 | 0.038495223 |
| TMTC4 | 5.511666667 | 31.10307692 | 5.64313461 | 0.038498387 |
| HIGD1A | 3.58 | 19.04153846 | 5.318865492 | 0.038573935 |
| SMPDL3B | 0 | 8.326923077 | #DIV/0! | 0.038797907 |
| RCC2 | 22.76666667 | 50.06769231 | 2.199166573 | 0.039044589 |
| KBTBD2 | 8.396666667 | 77.70538462 | 9.254313372 | 0.039141354 |
| TERF1 | 2.76 | 27.59230769 | 9.997212932 | 0.039151289 |
| ACER2 | 0.85 | 10.87153846 | 12.79004525 | 0.039158693 |
| MGLL | 0.093333333 | 25.18307692 | 269.8186813 | 0.03921294 |
| SRGAP1 | 3.741666667 | 13.83384615 | 3.697241734 | 0.039355605 |
| APPL2 | 1.191666667 | 31.36461538 | 26.31995697 | 0.039489916 |
| LNX1 | 0 | 1.966153846 | #DIV/0! | 0.039521684 |
| MIPOL1 | 0.363333333 | 17.92 | 49.32110092 | 0.039567716 |
| SLC23A2 | 7.303333333 | 29.13538462 | 3.989326967 | 0.039581995 |
| PAIP2 | 219.0333333 | 454.2284615 | 2.073786919 | 0.039729082 |
| CERK | 3.871666667 | 21.01307692 | 5.427398258 | 0.039748408 |
| LAGE3 | 30.33833333 | 133.3246154 | 4.394592607 | 0.039911992 |
| NOP14 | 5.015 | 56.62 | 11.29012961 | 0.040136837 |

TABLE 4-continued

Genes Enriched in P1 (arterial endothelial cells) vs. P3 (venous cells)

| SYMBOL | Average Venous | Average arterial | Arterial/Venous | p |
|---|---|---|---|---|
| GMPPB | 11.83333333 | 66.38692308 | 5.610162514 | 0.040183033 |
| PRR5L | 22.68833333 | 63.24384615 | 2.787505156 | 0.040241287 |
| ZCWPW1 | 0.04 | 27.26846154 | 681.7115385 | 0.040286692 |
| 2510006D16RIK | 123.25 | 263.7661538 | 2.140090498 | 0.04028986 |
| PPM1E | 0 | 5.566153846 | #DIV/0! | 0.040391847 |
| PCYT1A | 2.993333333 | 15.98076923 | 5.338787048 | 0.04052893 |
| 1110034B05RIK | 12 | 84.33230769 | 7.027692308 | 0.04072132 |
| PGAP2 | 0 | 50.55923077 | #DIV/0! | 0.040730276 |
| SRGN | 0.238333333 | 33.19846154 | 139.2942442 | 0.040969616 |
| LPCAT1 | 1.751666667 | 12.03461538 | 6.870379858 | 0.041139103 |
| LYL1 | 0.573333333 | 11.66307692 | 20.34257603 | 0.041144687 |
| GM14430 | 0.275 | 8.703846154 | 31.65034965 | 0.041267689 |
| GM14434 | 0.275 | 8.703846154 | 31.65034965 | 0.041267689 |
| AGGF1 | 4.063333333 | 55.85384615 | 13.7458194 | 0.041344615 |
| GTL3 | 77.075 | 248.4761538 | 3.22382295 | 0.041361201 |
| KCNQ1 | 0.031666667 | 1.834615385 | 57.93522267 | 0.04147258 |
| ANXA11 | 0.123333333 | 1.683846154 | 13.65280665 | 0.041566921 |
| GIMAP1 | 15.75666667 | 50.43076923 | 3.200598851 | 0.041692451 |
| DNAJB9 | 0 | 28.25307692 | #DIV/0! | 0.041693969 |
| COX18 | 2.021666667 | 16.60461538 | 8.213329951 | 0.04188168 |
| PRODH | 0 | 31.34384615 | #DIV/0! | 0.041905819 |
| GM5113 | 9.601666667 | 22.49923077 | 2.343263055 | 0.041978051 |
| HINT2 | 11.93166667 | 55.91615385 | 4.686365737 | 0.042079062 |
| LYPLA2 | 2.881666667 | 35.32923077 | 12.25999911 | 0.042084923 |
| MAP3K2 | 0.046666667 | 2.787692308 | 59.73626374 | 0.042146552 |
| GALE | 23.73666667 | 96.33307692 | 4.058407959 | 0.042260317 |
| PLAT | 0.16 | 19.67230769 | 122.9519231 | 0.042532177 |
| ZFP358 | 1.115 | 21.94 | 19.67713004 | 0.042682574 |
| ZCCHC3 | 16.50166667 | 44.49923077 | 2.696650688 | 0.042818734 |
| PPP2R4 | 6.496666667 | 21.63307692 | 3.329873308 | 0.043018399 |
| AKR1B3 | 103.7033333 | 277.6669231 | 2.677512035 | 0.043535478 |
| GM10345 | 0 | 32.37153846 | #DIV/0! | 0.043551944 |
| ZHX1 | 0.88 | 22.74615385 | 25.8479021 | 0.043595271 |
| RAPGEF5 | 3.076666667 | 17.74384615 | 5.767230603 | 0.043739677 |
| 2310003L22RIK | 0 | 20.38615385 | #DIV/0! | 0.043829833 |
| FBRSL1 | 0.531666667 | 5.803076923 | 10.91487823 | 0.044093031 |
| TMOD1 | 12.35166667 | 38.17461538 | 3.090644883 | 0.044263895 |
| TBC1D23 | 2.17 | 21.87384615 | 10.08011343 | 0.044386925 |
| ELAC2 | 0.556666667 | 57.29923077 | 102.9327499 | 0.044398266 |
| SPINT2 | 0 | 25.24769231 | #DIV/0! | 0.04442694 |
| API5 | 67.80333333 | 162.0369231 | 2.389807626 | 0.044541725 |
| SKIL | 62.55166667 | 144.3038462 | 2.306954456 | 0.044578008 |
| ASS1 | 2.425 | 50.87076923 | 20.9776368 | 0.044658449 |
| ZFP809 | 0.548333333 | 6.85 | 12.49240122 | 0.044775293 |
| PECAM1 | 87.48666667 | 216.1353846 | 2.470495138 | 0.044778294 |
| LCLAT1 | 0.03 | 12.22153846 | 407.3846154 | 0.044791712 |
| LIN7C | 34.86666667 | 92.33692308 | 2.648286513 | 0.044837935 |
| DAZAP1 | 3.816666667 | 16.06538462 | 4.209271078 | 0.044855774 |
| BMP1 | 12.96666667 | 59.58846154 | 4.595511173 | 0.044873594 |
| ALAS2 | 0.033333333 | 12.3 | 369 | 0.045035951 |
| ARFGEF2 | 0.013333333 | 12.11538462 | 908.6538462 | 0.045037558 |
| KHNYN | 0 | 2.626923077 | #DIV/0! | 0.045084098 |
| ECM1 | 0 | 27.87153846 | #DIV/0! | 0.045122243 |
| MTSS1L | 0.92 | 8.325384615 | 9.049331104 | 0.045141405 |
| RIC8B | 1.546666667 | 17.55923077 | 11.35295093 | 0.045459795 |
| FAM100A | 0.071666667 | 7.908461538 | 110.3506261 | 0.045489009 |
| POP7 | 27.48833333 | 108.7146154 | 3.954936593 | 0.045527616 |
| TMEM8B | 0.453333333 | 14.72554462 | 32.48246606 | 0.04554072 |
| HECTD1 | 18.975 | 49.41769231 | 2.604357961 | 0.04578972 |
| PIH1D1 | 7.455 | 49.70076923 | 6.66676985 | 0.045985496 |
| GNE | 0.055 | 2.502307692 | 45.4965035 | 0.046063511 |
| LYSMD3 | 0.82 | 42.79846154 | 52.19324578 | 0.046070404 |
| 1110003E01RIK | 0.468333333 | 34.33153846 | 73.30577607 | 0.046077666 |
| FUT10 | 0.02 | 5.203846154 | 260.1923077 | 0.046298882 |
| PEX11B | 4.003333333 | 39.44923077 | 9.854095946 | 0.046489188 |
| RNF31 | 0.471666667 | 24.92153846 | 52.83718402 | 0.046492936 |
| OGFR | 0.033333333 | 14.2 | 426 | 0.046557415 |
| GCFC1 | 30.21166667 | 75.21 | 2.489435648 | 0.04657836 |
| WDR55 | 7.323333333 | 60.16923077 | 8.216098876 | 0.046768358 |
| FAM117A | 0 | 3.892307692 | #DIV/0! | 0.046981029 |
| EIF2B5 | 14.40833333 | 66.86153846 | 4.640476932 | 0.047035175 |
| PPFIBP2 | 0.528333333 | 13.06461538 | 24.72797865 | 0.047178928 |
| TMEM109 | 9.633333333 | 56.26846154 | 5.841016769 | 0.047417695 |
| MMP15 | 8.233333333 | 24.76538462 | 3.007941451 | 0.047597294 |
| TRMT11 | 7.843333333 | 31.60692308 | 4.029781948 | 0.048005041 |
| ALAS1 | 14.72 | 49.46384615 | 3.360315635 | 0.048187395 |

TABLE 4-continued

Genes Enriched in P1 (arterial endothelial cells) vs. P3 (venous cells)

| SYMBOL | Average Venous | Average arterial | Arterial/Venous | p |
|---|---|---|---|---|
| CCPG1 | 0.54 | 22.89076923 | 42.39031339 | 0.048240471 |
| GAK | 5.171666667 | 28.74461538 | 5.558095144 | 0.048289197 |
| RANBP6 | 1.16 | 8.937692308 | 7.704907162 | 0.048307814 |
| HOXB4 | 0.055 | 4.497692308 | 81.77622378 | 0.048345333 |
| SLC20A2 | 1.611666667 | 39.54384615 | 24.53599555 | 0.048465284 |
| MRPS5 | 18.02833333 | 51.36846154 | 2.849318381 | 0.048528808 |
| TTI1 | 0 | 8.923076923 | #DIV/0! | 0.048560674 |
| GRIA2 | 0 | 33.54692308 | #DIV/0! | 0.049032855 |
| ABCB7 | 3.866666667 | 17.84153846 | 4.614190981 | 0.049129942 |
| SLC18A2 | 3.061666667 | 55.74 | 18.20577028 | 0.049196079 |
| SARS2 | 0.663333333 | 38.67 | 58.29648241 | 0.04921158 |
| ALKBH3 | 2.72 | 32.07076923 | 11.79072398 | 0.049504769 |
| HES6 | 0 | 35.96923077 | #DIV/0! | 0.049589735 |
| MTMR9 | 0.065 | 28.03076923 | 431.2426036 | 0.049786268 |
| IRF2BP1 | 0 | 2.435384615 | #DIV/0! | 0.049878388 |
| VPS26B | 2.686666667 | 12.53692308 | 4.66634854 | 0.050007937 |
| CEP68 | 2.906666667 | 38.03923077 | 13.08689132 | 0.050119545 |
| ANKIB1 | 2.796666667 | 19.03769231 | 6.807279729 | 0.050190369 |
| UBA7 | 0.365 | 8.059230769 | 22.0800843 | 0.05025586 |
| PDZD8 | 12.44333333 | 29.49 | 2.369943745 | 0.050457696 |
| RNF14 | 15.77 | 60.10538462 | 3.811375055 | 0.050490229 |
| PTMS | 7.316666667 | 38.12538462 | 5.210758717 | 0.050512605 |
| ARMC5 | 2.638333333 | 18.70230769 | 7.088682638 | 0.050531575 |
| TET1 | 0.811666667 | 12.63384615 | 15.56531354 | 0.050672764 |
| FZD10 | 0.533333333 | 3.283846154 | 6.157211538 | 0.050692702 |
| SAMM50 | 8.068333333 | 42.92461538 | 5.320134111 | 0.050866203 |
| TFAM | 15.87 | 42.34923077 | 2.668508555 | 0.050951714 |
| GPATCH2 | 1.16 | 19.14153846 | 16.50132626 | 0.051154694 |
| REPIN1 | 2.006666667 | 14.55461538 | 7.25313059 | 0.051272867 |
| 2010012O05RIK | 6.165 | 19.39153846 | 3.145423919 | 0.051402534 |
| FAM78B | 0.043333333 | 5.774615385 | 133.260355 | 0.051446212 |
| TMEM165 | 8.953333333 | 40.03846154 | 4.471905607 | 0.05145031 |
| NTS | 0 | 85.65692308 | #DIV/0! | 0.051571632 |
| ST7L | 3.53 | 21.37230769 | 6.0544781 | 0.051624534 |
| AMN1 | 0.195 | 21.10384615 | 108.2248521 | 0.051674438 |
| NSUN6 | 0 | 1.520769231 | #DIV/0! | 0.051720659 |
| ARFGAP1 | 3.646666667 | 45.61846154 | 12.50963296 | 0.052127566 |
| SLC4A7 | 9.286666667 | 32.87307692 | 3.539814457 | 0.052423429 |
| PELI2 | 1.78 | 19.47846154 | 10.94295592 | 0.052510364 |
| NAGK | 6.618333333 | 57.91769231 | 8.751099316 | 0.05266822 |
| LGMN | 11.48833333 | 50.06846154 | 4.358200627 | 0.052749415 |
| GCDH | 2.618333333 | 29.30769231 | 11.1932625 | 0.052854704 |
| CPNE1 | 8.236666667 | 41.49307692 | 5.037605454 | 0.052940324 |
| VMA21 | 2.865 | 13.77230769 | 4.8070882 | 0.052973039 |
| D830031N03RIK | 0.346666667 | 6.445384615 | 18.59245562 | 0.05308216 |
| UCK2 | 4.32 | 27.92846154 | 6.464921652 | 0.053105139 |
| SRP68 | 9.048333333 | 70.17 | 7.755019341 | 0.053137657 |
| SLC25A30 | 0 | 21.66076923 | #DIV/0! | 0.053274355 |
| ZFP558 | 0.768333333 | 20.02846154 | 26.06741198 | 0.053322948 |
| PHTF1 | 0.896666667 | 31.32846154 | 34.93880469 | 0.05347776 |
| HERC6 | 1.573333333 | 10.14153846 | 6.44589309 | 0.053846185 |
| RCOR1 | 6.696666667 | 63.35615385 | 9.460849255 | 0.053868948 |
| FBXL4 | 1.75 | 32.24461538 | 18.42549451 | 0.053889135 |
| FBXL19 | 1.071666667 | 12.73076923 | 11.87941141 | 0.054084426 |
| KDM6A | 5.525 | 17.71076923 | 3.205569092 | 0.054545687 |
| RAPH1 | 2.233333333 | 39.28076923 | 17.58840413 | 0.054784469 |
| TANC2 | 0.118333333 | 10.27923077 | 86.86673889 | 0.05487343 |
| ABCE1 | 55.66166667 | 200.5246154 | 3.602562183 | 0.054974313 |
| RMND1 | 0.41 | 29.31615385 | 71.50281426 | 0.055302636 |
| C1QTNF6 | 0 | 1.048461538 | #DIV/0! | 0.055399921 |
| MAF1 | 17.76666667 | 100.4276923 | 5.652590561 | 0.055451124 |
| ZFP869 | 6.383333333 | 55.8 | 8.74151436 | 0.055502064 |
| FAM125B | 0.116666667 | 3.541538462 | 30.35604396 | 0.055627209 |
| RNF40 | 10.07833333 | 31.58076923 | 3.133530931 | 0.055641091 |
| ZSCAN12 | 0.526666667 | 9.412307692 | 17.8714703 | 0.055665583 |
| FAM49B | 2.506666667 | 10.73923077 | 4.284267594 | 0.05577894 |
| SUCLA2 | 73.88833333 | 148.5692308 | 2.010726512 | 0.055789996 |
| CCDC126 | 0 | 20.03538462 | #DIV/0! | 0.055798969 |
| SLC25A12 | 0.403333333 | 25.63384615 | 63.55499046 | 0.055851423 |
| ERCC2 | 0.231666667 | 3.83 | 16.5323741 | 0.055878132 |
| UBOX5 | 6.57 | 36.27461538 | 5.521250439 | 0.055904215 |
| NOS3 | 0.686666667 | 12.66846154 | 18.44921583 | 0.055905624 |
| CERCAM | 0.83 | 3.07 | 3.698795181 | 0.055944772 |
| NCOA7 | 3.856666667 | 56.52846154 | 14.65733661 | 0.055945052 |
| BCL2 | 2.008333333 | 16.59230769 | 8.261729971 | 0.056008723 |
| MAGEB18 | 0.2 | 1.033846154 | 5.169230769 | 0.05608565 |

TABLE 4-continued

Genes Enriched in P1 (arterial endothelial cells) vs. P3 (venous cells)

| SYMBOL | Average Venous | Average arterial | Arterial/Venous | p |
|---|---|---|---|---|
| GTPBP5 | 0.228333333 | 25.01846154 | 109.5699045 | 0.056248586 |
| CPEB4 | 0.836666667 | 24.53692308 | 29.32699969 | 0.056407253 |
| HAX1 | 30.27666667 | 126.9284615 | 4.19228652 | 0.056534504 |
| GLCCI1 | 0.158333333 | 11.92076923 | 75.28906883 | 0.056835057 |
| CCL24 | 0.786666667 | 2.102307692 | 2.672425033 | 0.056862408 |
| ZFP808 | 12.35166667 | 132.1638462 | 10.700082 | 0.057000052 |
| ADIPOR2 | 5.226666667 | 37.31615385 | 7.139570251 | 0.057117537 |
| RAB35 | 0.408333333 | 26.87692308 | 65.82103611 | 0.05715073 |
| DLL4 | 12.24833333 | 35 | 2.857531637 | 0.057278061 |
| E130311K13RIK | 3.908333333 | 14.12538462 | 3.614170904 | 0.057379198 |
| APOBEC3 | 2.563333333 | 42.88615385 | 16.73061919 | 0.057549875 |
| SLC25A24 | 18.32166667 | 54.09307692 | 2.952410275 | 0.057583665 |
| 2610101N10RIK | 37.03666667 | 78.11538462 | 2.109136476 | 0.057642267 |
| ZMYM5 | 5.008333333 | 24.55153846 | 4.902137463 | 0.057664765 |
| CCDC43 | 43.24833333 | 111.7946154 | 2.584946211 | 0.057668463 |
| VKORC1L1 | 0.063333333 | 8.742307692 | 138.0364372 | 0.057806041 |
| IL13RA1 | 0.016666667 | 7.85 | 471 | 0.05788107 |
| MSX1 | 0.05 | 8.469230769 | 169.3846154 | 0.057982811 |
| HMCN1 | 2.816666667 | 8.090769231 | 2.872462449 | 0.057997308 |
| TAF6L | 0.068333333 | 5.810769231 | 85.03564728 | 0.058254094 |
| STAT3 | 8.168333333 | 33.56615385 | 4.109302654 | 0.058254632 |
| ETF1 | 27.52 | 79.39615385 | 2.88503466 | 0.058342227 |
| MFSD5 | 7.451666667 | 41.13769231 | 5.520602859 | 0.05866687 |
| YY2 | 0.06 | 6.092307692 | 101.5384615 | 0.058761486 |
| SLC7A1 | 6.753333333 | 20.11769231 | 2.978927785 | 0.058828552 |
| RNF185 | 7.015 | 80.98538462 | 11.54460223 | 0.05890966 |
| CYP26B1 | 3.913333333 | 26.37230769 | 6.739090552 | 0.058910796 |
| DDX3Y | 7.835 | 46.02769231 | 5.874625693 | 0.05895258 |
| IMP4 | 42.61166667 | 106.0707692 | 2.489242443 | 0.059341979 |
| SERTAD1 | 7.193333333 | 52.86538462 | 7.349219363 | 0.059362584 |
| PGCP | 2.616666667 | 41.60230769 | 15.89897109 | 0.059751388 |
| PFKP | 6.793333333 | 30.24538462 | 4.452215596 | 0.059823579 |
| IPMK | 1.013333333 | 8.623076923 | 8.509615385 | 0.059838428 |
| VEGFA | 0.476666667 | 2.713076923 | 5.691769769 | 0.059863499 |
| E2F2 | 0.098333333 | 11.65615385 | 118.5371578 | 0.060057838 |
| ARRDC1 | 5.116666667 | 40.29538462 | 7.875319469 | 0.060236708 |
| PLEKHG5 | 1.643333333 | 9.620769231 | 5.854423467 | 0.060363717 |
| PHF13 | 0.523333333 | 19.32230769 | 36.92160706 | 0.060421909 |
| COQ4 | 19.20166667 | 68.86692308 | 3.586507581 | 0.06045569 |
| ALDH4A1 | 0.32 | 3.928461538 | 12.27644231 | 0.060509956 |
| 4933403F05RIK | 9.585 | 27.94307692 | 2.915292324 | 0.06051212 |
| PAPD4 | 3.011666667 | 62.82461538 | 20.86041463 | 0.060657403 |
| ZFP647 | 0.058333333 | 33.44923077 | 573.4153846 | 0.06068685 |
| LSM4 | 15.04 | 58.13923077 | 3.865640344 | 0.060767276 |
| CAPG | 2.843333333 | 72.77769231 | 25.59590585 | 0.060879157 |
| RNF2 | 44.29333333 | 98.41384615 | 2.221865882 | 0.060931171 |
| LIN54 | 0.211666667 | 16.89307692 | 79.80981224 | 0.060934324 |
| CDC37L1 | 0.216666667 | 16.32538462 | 75.34792899 | 0.061058673 |
| 2610002M06RIK | 0.818333333 | 6.697692308 | 8.184552718 | 0.061092923 |
| ARMCX3 | 8.833333333 | 36.69461538 | 4.154107402 | 0.061330159 |
| TTC37 | 5.881666667 | 29.13384615 | 4.953331735 | 0.061347448 |
| PARP6 | 1.473333333 | 23.45230769 | 15.9178559 | 0.061450809 |
| RBM7 | 70.67 | 157.5892308 | 2.229931099 | 0.061570105 |
| ADAT2 | 0 | 28.44230769 | #DIV/0! | 0.061838009 |
| PTPMT1 | 0 | 14.89461538 | #DIV/0! | 0.061985931 |
| RTEL1 | 0.345 | 25.66 | 74.37681159 | 0.06221779 |
| DCP1B | 0.226666667 | 2.858461538 | 12.61085973 | 0.062376621 |
| CRIM1 | 0.54 | 6.808461538 | 12.60826211 | 0.062729098 |
| STK35 | 1.875 | 36.02230769 | 19.21189744 | 0.062962924 |
| IL4RA | 0.056666667 | 6.492307692 | 114.5701357 | 0.062976524 |
| CCNT2 | 13.215 | 43.71923077 | 3.308303501 | 0.063205018 |
| BAG2 | 20.57833333 | 94.91230769 | 4.612244644 | 0.063265705 |
| SORBS2 | 0.226666667 | 9.810769231 | 43.28280543 | 0.063290001 |
| PHF10 | 3.685 | 32.13153846 | 8.719549108 | 0.06337384 |
| MOGAT2 | 0.05 | 52.81 | 1056.2 | 0.063468062 |
| ARIH2 | 2.333333333 | 18.13153846 | 7.770659341 | 0.063470474 |
| PACSIN2 | 13.56 | 64.47 | 4.754424779 | 0.063478507 |
| YIPF1 | 3.13 | 37.29615385 | 11.9157041 | 0.063554766 |
| COG6 | 3.126666667 | 38.22307692 | 12.22486469 | 0.063747439 |
| SLC7A6 | 4.208333333 | 15.10076923 | 3.588301599 | 0.063782233 |
| 2310001A20RIK | 2.845 | 55.87230769 | 19.63877248 | 0.064090499 |
| D630042P16RIK | 0 | 12.96307692 | #DIV/0! | 0.064146809 |
| STK4 | 3.62 | 15.75769231 | 4.352953676 | 0.064174954 |
| FXC1 | 35.825 | 94.07769231 | 2.626034677 | 0.064185248 |
| ZFP369 | 2.483333333 | 10.37846154 | 4.179246257 | 0.064303184 |
| KIF3B | 0.043333333 | 4.393076923 | 101.3786982 | 0.06441931 |

TABLE 4-continued

Genes Enriched in P1 (arterial endothelial cells) vs. P3 (venous cells)

| SYMBOL | Average Venous | Average arterial | Arterial/Venous | p |
|---|---|---|---|---|
| SEC24D | 5.013333333 | 32.95538462 | 6.573547463 | 0.06486327 |
| CEP135 | 0.323333333 | 13.27769231 | 41.06502776 | 0.064872529 |
| PCGF1 | 0 | 22.00692308 | #DIV/0! | 0.064899955 |
| ARL13B | 2.111666667 | 12.52076923 | 5.929330338 | 0.064987893 |
| ZFP810 | 0.08 | 21.91153846 | 273.8942308 | 0.065100666 |
| ESYT1 | 0 | 30.88384615 | #DIV/0! | 0.06518411 |
| CCZ1 | 17.35666667 | 80.20538462 | 4.621013133 | 0.065245485 |
| PLEKHJ1 | 10.81333333 | 37.43153846 | 3.461609599 | 0.065324885 |
| NOL12 | 16.005 | 57.33538462 | 3.582342057 | 0.065352199 |
| NEURL2 | 0 | 3.716153846 | #DIV/0! | 0.065511114 |
| SLC35B2 | 11.93833333 | 56.23384615 | 4.710359862 | 0.065662923 |
| STX3 | 0.106666667 | 15.75076923 | 147.6634615 | 0.065770952 |
| ZFP524 | 1.28 | 27.75846154 | 21.68629808 | 0.065812321 |
| CAPN7 | 8.455 | 55.77076923 | 6.596187963 | 0.065933189 |
| REXO4 | 18.115 | 65.04538462 | 3.590691947 | 0.066064674 |
| TMPPE | 1.016666667 | 7.921538462 | 7.791677175 | 0.06625231 |
| PGGT1B | 10.61 | 47.86692308 | 4.511491336 | 0.066290551 |
| CMKLR1 | 0.501666667 | 4.066923077 | 8.106823409 | 0.066320641 |
| LEPR | 10.915 | 25.52769231 | 2.338771627 | 0.066591229 |
| MLL5 | 16.92333333 | 38.43615385 | 2.271192861 | 0.066632225 |
| CPE | 24.92833333 | 147.0984615 | 5.900854244 | 0.066656079 |
| 3110002H16RIK | 10.475 | 55.47307692 | 5.295759133 | 0.066660336 |
| FAM18B | 35.45166667 | 106.0323077 | 2.990897683 | 0.066824071 |
| MYLK | 6.318333333 | 16.80461538 | 2.659659517 | 0.066907628 |
| NPR2 | 0 | 12.93615385 | #DIV/0! | 0.067048221 |
| MAPRE2 | 29.54 | 75.37307692 | 2.551559815 | 0.067252831 |
| POLR3H | 1.106666667 | 10.86384615 | 9.816728452 | 0.067397529 |
| ZDHHC7 | 0.008333333 | 9.286923077 | 1114.430769 | 0.067424431 |
| FAT1 | 2.761666667 | 11.12384615 | 4.027946706 | 0.067442384 |
| D19ERTD386E | 0.603333333 | 23.59461538 | 39.10709732 | 0.067464044 |
| EBPL | 1.13 | 11.62076923 | 10.28386658 | 0.067566323 |
| ILKAP | 0.436666667 | 33.9 | 77.63358779 | 0.067683201 |
| PIK3C2B | 6.925 | 21.25076923 | 3.068703138 | 0.067776036 |
| NINJ1 | 16.98 | 91.41923077 | 5.383935852 | 0.067889903 |
| APLP1 | 0.921666667 | 23.67692308 | 25.68924746 | 0.06789714 |
| KBTBD7 | 0.371666667 | 9.033846154 | 24.30631252 | 0.067953384 |
| MTPAP | 13.205 | 43.51153846 | 3.295080535 | 0.067985483 |
| CCDC111 | 0.971666667 | 18.11384615 | 18.64203721 | 0.068052146 |
| AIFM1 | 12.335 | 93.59307692 | 7.587602507 | 0.068283362 |
| CGRRF1 | 6.303333333 | 72.53692308 | 11.50770858 | 0.068447187 |
| PLAU | 39.32 | 123.4115385 | 3.138645434 | 0.068622405 |
| TEX261 | 6.128333333 | 40.55307692 | 6.617309261 | 0.068722977 |
| NNT | 17.38833333 | 50.90615385 | 2.927603979 | 0.068756325 |
| CTXN1 | 1.228333333 | 20.71230769 | 16.86212295 | 0.069009229 |
| NGRN | 0.335 | 36.52538462 | 109.0309989 | 0.069080224 |
| AACS | 3.008333333 | 41.58153846 | 13.82211805 | 0.069255291 |
| NAMPT | 2.465 | 27.80076923 | 11.27820253 | 0.069272222 |
| KLHL5 | 4.145 | 31.6 | 7.623642943 | 0.069427954 |
| FBXL17 | 4.44 | 9.891538462 | 2.227823978 | 0.06957291 |
| SLC25A39 | 29.67333333 | 120.4469231 | 4.059096487 | 0.06964896 |
| GGH | 6.396666667 | 31.18846154 | 4.875736562 | 0.069772486 |
| ZADH2 | 0.131666667 | 5.839230769 | 44.34858812 | 0.069834529 |
| IGFBP3 | 37.60833333 | 113.7 | 3.02326612 | 0.069870412 |
| PABPC1L | 0.125 | 2.477692308 | 19.82153846 | 0.07007761 |
| TMEM175 | 0.411666667 | 27.98923077 | 67.99003426 | 0.070133209 |
| SSFA2 | 6.608333333 | 50.53307692 | 7.646871666 | 0.070436849 |
| GM7616 | 4.268333333 | 11.64153846 | 2.727420178 | 0.0704728 |
| DNAJC25 | 0 | 10.49923077 | #DIV/0! | 0.070482756 |
| AATF | 2.943333333 | 42.88615385 | 14.5706072 | 0.070515129 |
| IKBKG | 5.018333333 | 23.21230769 | 4.625501367 | 0.070677919 |
| BEND4 | 0.03 | 10.33769231 | 344.5897436 | 0.070719978 |
| WDFY2 | 0 | 3.26 | #DIV/0! | 0.070900974 |
| SH3PXD2B | 6.605 | 24.56615385 | 3.71932685 | 0.07098515 |
| MPDU1 | 0.543333333 | 13.54923077 | 24.93723454 | 0.07119844 |
| 4933439F18RIK | 27.53 | 61.72846154 | 2.242225265 | 0.071330049 |
| ROCK2 | 22.725 | 55.42692308 | 2.439028518 | 0.071419743 |
| PYGO2 | 2.42 | 51.32769231 | 21.20979021 | 0.071514864 |
| PRMT3 | 4.151666667 | 30.64461538 | 7.381280301 | 0.071527724 |
| PDCL3 | 62.66333333 | 138.4676923 | 2.209708372 | 0.071574233 |
| ZFP229 | 0.11 | 2.258461538 | 20.53146853 | 0.071632948 |
| ANKMY2 | 8.108333333 | 51.18769231 | 6.312973358 | 0.071726681 |
| PIGH | 5.813333333 | 37.59846154 | 6.467625265 | 0.07174143 |
| SMAD2 | 16.53 | 63.96615385 | 3.869700777 | 0.071751137 |
| RAD17 | 3.868333333 | 22.01153846 | 5.690186591 | 0.071818302 |
| RPS19BP1 | 14.89 | 41.31307692 | 2.774551842 | 0.071825088 |
| TSNAX | 8.946666667 | 47.33692308 | 5.291012266 | 0.071872299 |

TABLE 4-continued

Genes Enriched in P1 (arterial endothelial cells) vs. P3 (venous cells)

| SYMBOL | Average Venous | Average arterial | Arterial/Venous | p |
|---|---|---|---|---|
| MRPL2 | 51.55833333 | 123.6776923 | 2.398791511 | 0.071975114 |
| FAM101B | 5.973333333 | 20.17230769 | 3.37706044 | 0.072065154 |
| DCAF4 | 0.515 | 21.47 | 41.68932039 | 0.072109056 |
| AU041133 | 1.098333333 | 22.56 | 20.54021244 | 0.072256734 |
| UTP3 | 40.45833333 | 92.13538462 | 2.27729066 | 0.072281619 |
| GHITM | 104.5366667 | 229.7469231 | 2.197764004 | 0.072408307 |
| PWP1 | 11.47166667 | 53.19153846 | 4.636775109 | 0.072681631 |
| NGLY1 | 1.963333333 | 27.76230769 | 14.14039441 | 0.072980173 |
| LCMT1 | 7.988333333 | 48.44615385 | 6.064613459 | 0.073087799 |
| GUSB | 2.208333333 | 54.70923077 | 24.77399129 | 0.073104179 |
| ERLIN1 | 0.821666667 | 28.54384615 | 34.73896084 | 0.073439545 |
| PEX1 | 1.008333333 | 13.02615385 | 12.91849968 | 0.073596884 |
| ZFP213 | 0 | 2.616153846 | #DIV/0! | 0.07364258 |
| 1810043G02RIK | 3.758333333 | 42.48230769 | 11.3034965 | 0.073815133 |
| PPM1M | 9.055 | 55.05230769 | 6.079768933 | 0.074119249 |
| FAF1 | 0.28 | 21.60384615 | 77.15659341 | 0.074282706 |
| MPG | 6.378333333 | 41.29230769 | 6.473839722 | 0.074284242 |
| FEM1B | 15.08166667 | 47.09230769 | 3.122486973 | 0.074313525 |
| PRND | 91.23333333 | 413.7092308 | 4.534628032 | 0.074340949 |
| LGALS9 | 0 | 17.82230769 | #DIV/0! | 0.074396424 |
| AFF4 | 5.818333333 | 21.55538462 | 3.704735253 | 0.074543688 |
| SYT11 | 1.373333333 | 13.87846154 | 10.10567588 | 0.074599147 |
| THAP7 | 1.876666667 | 28.75846154 | 15.32422462 | 0.074762579 |
| FANCA | 0.75 | 4.398461538 | 5.864615385 | 0.074842805 |
| BRCA1 | 0.605 | 7.436923077 | 12.29243484 | 0.075035847 |
| ZFP395 | 1.325 | 4.239230769 | 3.199419448 | 0.075184804 |
| FASTKD2 | 2.106666667 | 34.70846154 | 16.47553554 | 0.075317103 |
| AA960436 | 2.48 | 27.60076923 | 11.12934243 | 0.075450343 |
| SCN2B | 0.65 | 11.79076923 | 18.13964497 | 0.075488674 |
| OIT3 | 2.066666667 | 50.04615385 | 24.21588089 | 0.075564105 |
| FTSJ1 | 5.628333333 | 23.77 | 4.223275096 | 0.075633763 |
| PRSS43 | 0.656666667 | 1.351538462 | 2.058180398 | 0.075737719 |
| 2310011J03RIK | 0.973333333 | 12.27538462 | 12.61169652 | 0.075772075 |
| MTERFD3 | 1.116666667 | 33.04538462 | 29.59288175 | 0.075936529 |
| GCOM1 | 30.17166667 | 109.2938462 | 3.622400027 | 0.076142485 |
| RHPN2 | 1.756666667 | 9.225384615 | 5.251642096 | 0.076437756 |
| ERO1L | 3.411666667 | 17.92461538 | 5.253917553 | 0.076475266 |
| GLT25D1 | 2.668333333 | 28.42692308 | 10.65343776 | 0.07649072 |
| HOXB5 | 0 | 4.008461538 | #DIV/0! | 0.076514631 |
| ARHGAP6 | 0 | 4.700769231 | #DIV/0! | 0.076631422 |
| 2810408M09RIK | 9.125 | 33.52076923 | 3.673508957 | 0.076681426 |
| HHEX | 3.306666667 | 37.29923077 | 11.28000931 | 0.076709174 |
| NENF | 0.396666667 | 7.282307692 | 18.35875889 | 0.076957706 |
| CDAN1 | 1.221666667 | 7.300769231 | 5.97607304 | 0.077035418 |
| GTPBP10 | 10.83166667 | 45.17153846 | 4.170322061 | 0.077134342 |
| AKAP2 | 24.88833333 | 65.69692308 | 2.639667438 | 0.077150809 |
| RFX1 | 0.378333333 | 9.636923077 | 25.47204338 | 0.077222052 |
| CCT6B | 0.416666667 | 2.223076923 | 5.335384615 | 0.07739899 |
| MIB1 | 11.11333333 | 29.37076923 | 2.642840663 | 0.077413192 |
| SFXN3 | 11.115 | 44.09615385 | 3.967265303 | 0.077614758 |
| TPST1 | 0.446666667 | 7.065384615 | 15.81802526 | 0.077673955 |
| TOMM22 | 99.79666667 | 229.6223077 | 2.300901577 | 0.077751857 |
| GNG3 | 0.215 | 4.396923077 | 20.45080501 | 0.077757389 |
| TTYH3 | 1.92 | 6.545384615 | 3.409054487 | 0.077901363 |
| PXDN | 30.36833333 | 69.64461538 | 2.293330181 | 0.078076924 |
| TRMT5 | 0 | 24.12384615 | #DIV/0! | 0.078096776 |
| PCDH1 | 0.78 | 25.93615385 | 33.25147929 | 0.078241262 |
| TRF | 4.176666667 | 38.07692308 | 9.116581742 | 0.078244798 |
| PAPD7 | 0.121666667 | 10.72615385 | 88.1601686 | 0.078349373 |
| FAM63A | 5.275 | 47.83307692 | 9.067881881 | 0.078493926 |
| DTX3 | 1.013333333 | 14.84461538 | 14.6492915 | 0.078495557 |
| EGLN1 | 18.66 | 58.30538462 | 3.124618682 | 0.078604265 |
| LAMB2 | 0.046666667 | 14.58538462 | 312.543956 | 0.078722122 |
| JKAMP | 25.19666667 | 84.03230769 | 3.33505653 | 0.078884402 |
| UBE2G2 | 16.19333333 | 66.61384615 | 4.113658676 | 0.07927351 |
| CD9 | 78.29166667 | 187.4415385 | 2.394144185 | 0.079393771 |
| PAPD5 | 7.001666667 | 29.12538462 | 4.159778807 | 0.07947003 |
| 5830433M19RIK | 2.936666667 | 14.77153846 | 5.030035798 | 0.079529283 |
| CCDC115 | 4.416666667 | 31.77538462 | 7.194426705 | 0.079533801 |
| SERINC3 | 20.18333333 | 58.57384615 | 2.902089818 | 0.079937391 |
| TBC1D4 | 0.49 | 18.47538462 | 37.70486656 | 0.07997626 |
| ZFP936 | 0.355 | 1.615384615 | 4.550379198 | 0.080109918 |
| FAM158A | 0 | 15.91230769 | #DIV/0! | 0.080445323 |
| ETAA1 | 0.543333333 | 10.66692308 | 19.63237376 | 0.080705637 |
| MYST1 | 0 | 35.48153846 | #DIV/0! | 0.080787758 |
| MICAL2 | 1.843333333 | 7.543846154 | 4.092502434 | 0.081485709 |

TABLE 4-continued

Genes Enriched in P1 (arterial endothelial cells) vs. P3 (venous cells)

| SYMBOL | Average Venous | Average arterial | Arterial/Venous | p |
|---|---|---|---|---|
| 1700021F05RIK | 45.13166667 | 130.0023077 | 2.880512006 | 0.081639691 |
| AFTPH | 0 | 10.92769231 | #DIV/0! | 0.081703171 |
| BLM | 9.335 | 26.98846154 | 2.89110461 | 0.081733816 |
| VPS13C | 0.305 | 3.502307692 | 11.48297604 | 0.081746041 |
| FBXW2 | 6.831666667 | 37.81461538 | 5.535196202 | 0.081782896 |
| EHD4 | 11.12666667 | 42.60692308 | 3.82926211 | 0.081782985 |
| ZFP746 | 5.821666667 | 28.69461538 | 4.928934793 | 0.081868957 |
| TPP2 | 40.015 | 107.2569231 | 2.68041792 | 0.082386499 |
| 3110040N11RIK | 11.76333333 | 45.52846154 | 3.870370774 | 0.082478516 |
| LRRK2 | 0.031666667 | 5.944615385 | 187.7246964 | 0.082509549 |
| MTMR11 | 0 | 18.52615385 | #DIV/0! | 0.082659818 |
| POLR2H | 75.4 | 178.6461538 | 2.369312385 | 0.08301763 |
| GRAP | 41.45833333 | 100.7638462 | 2.430484731 | 0.083047879 |
| DHX32 | 0.07 | 1.777692308 | 25.3956044 | 0.083171504 |
| EXOG | 2.391666667 | 32.61153846 | 13.63548646 | 0.083234252 |
| FREM1 | 0 | 2.106153846 | #DIV/0! | 0.083400371 |
| ABCA3 | 0.055 | 11.17384615 | 203.1608392 | 0.083492441 |
| ZFP692 | 0.093333333 | 27.01230769 | 289.4175824 | 0.083511612 |
| MTRF1L | 0.38 | 11.79461538 | 31.03846154 | 0.083565319 |
| TTC17 | 0.908333333 | 24.64538462 | 27.13253352 | 0.083591981 |
| NDRG4 | 0.048333333 | 22.71538462 | 469.9734748 | 0.083742907 |
| TPRGL | 6.11 | 54.65769231 | 8.945612489 | 0.083826264 |
| ATP9B | 4.38 | 30.31538462 | 6.921320688 | 0.083929184 |
| SDC3 | 0.91 | 10.60923077 | 11.65849535 | 0.084461087 |
| JAGN1 | 19.50833333 | 74.27230769 | 3.807209279 | 0.084512063 |
| HOXA3 | 2.305 | 14.26692308 | 6.18955448 | 0.084568934 |
| ANKRD49 | 15.33666667 | 72.39538462 | 4.720411951 | 0.084669253 |
| KDM5C | 7.55 | 16.58153846 | 2.19623026 | 0.084685266 |
| HIST1H2BK | 0 | 10.31923077 | #DIV/0! | 0.084808162 |
| HIST3H2A | 0 | 3.484615385 | #DIV/0! | 0.084868951 |
| TATDN2 | 0.095 | 4.943846154 | 52.04048583 | 0.08494456 |
| NRBP1 | 67.615 | 177.4661538 | 2.624656568 | 0.084947479 |
| EPB4.1L5 | 3.13 | 17.17307692 | 5.486606046 | 0.084988786 |
| MTMR4 | 1.741666667 | 14.32153846 | 8.222892897 | 0.085019684 |
| GCNT1 | 0.055 | 18.89153846 | 343.4825175 | 0.085118852 |
| MOAP1 | 2.406666667 | 20.36692308 | 8.46271042 | 0.085146926 |
| POLM | 0.046666667 | 12.84076923 | 275.1593407 | 0.085249177 |
| QSOX1 | 0.216666667 | 2.013846154 | 9.294674556 | 0.085259606 |
| SLC17A5 | 9.885 | 35.82692308 | 3.624372593 | 0.085349793 |
| PRKCE | 1.345 | 8.452307692 | 6.284243637 | 0.085444387 |
| CDK5RAP3 | 0.12 | 24.28461538 | 202.3717949 | 0.08607689 |
| ZNHIT2-PS | 0 | 7.737692308 | #DIV/0! | 0.08617829 |
| FBXW11 | 27.075 | 71.24538462 | 2.631408481 | 0.086198362 |
| TBC1D22B | 1.285 | 5.722307692 | 4.453157737 | 0.086479697 |
| RSBN1L | 3.188333333 | 19.6 | 6.147412441 | 0.086603607 |
| FAM168B | 15.53333333 | 44.54153846 | 2.867481017 | 0.086632754 |
| 4930452B06RIK | 0 | 2.956923077 | #DIV/0! | 0.08673539 |
| RAB23 | 0.118333333 | 13.69692308 | 115.7486457 | 0.087126177 |
| SEMA3A | 0.26 | 11.02769231 | 42.41420118 | 0.087255104 |
| PIBF1 | 4.38 | 35.08538462 | 8.010361784 | 0.08735497 |
| UBE3A | 27.88166667 | 60.75384615 | 2.178989043 | 0.08746605 |
| WWOX | 0 | 13.01923077 | #DIV/0! | 0.087513341 |
| LIME1 | 3.16 | 22.71307692 | 7.187682571 | 0.087514088 |
| 2210021J22RIK | 1.381666667 | 43.14153846 | 31.22427392 | 0.087561778 |
| STXBP5 | 0.216666667 | 5.331538462 | 24.60710059 | 0.087791523 |
| TMC7 | 0.151666667 | 14.85153846 | 97.92223161 | 0.088096566 |
| GM2058 | 9.375 | 65.04538462 | 6.938174359 | 0.088319952 |
| IFFO2 | 3.718333333 | 16.18846154 | 4.35368755 | 0.088509133 |
| MRPL38 | 7.89 | 47.35230769 | 6.00155991 | 0.088573901 |
| CDK2AP1 | 41.42333333 | 126.6184615 | 3.056694171 | 0.088830232 |
| FILIP1 | 0.146666667 | 5.945384615 | 40.53671329 | 0.088900629 |
| RABAC1 | 35.475 | 106.05 | 2.989429175 | 0.089018546 |
| SMTNL2 | 6.01 | 19.89076923 | 3.309612185 | 0.089067395 |
| CORO1B | 66.88666667 | 158.0946154 | 2.363619287 | 0.089086084 |
| RNPEPL1 | 5.7 | 31.52076923 | 5.529959514 | 0.089197406 |
| CNTROB | 0.043333333 | 5.869230769 | 135.443787 | 0.089204152 |
| MAPK3 | 68.19166667 | 140.4184615 | 2.059173333 | 0.089290852 |
| TRIM13 | 0 | 16.12769231 | #DIV/0! | 0.089447268 |
| MFN1 | 0.593333333 | 14.25923077 | 24.03241141 | 0.089526593 |
| ATXN1 | 0.158333333 | 6.222307692 | 39.29878543 | 0.089556559 |
| TOR1AIP1 | 6.466666667 | 27.20846154 | 4.207494052 | 0.08972818 |
| 4930444A02RIK | 1.983333333 | 5.843076923 | 2.946089205 | 0.089899132 |
| 6430527G18RIK | 1.82 | 5.698461538 | 3.131022823 | 0.089965414 |
| PTER | 3.01 | 20.27769231 | 6.736774853 | 0.090184994 |
| FBXO42 | 0.531666667 | 10.18769231 | 19.16180371 | 0.090275926 |
| ELK4 | 4.016666667 | 24.07 | 5.99253112 | 0.090321702 |

TABLE 4-continued

Genes Enriched in P1 (arterial endothelial cells) vs. P3 (venous cells)

| SYMBOL | Average Venous | Average arterial | Arterial/Venous | p |
|---|---|---|---|---|
| DHX40 | 4.04 | 24.59076923 | 6.086824067 | 0.090549444 |
| ATP9A | 0.948333333 | 27.15230769 | 28.63160741 | 0.090560867 |
| PXMP3 | 16.93666667 | 61.61846154 | 3.638169349 | 0.090575993 |
| GM5918 | 0.256666667 | 18.81384615 | 73.3006993 | 0.09066458 |
| SEL1L | 9.126666667 | 35.30923077 | 3.868798112 | 0.090703125 |
| COG1 | 3.73 | 34.38230769 | 9.217776861 | 0.091096262 |
| UTP20 | 2.581666667 | 7.744615385 | 2.999851021 | 0.091162217 |
| METTL13 | 0 | 1.809230769 | #DIV/0! | 0.091314321 |
| DTNBP1 | 6.423333333 | 31.12307692 | 4.845315556 | 0.09137728 |
| DCBLD1 | 3.488333333 | 37.20307692 | 10.66500055 | 0.091420667 |
| TRIP11 | 8.813333333 | 23.98076923 | 2.720964739 | 0.091457917 |
| EDN1 | 2.101666667 | 27.69923077 | 13.17964985 | 0.09145804 |
| TTPA | 0.061666667 | 7.979230769 | 129.3929314 | 0.091463134 |
| GPR180 | 1.023333333 | 10.13307692 | 9.902029567 | 0.091478453 |
| FBXO11 | 23.225 | 57.61615385 | 2.480781651 | 0.091670491 |
| TRP53INP1 | 0 | 19.60076923 | #DIV/0! | 0.091851979 |
| TMEM147 | 60.07666667 | 168.2623077 | 2.800793004 | 0.091857268 |
| FGFR2 | 0.073333333 | 15.16846154 | 206.8426573 | 0.091862636 |
| SMC5 | 15.54666667 | 35.28769231 | 2.269791529 | 0.091894325 |
| SALL4 | 0 | 59.29384615 | #DIV/0! | 0.091924063 |
| ETV3 | 0.871666667 | 20.86461538 | 23.93646124 | 0.09194535 |
| FNIP2 | 2.345 | 15.99846154 | 6.822371658 | 0.092117245 |
| HSPA13 | 30.865 | 76.65692308 | 2.483619734 | 0.092160083 |
| PLXNA2 | 1.018333333 | 6.062307692 | 5.95316631 | 0.092203574 |
| TMEM115 | 2.766666667 | 19.09 | 6.9 | 0.09221924 |
| SOLH | 1.17 | 5.256923077 | 4.493096647 | 0.092247217 |
| GSTZ1 | 2.51 | 64.62538462 | 25.74716519 | 0.092258383 |
| MFSD6 | 0.423333333 | 2.280769231 | 5.387643852 | 0.092479056 |
| 2310022A10RIK | 0.406666667 | 6.086153846 | 14.96595208 | 0.092553602 |
| TMEM66 | 5.94 | 65.58615385 | 11.04144004 | 0.092857173 |
| GCAT | 9.278333333 | 42.12230769 | 4.539857125 | 0.093123416 |
| CXCR7 | 11.72 | 53.78461538 | 4.589131006 | 0.09314384 |
| TATDN1 | 3.045 | 24.37923077 | 8.006315524 | 0.09316526 |
| BIN1 | 5.986666667 | 29.13615385 | 4.866840843 | 0.093255424 |
| E2F3 | 0.36 | 5.876153846 | 16.32264957 | 0.093659226 |
| PPP2R5A | 1.905 | 22.96230769 | 12.05370483 | 0.093767868 |
| DAG1 | 8.025 | 29.70769231 | 3.701893122 | 0.093858638 |
| EZH1 | 0.881666667 | 9.670769231 | 10.96873637 | 0.093877551 |
| REEP1 | 0.11 | 21.07153846 | 191.5594406 | 0.093879695 |
| PHPT1 | 169.3266667 | 346.5476923 | 2.046622066 | 0.093969581 |
| AMBRA1 | 1.726666667 | 10.70615385 | 6.2004752 | 0.094060067 |
| SBF2 | 10.61666667 | 33.22769231 | 3.129766936 | 0.094061511 |
| PDDC1 | 23.91333333 | 98.18 | 4.105659325 | 0.094109405 |
| ZBTB39 | 0.445 | 7.649230769 | 17.18928263 | 0.094264899 |
| ALG11 | 0.296666667 | 10.02307692 | 33.78565255 | 0.094288288 |
| SGIP1 | 0.291666667 | 3.756153846 | 12.87824176 | 0.094575454 |
| SIGIRR | 0 | 10.66230769 | #DIV/0! | 0.094598079 |
| EMP3 | 4.958333333 | 54.22846154 | 10.93683258 | 0.094824097 |
| DGKH | 0.081666667 | 6.36 | 77.87755102 | 0.094868476 |
| CTNNBIP1 | 0.03 | 7.819230769 | 260.6410256 | 0.095187154 |
| RNF141 | 0.951666667 | 42.28615385 | 44.43378688 | 0.095319 |
| SDC2 | 5.173333333 | 51.55692308 | 9.965900079 | 0.095348192 |
| CDYL | 2.603333333 | 28.02076923 | 10.76341968 | 0.095410278 |
| MTMR3 | 1.261666667 | 22.02461538 | 17.45676252 | 0.095537086 |
| 2310003H01RIK | 0.46 | 45.96615385 | 99.9264214 | 0.09571754 |
| MREG | 0.04 | 3.934615385 | 98.36538462 | 0.095767806 |
| DOT1L | 4.913333333 | 12.80461538 | 2.606095397 | 0.095898107 |
| PLEKHA1 | 20.235 | 77.14384615 | 3.812396647 | 0.096096971 |
| VPS8 | 0.211666667 | 5.752307692 | 27.17625681 | 0.09615618 |
| H2AFJ | 3.13 | 8.043846154 | 2.569918899 | 0.09616433 |
| GTF3C3 | 1.79 | 10.75769231 | 6.009883971 | 0.096236639 |
| FZD7 | 0.318333333 | 1.48 | 4.64921466 | 0.096282298 |
| HAUS2 | 16.255 | 55.17692308 | 3.39445851 | 0.096282605 |
| LRRC42 | 14.73 | 56.98 | 3.868295995 | 0.096307002 |
| PUS7L | 0 | 19.13615385 | #DIV/0! | 0.096501578 |
| DDX49 | 7.923333333 | 58.56307692 | 7.391217113 | 0.096688134 |
| ARRB2 | 0.415 | 2.435384615 | 5.868396664 | 0.096710155 |
| CUTC | 0.468333333 | 47.42076923 | 101.2543115 | 0.096772584 |
| RRAGA | 0.716666667 | 28.74 | 40.10232558 | 0.096773662 |
| HAS2 | 0 | 7.902307692 | #DIV/0! | 0.097054884 |
| CUX1 | 3.91 | 31.22923077 | 7.987015542 | 0.09705562 |
| ACOT8 | 0 | 9.064615385 | #DIV/0! | 0.097142277 |
| ZFP58 | 0.86 | 19.77076923 | 22.98926655 | 0.097225082 |
| EFNA1 | 152.66 | 317.8 | 2.081750295 | 0.097431704 |
| PACS2 | 4.711666667 | 16.33846154 | 3.467660744 | 0.097437511 |
| 5730403B10RIK | 19.50666667 | 57.61307692 | 2.953507019 | 0.097515148 |

TABLE 4-continued

Genes Enriched in P1 (arterial endothelial cells) vs. P3 (venous cells)

| SYMBOL | Average Venous | Average arterial | Arterial/Venous | p |
|---|---|---|---|---|
| RND3 | 22.19166667 | 111.0853846 | 5.00572518 | 0.097576798 |
| CCDC28A | 0 | 2.475384615 | #DIV/0! | 0.097626798 |
| 1500009L16RIK | 2.046666667 | 18.86615385 | 9.217990479 | 0.097677532 |
| SOX18 | 26.20333333 | 69.22769231 | 2.641942207 | 0.097679365 |
| 1700025G04RIK | 2.005 | 5.525384615 | 2.755802801 | 0.097747959 |
| KLF4 | 9.098333333 | 38.94846154 | 4.280834754 | 0.097779938 |
| PDLIM1 | 4.161666667 | 54.08384615 | 12.99571794 | 0.097813795 |
| RELN | 0 | 2.663846154 | #DIV/0! | 0.098090859 |
| LETMD1 | 0.741666667 | 42.64461538 | 57.49835782 | 0.098178385 |
| PYCR2 | 13.975 | 51.68 | 3.6980322 | 0.098386231 |
| BCAS3 | 0.095 | 10.15615385 | 106.9068826 | 0.098499825 |
| CHN1 | 6.918333333 | 28.86538462 | 4.172303245 | 0.09863188 |
| LDLR | 1.35 | 5.981538462 | 4.430769231 | 0.098711275 |
| PKD2L2 | 0.35 | 2.766153846 | 7.903296703 | 0.098945217 |
| MTAP4 | 25.88333333 | 60.14076923 | 2.323532617 | 0.098988923 |
| ROBO2 | 0 | 4.482307692 | #DIV/0! | 0.099108054 |
| COPZ2 | 0.541666667 | 22.39692308 | 41.34816568 | 0.09915995 |
| INTS7 | 36.29333333 | 85.40307692 | 2.353134008 | 0.099393182 |
| AGPAT4 | 17.75 | 47.84769231 | 2.695644637 | 0.099419301 |
| CFL2 | 44.70166667 | 105.5246154 | 2.360641633 | 0.099522782 |
| CD2AP | 39.62166667 | 93.75153846 | 2.366168472 | 0.099591675 |
| ZBTB10 | 3.166666667 | 28.44923077 | 8.983967611 | 0.099729084 |
| 1810008A18RIK | 0.483333333 | 21.95 | 45.4137931 | 0.099791657 |
| TRIOBP | 2.751666667 | 29.92 | 10.87341005 | 0.099835126 |
| 9030025P20RIK | 7.903333333 | 17.32538462 | 2.192161697 | 0.099870069 |
| CRY2 | 2.626666667 | 14.22153846 | 5.414291292 | 0.099894165 |
| DDX26B | 9.481666667 | 25.61538462 | 2.701569831 | 0.099983822 |

We claim:

1. A method of obtaining human arterial endothelial cells, the method comprising
culturing human mesodermal cells in a serum-free, albumin-free, chemically defined culture medium that is free of insulin and comprises a fibroblast growth factor (FGF), a vascular endothelial growth factor (VEGF), a Notch agonist, a TGF-beta inhibitor, and an inhibitor of inositol monophosphatase for about 6 days until a cell population comprising at least 80% human Ephrin B2 (EFNB2)-positive arterial endothelial cells and comprising fewer than 20% EphB4+ cells is obtained.

2. The method of claim 1, wherein the mesodermal cells express one or more mesodermal markers selected from the group consisting of Brachyury (T), EMOS, FOXA2, MIXL1, MSX1, and MSX2.

3. The method of claim 1, wherein the human mesodermal cells are obtained by culturing human pluripotent stem cells for a period of about two days in a serum-free, albumin-free, chemically defined cell culture medium comprising a Bone Morphogenetic Protein (BMP), Activin A, and an activator of Wnt/β-catenin signaling to obtain a cell population comprising mesodermal cells.

4. The method of claim 3, wherein the mesodermal cells express one or more mesodermal markers selected from the group consisting of Brachyury (T), EMOS, FOXA2, MIXL1, MSX1, and MSX2.

5. The method of claim 3, wherein the pluripotent stem cells are human embryonic stem cells or human induced pluripotent stem cells.

6. The method of claim 3, wherein the activator of Wnt/β-catenin signaling is a Gsk3 inhibitor.

7. The method of claim 6, wherein the Gsk3 inhibitor is selected from the group consisting of CHIR 99021, CHIR 98014, BIO-acetoxime, BIO, LiCl, SB 216763, SB 415286, AR A014418, 1-Azakenpaullone, and Bis-7-indolylmaleimide.

8. The method of claim 1, wherein the Notch agonist is selected from the group consisting of Resveratrol (3,4',5-trihydroxystilbene), valproic acid, and suberoyl bishydroxamic acid.

9. The method of claim 1, wherein the TGF-beta inhibitor is SB431542.

10. The method of claim 1, wherein the inhibitor of inositol monophosphatase is L-690,330.

11. A kit for obtaining a cell population comprising at least 80% arterial endothelial cells, the kit comprising: (i) a serum-free, albumin-free, chemically defined culture medium suitable for differentiation of mesodermal cells into arterial endothelial cells, wherein the culture medium is free of insulin and comprises a fibroblast growth factor (FGF), a vascular endothelial growth factor (VEGF), a Notch agonist, a TGF-beta inhibitor, and an inhibitor of inositol monophosphatase; and (ii) instructions describing a method for differentiating human mesodermal cells into a cell population comprising at least 80% arterial endothelial cells, the method comprising human mesodermal cells for about six days in the serum-free, albumin-free, chemically defined culture medium until a cell population comprising, at least 80% EFNB2+ human arterial endothelial cells and comprising fewer than 20% EphB4+ cells.

12. The kit of claim 11, further comprising:
(a) a serum-free, albumin-free, chemically defined culture medium suitable for differentiation of human pluripotent stem cells into human mesodermal cells, the culture medium comprising a BMP, Activin A, and an activator of Wnt/β-catenin signaling; and
(b) instructions describing a method for differentiating human pluripotent stem cells into human mesodermal cells, the method employing the culture medium of (a).

* * * * *